(12) United States Patent
Wong et al.

(10) Patent No.: US 8,507,660 B2
(45) Date of Patent: Aug. 13, 2013

(54) ALPHA-SELECTIVE SIALYL PHOSPHATE DONORS FOR PREPARATION OF SIALOSIDES AND SIALOSIDE ARRAYS FOR INFLUENZA VIRUS DETECTION

(75) Inventors: Chi-Huey Wong, La Jolla, CA (US); Ting-Jen Rachel Cheng, Taipei (TW); Chung-Yi Wu, Taipei (TW)

(73) Assignee: Academia Sinica, Taipei (TW)

( * ) Notice: Subject to any disclaimer, the term of this patent is extended or adjusted under 35 U.S.C. 154(b) by 280 days.

(21) Appl. No.: 12/749,118

(22) Filed: Mar. 29, 2010

(65) Prior Publication Data

US 2011/0046003 A1 Feb. 24, 2011

Related U.S. Application Data

(60) Provisional application No. 61/164,375, filed on Mar. 27, 2009.

(51) Int. Cl.
| | | |
|---|---|---|
| *C07H 1/00* | (2006.01) | |
| *C07H 5/06* | (2006.01) | |
| *C07H 7/04* | (2006.01) | |
| *C07H 9/06* | (2006.01) | |
| *C40B 30/04* | (2006.01) | |
| *C40B 50/00* | (2006.01) | |
| *C40B 40/12* | (2006.01) | |

(52) U.S. Cl.
USPC ....... 536/17.1; 536/17.2; 536/17.3; 536/17.4; 536/124; 506/9; 506/19; 506/23; 506/27

(58) Field of Classification Search
None
See application file for complete search history.

(56) References Cited

PUBLICATIONS

Martin, T. et al "Synthesis of phosphites and phosphates of neuraminic acid . . . " Glycoconj. J. (1993) vol. 10, p. 16-25.*
Chokhawala, H. et al "High-throughput substrate specificity studies . . . " ChemBioChem (2007) vol. 8, pp. 194-201.*
Farris, M. et al "Application of 4,5-O,N-oxazolidinone protected thiophenyl sialosyl donor . . . " Tet. Lett. (2007) vol. 48, pp. 1225-1227.*
Tanaka, H. et al "Synthetic study of alpha(2,8) oligosialoside . . . " Heterocycles (2006) vol. 67, No. 1, pp. 107-112.*

* cited by examiner

Primary Examiner — Leigh Maier
(74) Attorney, Agent, or Firm — Eckman Basu LLP

(57) ABSTRACT

A novel N-acetyl-5-N,4-O-carbonyl-protected dibutyl sialyl phosphate donor for sialylation of both primary and sterically hindered secondary acceptors to prepare sialosides with high yield and α-selectivity is disclosed. Methods for making disaccharide building blocks comprising α(2→3), α(2→6), α(2→8), α(2→8)/α(2→9) alternate, and α(2→9) sialosides are provided. methods for one-pot synthesis of complex sialosides are disclosed. Libraries of sialosides and methods for using the libraries for detection and receptor binding analysis of surface glycoproteins or pathogens and cancer cells are disclosed. Methods for distinguishing between hemagglutinin (HA) from various strains of influenza are provided.

43 Claims, 20 Drawing Sheets

α2,3 sialosides: No. 1-17

α2,6 sialosides: No. 21-30

FIG. 6

| Sugar | $K_D$ of Hemagglutinin (nM) | | |
|---|---|---|---|
| | Cal07(H1N1) | Br59 (H1N1) | Br10 (H3N2) |
| 24 | 376 ± 40 | 233 ± 23 | 6350 ± 110 |
| 28 | 1307 ± 533 | 443 ± 156 | 2011 ± 746 |
| 29 | 383 ± 9 | N.D.* | >10⁵ |
| 30 | 686 ± 230 | N.D.* | 836 ± 96 |
| *: High binding activities but no concentration-dependence was observed. | | | |

FIG. 7-1

| [a] Sialosides | wt | Δ39 | Δ170 | Δ181 | Δ302 |
|---|---|---|---|---|---|
| 1 | 293 ± 130 | 540 ± 240 | 594 ± 157 | 1797 ± 848 | 657 ± 580 |
| 2 | 212 ± 19 | 792 ± 63 | 443 ± 56 | 902 ± 110 | 499 ± 278 |
| 3 | 249 ± 67 | 783 ± 77 | 527 ± 252 | 919 ± 63 | 528 ± 193 |
| 4 | 207 ± 52 | 497 ± 81 | 494 ± 79 | 795 ± 194 | 290 ± 118 |
| 5 | 276 ± 79 | 905 ± 261 | 1044 ± 244 | 1783 ± 1270 | 339 ± 228 |
| 6 | 237 ± 33 | 493 ± 64 | 675 ± 183 | 852 ± 35 | 353 ± 174 |
| 7 | 372 ± 327 | 774 ± 173 | 579 ± 245 | 889 ± 45 | 485 ± 217 |
| 8 | 351 ± 192 | 732 ± 95 | 588 ± 376 | 1372 ± 333 | 552 ± 185 |
| 9 | 300 ± 94 | 738 ± 214 | 1000 ± 545 | 2021 ± 374 | 339 ± 30 |

FIG. 7-2

| [a] Sialosides | wt | Δ39 | Δ170 | Δ181 | Δ302 |
|---|---|---|---|---|---|
| 10 | 220 ± 130 | 509 ± 130 | 349 ± 197 | 653 ± 35 | 346 ± 136 |
| 11 | 199 ± 83 | 381 ± 169 | 338 ± 345 | 691 ± 213 | 348 ± 7 |
| 12 | 336 ± 301 | 690 ± 211 | 411 ± 17 | 1563 ± 718 | 526 ± 49 |
| 13 | 190 ± 87 | 368 ± 84 | 424 ± 416 | 603 ± 381 | 323 ± 127 |
| 14 | 171 ± 30 | 440 ± 13 | 355 ± 162 | 506 ± 249 | 286 ± 138 |
| 15 | 145 ± 44 | 398 ± 42 | 342 ± 312 | 990 ± 433 | 358 ± 53 |

[a]: Standard symbols used. ● Glc; ■ GlcNac, ◆ Neu5Ac, ○ Gal, □ GalNac, ⬢ Man, ▲ Fuc, R = $(CH_2)_5NH_2$

Scheme 1. Stepwise Synthesis of Influenza HA Receptor α(2→6)-Linked Trisaccharide 28.

FIG. 9

Scheme 2:
One-Pot Synthesis of Influenza HA Receptors α(2→3) and α(2→6)-Linked Trisaccharides and DSGG Epitope Tetrasaccharide

Scheme 3. One-Pot Synthesis of SSEA-4 Hexasaccharide.

Scheme 4. Synthesis of Disaccharide 33

Scheme 5. Synthesis of α(2→9)-Linked Disaccharide Building Blocks

Scheme 6. Synthesis of α(2→9) Octasialic Acid

Scheme 7. Synthesis of di-, tri-, tetra-, hexa-, octa-sialic acid derivatives.

Scheme 8. Synthesis of α(2→8), α(2→9) alternative polysialic acids.

Scheme 9. Reactivity-Based One-Pot Glycosylation of Pentasaccharide 75

ALPHA-SELECTIVE SIALYL PHOSPHATE DONORS FOR PREPARATION OF SIALOSIDES AND SIALOSIDE ARRAYS FOR INFLUENZA VIRUS DETECTION

CROSS-REFERENCE TO RELATED APPLICATIONS

This application claims priority of U.S. provisional patent application Ser. No. 61/164,375, titled "A NEW ALPHA-SELECTIVE SIALYLATION DONOR FOR PRIMARY AND SECONDARY HYDROXYLS AND ITS USE IN PREPARATION OF GLYCAN ARRAY FOR PROFILING THE SPECIFICITY OF INFLUENZA HEMAGGLUTININ" filed Mar. 27, 2009, the contents of which are incorporated herein in their entirety by reference.

TECHNICAL FIELD OF THE INVENTION

The invention generally relates to the synthesis of sialosides. In particular, the invention relates to synthesis of disialides using novel sialyl phosphate donor compounds. Specifically, the invention relates to synthesis of polysialic acids using novel sialyl phosphate donor compounds and their use in detection and analysis of binding reactions.

BACKGROUND OF THE INVENTION

N-acetyl neuraminic acid (Neu5Ac) is the most abundant derivative of sialic acid found at the terminal end of glycoproteins or glycolipids. Neu5Ac-containing conjugates on the cell surface are often the receptors for viruses and bacteria and also are involved in a variety of biological processes such as tumor metastasis, cell differentiation and cell-cell interactions.[1] Influenza hemagglutinin (HA), for example, is the primary protein responsible for interacting with the sialosides on host-cell membrane to direct viral entry.[2]

In naturally occurring sialosides, Neu5Ac is often linked to galactosides through the α(2→3) or α(2→6) linkage in both N-linked and O-linked glycoproteins, and also to N-acetylgalactosamine through the α(2→6) linkage in O-linked glycoproteins. In addition, Neu5Ac can be linked to another Neu5Ac residue via the α(2→8) or α(2→9) linkage as a constituent of glycoconjugates.[3] Preparation of sialosides with α-glycosidic linkage, however, still represents a major challenge, mainly due to the presence of the electron-withdrawing carboxyl group at the tertiary anomeric center and the lack of a participating group at C-3. As a result, low-yield, undesired 2,3-elimination, and the formation of unnatural β glycosidic bonds occurs. Further, the separation of α- and β-isomers is tedious and sometimes very challenging. Though enzymatic sialylation provides stereo-specific α-linked sialosides, it is limited to, with some exceptions, the synthesis of naturally occurring sialosides.[4]

Over the past several years, major efforts have been directed toward the development of sialic acid donors for efficient α-sialylation[5], including the use of sialyl donors with halides,[6] phosphites,[7] sulfides,[8] xanthates,[9] or phenyltrifluoroacetimidates as leaving groups,[10] or with an auxiliary group at C-1[11] and C-3,[12] or with a modified N-acetyl functional group at C-5[13]. Another type of sialyl donors combines the best leaving group with the best positional modification for selective α-sialylation.[14] To date, however, there is no general sialyl donor available for use in preparing all naturally occurring sialosides with α(2→3), α(2→6), α(2→8), or α(2→9) linkages.

Development of efficient synthesis of oligosaccharides, using armed-disarmed,[15] one-pot,[16] reactivity-based programmable one-pot,[8b,17] solid phase,[18] orthogonal,[19] and pre-activation[20] methods, has been reported to reduce the complexity of protecting group manipulation.[17-18] However, one-pot synthesis of sialosides still presents a major problem due to the low reactivity and selectivity of sialylation reagents.[14a, 21-22] A strategy based on the use of appropriate orthogonal leaving groups has been demonstrated for the stereoselective synthesis of α(2→9) pentasialic acids, in which sialyl phosphite was chosen as the donor and thiosialoside as the acceptor for repeating coupling and anomeric leaving group adjustments.[14b] In addition, the preparation of α(2→6)-linked sialo-trisaccharides was accomplished by the sequential assembly of three building blocks composed of a sialyl donor with S-benzoxazolyl (S-Box) leaving group, a thiogalactoside as first acceptor and a 1-O-methyl glucoside as second acceptor,[23] to give the α-selective product (α/β ratio of 2.2:1 to 2.7:1). Takahashi and co-workers described a related one-pot study using S-Box sialyl donor with additional 5N, 4O-oxazolidinone protection, and achieved an elegant synthesis of α(2→9) trisialic with improved α-selectivity.[14e] Another excellent orthogonal strategy of one-pot synthesis of α(2→3)-linked N-glycolylneuraminic acids is to use admantanyl thiosialoside as a sialyl donor.[14f] Therefore, there is a need to develop a new sialic acid donor with an efficient leaving group that can be used as a general donor in an orthogonal strategy for the convergent synthesis of various sialosides with different linkages.

Sialyl phosphite,[7a-d] has been used for selective α-sialylation, but less attention has been given to the corresponding phosphate because of its poor α-selectivity in glycosidation reactions.[7a,7d]

SUMMARY OF THE INVENTION

A new set of highly α-selective sialylation reagents, with the combination of C-4/C-5 modification and dibutyl phosphate leaving group, was synthesized and used for the efficient synthesis of α-sialosides. The sialyl phosphate donor with N-acetyl-5-N,4-O-carbonyl protecting group was used to create five sialylated disaccharide building blocks commonly found in natural products, including Neu5Acα(2→3)Gal, Neu5Acα(2→6)Gal, Neu5Acα(2→6)GalNAc, Neu5Acα(2→9)Neu5Ac, and Neu5Acα(2→8)Neu5Ac, with excellent yields and α-stereoselectivity. By using the sialylated disaccharides as donors, one-pot protocols have been developed for the synthesis of α(2→3) and α(2→6) sialosides, including influenza hemagglutinin (HA) ligands, renal cell carcinoma associated antigen DSGG epitope tetrasaccharide, and stage-specific embryonic antigen-4 (SSEA-4). In addition, a convergent synthesis of α(2,9)-linked tetra- to α(2,9)-linked octasialic acids are reported.

Moreover, these synthesized sialosides are spotted onto a substrate to generate a sialoside array for influenza HA and real virus binding profiling. A library of 27 sialosides, including seventeen α(2→3) and ten α(2→6) glycans using the "sialylated disaccharide" building blocks has been synthesized and used for the preparation of a glycan array, which contains different glycan lengths, linkages, sugar types, and additional sulfation. This array was used to profile the binding specificity of different influenza hemagglutinins expressed from mammalian and insect cell systems to examine the effect of HA glycosylation on receptor binding. It was found that the HAs from insect cells bind to the sialoside receptors more strongly than that from human cells with differences in binding specificity and that the glycosylation on Asn27 is important for HA-receptor interaction.

The invention provides a sialyl phosphate donor compound for synthesis of sialosides comprising: an N-acetyl-5-N,4-O-carbonyl, a 5-N,4-O-carbonyl a 5-N-Trifluoroacetyl, a 5-N-Acetyl, or a 5-azido protecting group; and an alkyl, aryl or mixed alkyl aryl phosphate leaving group. In one aspect, The compound has the structure:

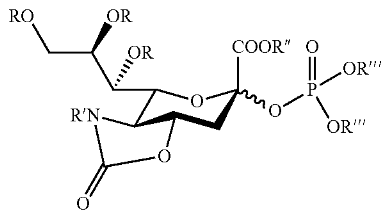

R = Ac, ClAc etc.
R′ = H, Ac etc.
R″ = Alkyl or Aryl, e.g. Me, Et, Ph, Bn…
R‴ = Alkyl or Aryl e.g. Butyl, Phenyl, Aryl… wherein R is independently H or a group selected from: acetyl, chloroacetyl, benzyl, thiobenzyl, benzylidine, and phenacyl; R' is independently H or acetyl; R" is independently H or selected from the group consisting of: $C_1$-$C_{20}$ alkyl, $C_6$-$C_{20}$ aryl, $C_2$-$C_{20}$ alkenyl, $C_2$-$C_{20}$ alkynyl, $C_3$-$C_{20}$ cycloalkyl, $C_3$-$C_{20}$ cycloaryl, $C_3$-$C_{20}$ cycloalkenyl, heteroaryl, aralkyl and heteroaralkyl; each R'" is independently selected from the group consisting of: $C_1$-$C_{20}$ alkyl, $C_6$-$C_{20}$ aryl, $C_2$-$C_{20}$ alkenyl, $C_2$-$C_{20}$ alkynyl, $C_3$-$C_{20}$ cycloalkyl, $C_3$-$C_{20}$ cycloaryl, $C_3$-$C_{20}$ cycloalkenyl, heteroaryl, aralkyl and heteroaralkyl, and any salt or stereoisomer thereof.

In one aspect the compound has the following structure 6:

6

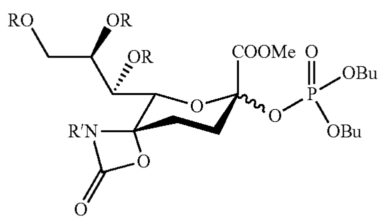

R = R′ = Ac
R = Ac, R′ = H
R = ClAc, R′ = Ac
R = ClAc, R′ = H
R = R′ = other protecting group
α = 6a
β = 6b The invention provides a method for synthesizing a sialoside, the method comprises: coupling a thiosialoside with a dibutyl phosphate in the presence of N-iodosuccinimide and catalytic trifluoromethanesulfonic (triflic) acid under suitable conditions; and isolating an N-acetyl-5-N,4-O-carbonyl-protected dibutyl sialyl phosphate donor. In some aspects, the sialoside comprises an α-glycosidic linkage.

In one embodiment, the thiosialoside is selected from the group consisting of:

1a

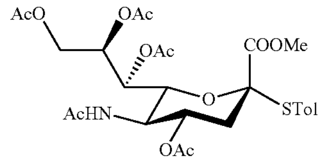

1b

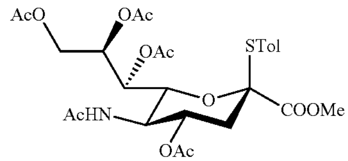

3a

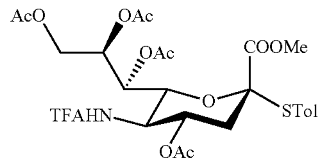

3b

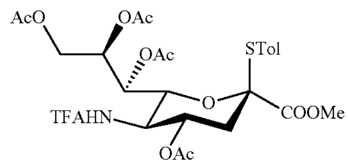

5a

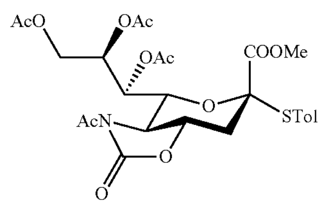

5b 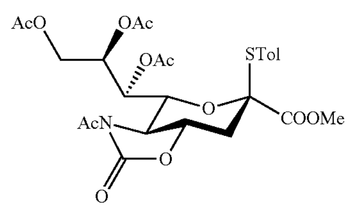 and

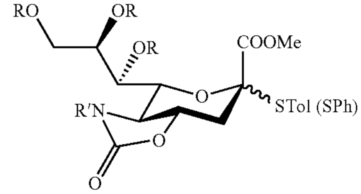

R = R′ = Ac
R = Ac, R′ = H
R = ClAc, R′ = Ac
R = ClAc, R′ = H
R = R′ = other protecting group In some aspects, the method comprises separating sialyl α-phosphate from sialyl-βphosphate by a process comprises chromatography.

In one embodiment, the N-acetyl-5-N,4-O-carbonyl-protected dibutyl sialyl phosphate donor comprises sialyl α-phosphate 6a or sialyl-β phosphate 6b having the formula:

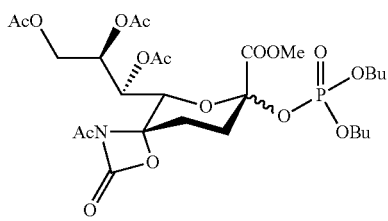

α = 6a
β = 6b and the N-acetyl-5-N,4-O-carbonyl-protected thiosialoside is:

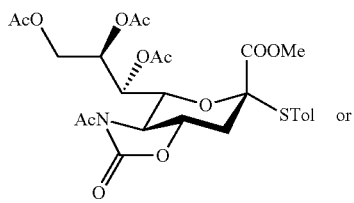

5a or

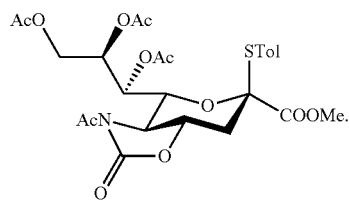

5b

In one aspect, the method comprises the steps of α-selective synthesis of a sialyl disaccharide building block comprises N-acetyl neuraminic acid (Neu5Ac) by: coupling the N-acetyl-5-N,4-O-carbonyl-protected dibutyl sialyl phosphate donor with a suitable thiogalactoside acceptor. In one embodiment, the disaccharide building block comprises N-acetyl neuraminic acid (Neu5Ac) is primarily α-anomeric. In one embodiment, the coupling is promoted by the reagent trimethylsilyl trifluoromethanesulfonate (TMSOTf).

In some aspects, the sialyl disaccharide building block is Neu5Acα(2→6)Gal, and a 4,6-dihydroxy thiogalactoside acceptor of the formula:

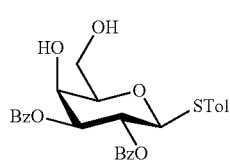

13 is coupled with the N-acetyl-5-N,4-O-carbonyl-protected dibutyl sialyl phosphate donor 6a to produce a Neu5Acα(2→6)Gal of the formula:

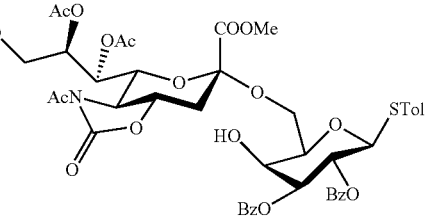

14

In some aspects, the sialyl disaccharide building block is Neu5Acα(2→3)Gal, and a tolyl-2-O-benzoyl-4,6-benzylidine-1-thio-β-D-galactopyranoside acceptor 17 of the formula:

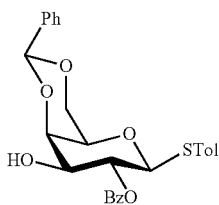

17 is coupled with the N-acetyl-5-N,4-O-carbonyl-protected dibutyl sialyl phosphate donor 6a to produce a Neu5Acα(2→3)Gal of the formula:

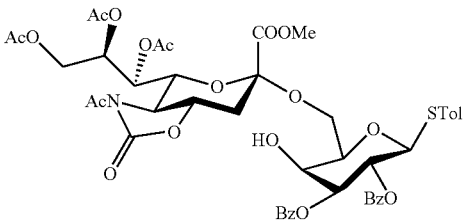

14

In some aspects, the sialyl disaccharide building block is Neu5Acα(2→6)GalNAc, and a tolyl-2-O-benzoyl-4,6-benzylidine-1-thio-β-D-galactopyranoside acceptor 19 or 21 of the formula:

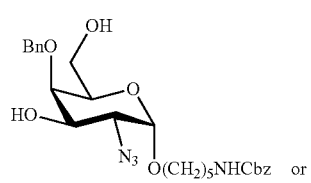

19 or

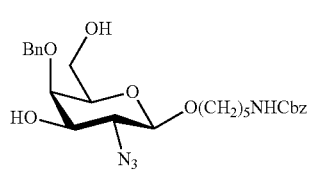

21 is coupled with the N-acetyl-5-N,4-O-carbonyl-protected dibutyl sialyl phosphate donor 6a to produce a Neu5Acα(2→6)GalNAc of the formula:

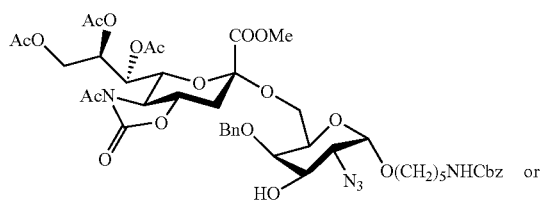

20

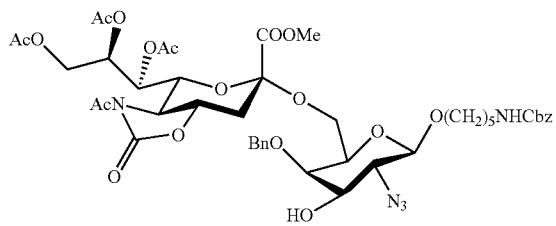

22 respectively.

In some aspects, the Neu5Acα(2→6)GalNAc disaccharide building block is used for the synthesis of an O-sialylated antigen STn, 2,6-STF, 2,3-STF, or glycophorin.

In some embodiments the method further comprises the steps of a one pot α-selective synthesis of a sialyl trisaccharide building block comprises N-acetyl neuraminic acid (Neu5Ac) by: first contacting the N-acetyl-5-N,4-O-carbonyl-protected dibutyl sialyl phosphate donor with a first thiogalactoside acceptor in a reaction for a time suitable to produce a disaccharide; and then adding a second acceptor to the reaction mix and allowing a second coupling reaction to produce a trisaccharide.

In some aspects, the trisaccharide comprises an influenza hemagglutinin (HA) receptor α(2→3) linked or α(2→6) linked trisaccharide. In some aspects, the one pot reaction is as shown in Scheme 1 or Scheme 2. In some aspects, the second acceptor is a trisaccharide. The one pot reaction produces a monosialosyl globopentaosylceramide, stage specific embryonic antigen-4 (SSEA-4).

In some aspects, the sialyl disaccharide building block is Neu5Acα(2→8)Neu5Ac, and a 7,8-dihydroxy thiogalactoside acceptor of the formula 40:

40

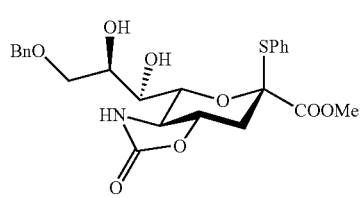

is coupled with the N-acetyl-5-N,4-O-carbonyl-protected dibutyl sialyl phosphate donor 6a to produce a Neu5Acα(2→8)Neu5Ac of the formula 41:

41

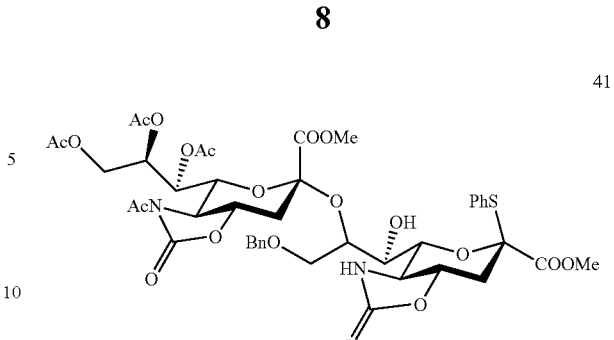

In some aspects, the sialyl disaccharide building block is Neu5Acα(2→9)Neu5Ac, and a 7,8,9-trihydroxy thiogalactoside acceptor of the formula 42:

42

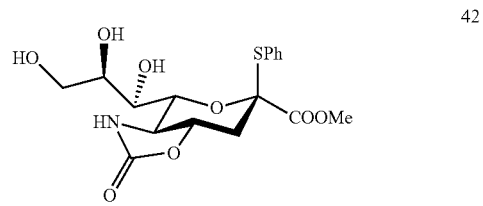

is coupled with the N-acetyl-5-N,4-O-carbonyl-protected dibutyl sialyl phosphate donor 6a to produce a Neu5Acα(2→9)Neu5Ac of the formula 43:

43

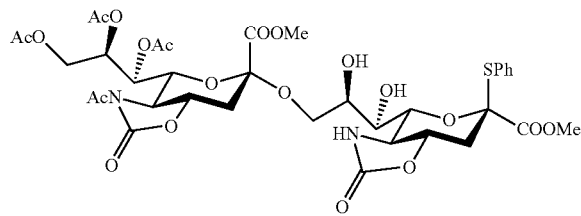

In some aspects, the method further comprises α-selective synthesis of a sialyl α(2→9) tetrasaccharide comprises N-acetyl neuraminic acid (Neu5Ac) by: first contacting the N-acetyl-5-N,4-O-carbonyl-protected dibutyl sialyl phosphate donor with a suitable thiosialoside acceptor in a reaction for a time suitable to produce a first Neu5Acα(2→9)Neu5Ac disaccharide with a SPh leaving group in the reducing end; then transferring this thiophenyl disialic acid to the dibutyl sialyl phosphate donor; and then adding a second Neu5Acα(2→9)Neu5Ac disaccharide to the reaction mix and allowing a second coupling reaction to produce a (Neu5Acα(2→9)Neu5Ac)₂ tetrasialoside.

The invention comprises preparation of a (Neu5Acα(2→9)Neu5Ac)₄ octosialoside. In some aspects, the octosialoside comprises a synthetic antigen for Neisserian *meningiditis*. In some aspects, the octosialoside further comprises an azido alkyl pentyl group in the reducing end suitable for conjugating the octosialoside to a protein or peptide.

The method comprises α-selective synthesis of α(2→8)/α(2→9) alternative polysialic acids by: first contacting the N-acetyl-5-N,4-O-carbonyl-protected dibutyl sialyl phosphate donor with a suitable thiothioside acceptor in a reaction for a time suitable to produce a first α(2→8) disialic acid with a SPh leaving group in the reducing end; then transferring this thiophenyl disialic acid to the dibutyl sialyl phosphate donor; and then adding a one or more disaccharides comprises α(2→9) disialic acid and optionally, a second α(2→8) disialic acid to the reaction mix and allowing a series of additional coupling reactions to produce one or more of α(2→8)/α(2→9) alternative tetra-, hexa-, octa-, or other polysialic acids.

In some aspects, the method comprises a programmable one-pot synthesis of oligosaccharides by: determining a relative reactive value (RRV) of a synthetic sialylated disaccharide; and programming a sequence for synthesis of a sialylated polysaccharide wherein the reactivity of a sialylated disaccharide is determined by the second reside of the disaccharide. The sialyl disaccharide building blocks comprise one or more of the group consisting of Neu5Acα(2→3)Gal, Neu5Acα(2→6)Gal, Neu5Acα(2→6)GalNAc, Neu5Acα(2→9)Neu5Ac, and Neu5Acα(2→8)Neu5Ac.

The method comprise assembling a library of sialosides using sialyl disaccharide building blocks comprises N-acetyl neuraminic acid (Neu5Ac). The library of sialosides comprise receptors of influenza virus hemagglutinin (HA) proteins. The method further comprises: immobilizing a plurality of members of the library of sialosides on an array.

The invention relates to a library comprising a plurality of sialyl polysaccharides, wherein the polysaccharides are synthesized from sialyl disaccharide building blocks generated by coupling the N-acetyl-5-N,4-O-carbonyl-protected dibutyl sialyl phosphate donor with a suitable acceptor.

In some aspects, the sialyl disaccharide building blocks comprise one or more of the group consisting of Neu5Acα(2→3)Gal, Neu5Acα(2→6)Gal, Neu5Acα(2→6)GalNAc, Neu5Acα(2→9)Neu5Ac, and Neu5Acα(2→8)Neu5Ac. One or more of the sialyl polysaccharides correspond to naturally occurring α(2→3) or α(2→6) sialosides. The sialyl polysaccharides bind to influenza virus hemagglutinin (HA) proteins. In some aspects, the sialyl polysaccharides bind to a pathogen, an infective agent, a cancer cell marker, a virus, a bacteria, or a fungus.

The invention relates to a method for detecting binding to a sialoside, the method comprising immobilizing a plurality of sialyl polysaccharides, wherein the polysaccharides are synthesized from sialyl disaccharide building blocks generated by coupling the N-acetyl-5-N,4-O-carbonyl-protected dibutyl sialyl phosphate donor with a suitable acceptor, at discrete sites on an array; contacting the array with a sample suspected of containing an agent that binds to a sialoside on the array; detecting a binding reaction of the array; and determining the presence or absence of the agent based on detecting a binding reaction on the array. In some aspects, the sialoside on the array comprises a glycan found on a cell surface receptor. In some aspects, the agent comprises a surface glycoprotein of a pathogen or active fragment thereof.

In some aspects, the agent comprises an influenza hemagglutinin protein or active fragment thereof. The influenza hemagglutinin protein or active fragment thereof comprises a natural virus. The influenza hemagglutinin protein or active fragment thereof comprises a recombinant HA protein, polypeptide or active variant thereof.

In some aspects, the array comprises α(2→3) and α(2→6) sialosides of varying lengths. The binding pattern on the array is distinctive of a strain of influenza virus. The strain of influenza virus is selected from the group consisting of H1N1, H3N1, H3N2, H5N1, H5N2, H7N7, and H9N2. The binding profile the HA protein or fragment from a strain of influenza virus is dependent on the sequence or length of α(2→3) and α(2→6) silosidesi. In some aspects, the strain of influenza virus is selected from the group consisting of pandemic Cal/09 H1N1, seasonal Brisbane/59/2007 (Br/59/07), H1N1/New Calcdonia/1999 (NC/99), Brisbane H3N1, and NIBRG-14 (H5N1), Br10 (H3N2), Cal07 (H1N1) H5 (Vietnam 1194/2004 and CHA5), WSN (H1N1) 1933, and A/Puerto Rico/8/34 (H1N1): PR8 strain influenza virus.

BRIEF DESCRIPTION OF THE DRAWINGS

The following drawings of schemes and figures form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 6 shows $K_D$ of influenza HA from SOV and Seasonal flu towards α2,6-sialosides.

FIGS. 7-1 and 7-2 show sialosides on the array and the $K_D$ values (nM) of HA glycosylation mutants for individual sialosides.

FIG. 9 shows Scheme 2 showing One-Pot Synthesis of Influenza HA Receptors α(2→3) and α(2→6)-Linked Trisaccharides and DSGG Epitope Tetrasaccharide. Reagents and Conditions: (a) 6a (1.5 equiv), 4Å MS, TMSOTf (1.5 equiv), −78° C., CH2Cl2; (b) −78° C. →−40° C. (c) NIS (1.2 equiv), overall 80% for 28, α only; 79% for 29, α only; 57% for 30, α only.

FIG.

DETAILED DESCRIPTION OF THE INVENTION

Figure 1A:
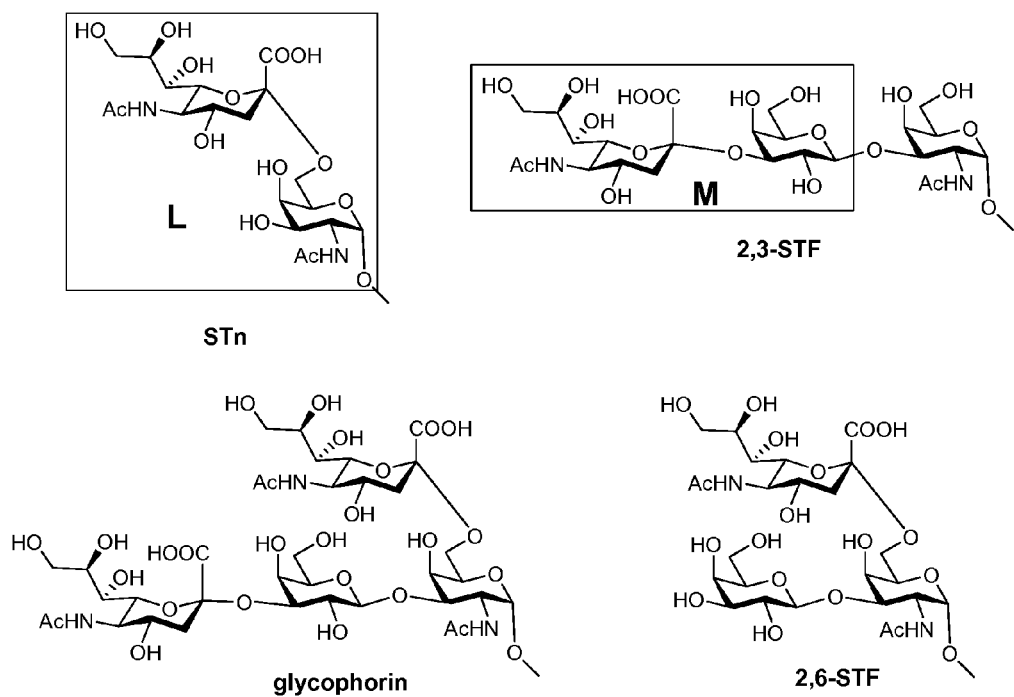
FIG. 1A shows the structures of Sialylated O-glycans STn, 2,3- STF, Glycophorin, and 2,6-STF.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, structural, functional, and other changes may be made without departing from the scope of the present disclosure. The following detailed description is, therefore, not to be taken in a limiting sense.

The specification discloses an efficient method for the synthesis of a sialyl phosphate donor from sialyl thioglycoside and its use for the preparation of stereochemically defined disaccharide building blocks, including Neu5Acα(2→3)Gal, Neu5Acα(2→6)Gal, Neu5Acα(2→6)GalNAc, Neu5Acα(2→9)Neu5Ac, and Neu5Acα(2→8)Neu5Ac, which were subsequently used for the efficient synthesis of α(2→3) and α-linked sialosides, including receptors of hemagglutinins, renal cell carcinoma associated antigen DSGG epitope tetrasaccharide, stage-specific embryonic antigen-4 (SSEA-4), and oligosialic acids. This new sialyl donor and sialyl disaccharide building blocks were further used in the assembly of a library of sialosides, which was then used to prepare a glycan array to study the real influenza virus binding profile and the effect of hemagglutinin (HA) glycosylation on its interaction with sialoside acceptors.

N-Acetyl Sialyl Dibutyl Phosphate Donor.

As previously described, the preparation of sialyl phosphate donors came from the oxidation of corresponding sialyl phosphite.[7a,7d] Unfortunately, poor efficiency was observed when these phosphate compounds were investigated as sialyl donors, which resulted in low yield and diminished α-selectivity.[7a,7d] On the other hand, in contrast to the sialyl phosphate donor, other glycosyl phosphate donors such as that of fucose, mannose, galactose, glucose and glucosamine have been used in the construction of O-glycosides[24] and C-glycosides,[25] and especially in the automated solid-phase synthesis of oligosaccharides.[18,26] Because phosphate-based leaving groups can be selectively activated in the presence of thioglycoside, it is desirable to explore the synthesis and utility of sialyl phosphate donor. Surprisingly, dibutyl sialyl phosphate 2 can be synthesized in high yield (94%) by treatment of thiosialoside donor 1 and commercially available dibutyl phosphate in the presence of N-iodosuccinimide and catalytic trifluoromethanesulfonic (triflic) acid (NIS/cat. TfOH) at 0° C. in CH$_2$Cl$_2$ (Table 1, entry 1-2). The reaction was complete in 5 h to give a mixture of α- and β-anomers. The sialyl α-phosphate 2a and sialyl β-phosphate 2b can be easily separated by silica gel column chromatography and are both stable at −20° C. for several months.

TABLE 1

Synthesis of N-acetyl, N-TFA, N-acetyl-5N,4O-Carbonyl Protected Sialyl Phosphate Donors.

Thiosialoside $\xrightarrow[\text{CH}_2\text{Cl}_2, 4\text{Å MS}, 4°\text{C.}]{\text{HOPO(OBu)}_2, \text{NIS, TfOH}}$ Sialyl phosphate

| Entry | Thiosialoside | Product | Yield[a] | α:β[b] |
|---|---|---|---|---|
| 1 | 1a | 2 (α = 2a, β = 2b) | 89% | 1.5:1 |

TABLE 1-continued

Synthesis of N-acetyl, N-TFA, N-acetyl-5N,4O-Carbonyl Protected Sialyl Phosphate Donors.

$$\text{Thiosialoside} \xrightarrow[\substack{\text{NIS, TfOH} \\ \text{CH}_2\text{Cl}_2, 4\text{Å MS,} \\ 4°\text{ C.}}]{\text{HOPO(OBu)}_2} \text{Sialyl phosphate}$$

| Entry | Thiosialoside | Product | Yield[a] | α:β[b] |
|---|---|---|---|---|
| 2 | 1b | 2<br>α = 2a<br>β = 2b | 94% | 1.2:1 |
| 3 | 3a | 4<br>α = 4a<br>β = 4b | 98% | 1.4:1 |
| 4 | 3b | 4<br>α = 4a<br>β = 4b | 91% | 1.1:1 |
| 5 | 5a | 6<br>α = 6a<br>β = 6b | 94% | 10:1 |
| 6 | 5b | 6<br>α = 6a<br>β = 6b | 96% | 3:1 |

[a] Isolated yield.
[b] Determined by $^1$H NMR analysis of the reaction mixture The glycosyl donor properties of sialyl α-phosphate 2a were initially tested by coupling with galactopyranoside acceptor 7[23] bearing a free OH group at position 6 and a thiocresol leaving group (Table 2). To a stiffing mixture of 2a (1.5 equiv), 7 (1.0 equiv) and 4 Å MS in CH$_3$CN at −40° C. under argon, was added trimethylsilyl trifluoromethanesulfonate (TMSOTf; 1.5 equiv). The reaction was complete in 5 min, and the glycosylation product 8 was obtained in 74% yield with α/β ratio of 5:1 (entry 1). Next, the glycosylation of sialyl β-phosphate 2b and acceptor 7 was also evaluated under the same reaction condition. However, when one equivalent of TMSOTf was used, a portion of β-phosphate 2b was not activated even with a prolonged reaction time. After addition of another equivalent of TMSOTf, the β-phosphate donor 2b was completely consumed and produced the desired disaccharide 8 in 75% yield, albeit with a slight decrease in α-selectivity (entry 2). These results are consistent with the fact that the equatorial glycosyl donor is more reactive than their axial counterpart.[24f]

TABLE 2

Glycosylation of N-Acetyl, N-TFA, N-acetyl-5N,4O-Carbonyl Protected Sialyl Phosphate Donors.

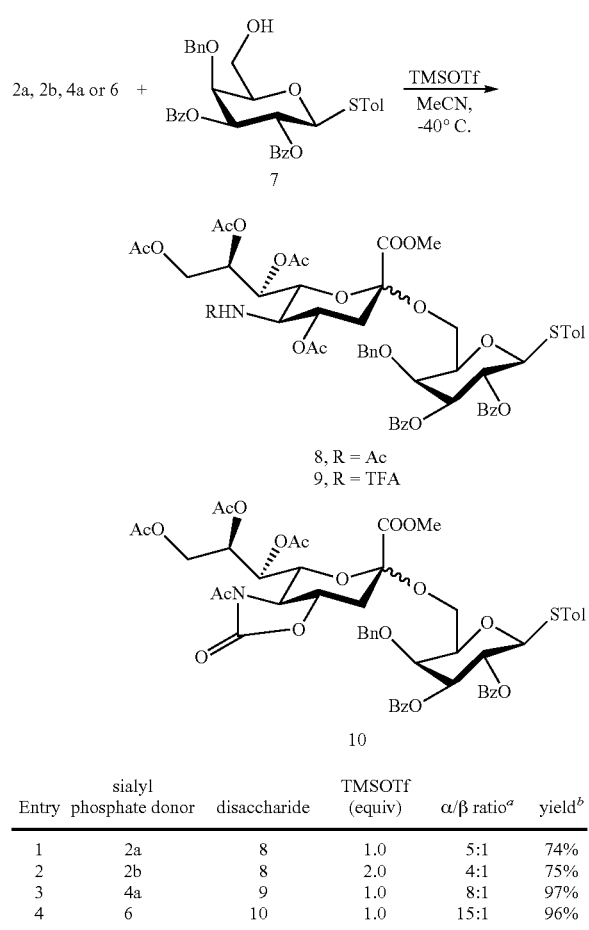

| Entry | sialyl phosphate donor | disaccharide | TMSOTf (equiv) | α/β ratio[a] | yield[b] |
|---|---|---|---|---|---|
| 1 | 2a | 8 | 1.0 | 5:1 | 74% |
| 2 | 2b | 8 | 2.0 | 4:1 | 75% |
| 3 | 4a | 9 | 1.0 | 8:1 | 97% |
| 4 | 6 | 10 | 1.0 | 15:1 | 96% |

[a]Isolated yield.
[b]Determined by $^1$H NMR analysis of the reaction mixture

N-Trifluoroacetyl and N-Acetyl-5-N,4-O-Carbonyl Protected Sialyl Dibutyl Phosphate Donors.

It has been reported that replacement of the C-5 acetamido group of sialyl phosphate with the azide[14a] or trifluoroacetamido[14b] group greatly enhanced both α-selec-tivity and reactivity. Using this strategy, the inventors synthesized N-TFA sialyl phosphate 4 from the thiosialoside 3[15b] under above-mentioned conditions (Table 1, entry 3-4). For comparison with 2a, α-4a and β-4b anomers were separated and acceptor 7 was glycosylated with 4a under TMSOTf promotion at −40° C. in MeCN. The results indeed showed much improved yield (97%) and α-selectivity (α/β ratio of 8:1) (Table 2, entry 3). Since thiosialosides with N-acetyl-5-N,4-O-carbonyl[27] or 5-N,4-O-carbonyl[28] protections were shown to give high α-selectivity and excellent yields toward different acceptors, the inventors decided to test a new sialyl phosphate donor with N-acetyl-5-N,4-O-carbonyl protection because the oxazolidinone group could be cleaved under mild conditions leaving the acetamide intact.[27a] Compound 5 was transformed to dibutyl phosphate donor 6 in almost quantitative yield (Table 1, entry 5-6); the αanomer of thiosialoside gave more α phosphate product (Table 1, entry 1-4).

Compound 6, without separation of the α,β-mixture, was coupled to acceptor 7 under TMSOTf promotion in CH$_3$CN at −40° C. to give the disaccharide 10 with very high yield (96%) and markedly improved α-selectivity (α/β ratio of 15:1) (Table 2, entry 4). The inventors also observed that the N-acetyl-5-N,4-O-carbonyl protection enhanced the reactivity of 6, as the α and β-phosphate mixture was completely activated with only one equivalent of TMSOTf.

Effects of Leaving Groups and Solvent Systems on the α-Selectivity of N-Acetyl-5N,4O-Carbonyl Protected Sialyl Donors.

To study the influence of different leaving groups on the N-acetyl-5N,4O-carbonyl protected sialyl phosphate donor 6 and its tolylthio and phenylthio counterparts, 5 and 5c[27a] were examined by coupling with the primary hydroxyl of glucose acceptor 11 in CH$_2$Cl$_2$ at −40° C. (Table 3). From the results in Table 3, phosphate donor 6 showed a higher α-selectivity (entry 3) than 5 (entry 1) and 5c (entry 2). In addition, only 5 min are required for the completion of reaction compared to 30 min and 2 h for 5 and 5c, respectively. Next, in order to know the effect of solvent on the glycosyl donor properties of phosphate donor 6, the inventors tested its reaction with acceptor 11 in MeCN and CH$_2$Cl$_2$, respectively (entry 3 and 4), and it was found that when the solvent was changed from MeCN to CH$_2$Cl$_2$, the yield was improved from 80% to 92% and the α/β ratio was also greatly improved from 7:1 to 13:1. Nitrile effect was not observed in this case. In short, these results showed that conversion of the sulfide leaving group of 6 to dibutyl phosphate enhanced the α-selectivity and reactivity.

TABLE 3

Comparison of Glycosylation Using N-acetyl-5-N,4-O-Carbonyl Protected Sialic Acid Donors with Thiophenyl, Thiocresol, and Dibutyl Phosphate Leaving Groups

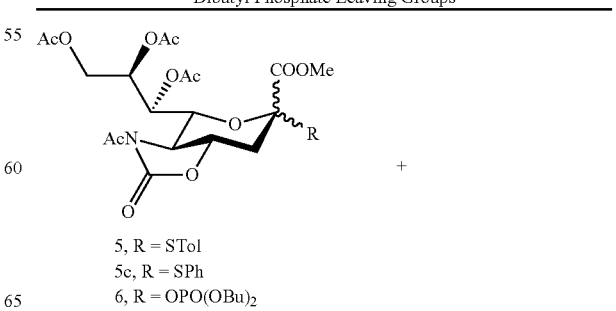

5, R = STol
5c, R = SPh
6, R = OPO(OBu)$_2$

TABLE 3-continued

[Structure of compound 11: HO, BnO, BnO, BnO, OMe galactoside]

Promoter / CH₃CN or CH₂Cl₂, MS4A, -40° C. →

[Structure of compound 12: sialyl-galactose disaccharide with AcO, AcO, OAc, AcN, COOMe, BnO, BnO, OMe groups]

| Entry | Donor[a] | Solvent | Promoter[b] | Time | Yield[c] | α/β ratio[d] |
|---|---|---|---|---|---|---|
| 1 | 5 | CH₂Cl₂ | NIS/TfOH | 30 min | 92% | 3.3:1 |
| 2 | 5c | CH₂Cl₂ | NIS/TfOH | 2 h | 91% | 9.4:1 |
| 3 | 6 | CH₂Cl₂ | TMSOTf | 5 min | 92% | 13:1 |
| 4 | 6 | MeCN | TMSOTf | 5 min | 80% | 7:1 |

[a]Donor (1.3 equiv), acceptor (1.0 equiv);
[b]NIS (2.0 equiv), TfOH (1.0 equiv), TMSOTf (1.3 equiv); Glycosidation of 5 went slowly when a catalytic amount of TfOH was used;
[c]Isolated yield;
[d]Determined by ¹H NMR analysis of the reaction mixture α-Selective Synthesis of Neu5Acα(2→6)Gal and Neu5Acα(2→3)Gal Disaccharide Building Blocks.

The inventors first focused our study on the identification of suitable acceptors for the α-selective synthesis of disaccharide building blocks with Neu5Acα(2→6)Gal linkage. In order to facilitate the formation of desired β linkage by utilizing neighboring group participation in the subsequent glycosylation, it was desirable to install the benzoyl ester group at C-2 of the galactose acceptors. To our surprise, glycosylation of 4,6-dihydroxy thiogalactoside acceptor 13[29] with sialyl phosphate donor 6a in the presence of TMSOTf (1 eq to donor) in CH₂Cl₂ at -78° C. gave Neu5Acα(2→6)Gal disaccharide 14 as a single α-product in 85% yield (table 4, entry 1). The a-configuration was confirmed by coupling constant of $^3J_{C1-Heq}$. The inventors then turned our attention to the synthesis of Neu5Acα(2→3)Gal disaccharide, which is more challenging because of the less reactive C-3 position of the galactose acceptor. At first, tolyl-4,6-benzylidine-1-thio-β-D-galactopyranoside 15[30] (table 4, entry 2) was used as the acceptor because better α-selectivity was previously demonstrated.[14d,31] Under TMSOTf promotion at -78° C. in CH₂Cl₂, glycosylation of acceptor 15 (1.5 equiv) with sialyl phosphate donor 6a (1.0 equiv) gave the major α-product 16 in 41%, along with 39% side product (compound 5) which was formed from an aglycon transfer reaction. To eliminate the aglycon transfer, the inventors introduced the electron withdrawing benzoyl group to C-2 of 15 to reduce the side reaction.[32] In addition, the benzoyl ester at the C-2 position should promote the β-selective glycosylation via neighboring group participation. Indeed, a high-yield (83%) and α-anomeric product was obtained when the modified tolyl-2-O-benzoyl-4,6-benzylidine-1-thio-β-D-galactopyranoside acceptor 17[8b] was used, with only 5% of transfer product (entry 3). This α(2→3)-linked disaccharide building block with a suitable leaving group at the anomeric center of galactose can be directly used in the next glycosylation without the need of protecting group manipulation.

TABLE 4

Results of Silylation by Using the N-acetyl-5-N,4-O-Carbonyl Protected Sialyl Phosphate 6a.

| Entry | Acceptor | Product |
|---|---|---|
| 1 | [Structure 13: HO, OH, BzO, BzO, STol galactoside] | [Structure 14: sialyl-galactose disaccharide with AcO, AcO, OAc, AcN, COOMe, HO, BzO, BzO, STol] |
| 2 | [Structure 15: Ph-benzylidene protected galactoside with HO, HO, STol] | [Structure 16: sialyl-galactose disaccharide with AcO, AcO, OAc, AcN, COOMe, OH, STol, Ph-benzylidene] |

TABLE 4-continued
Results of Silylation by Using the
N-acetyl-5-N,4-O-Carbonyl Protected Sialyl Phosphate 6a.
3 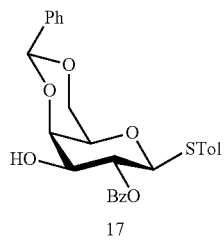 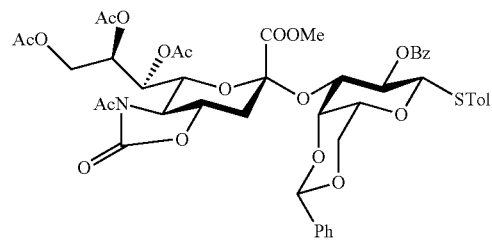
17, 18
4 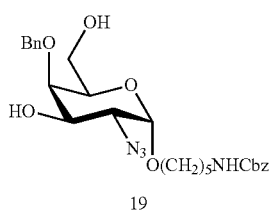 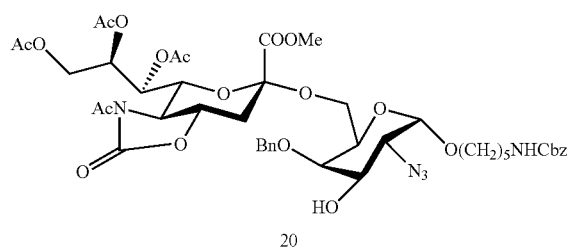
19, 20
5 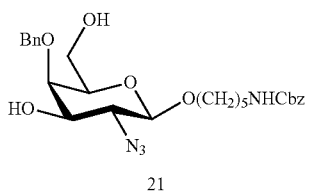 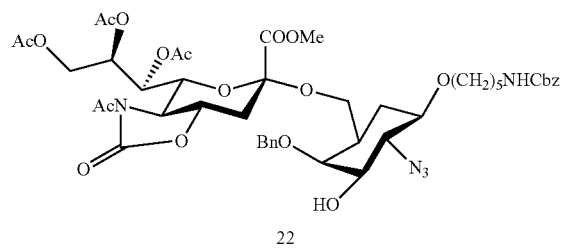
21, 22
6 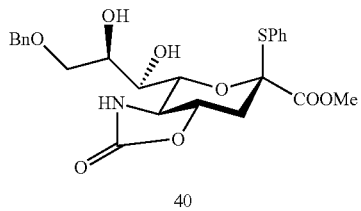 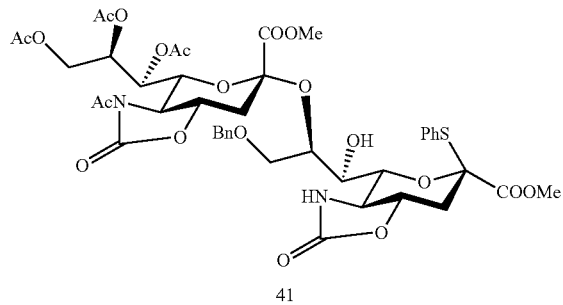
40, 41

TABLE 4-continued
Results of Silylation by Using the
N-acetyl-5-N,4-O-Carbonyl Protected Sialyl Phosphate 6a.
7
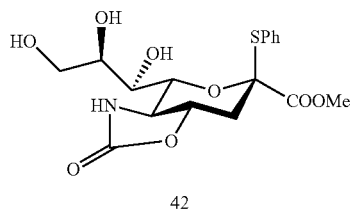
42
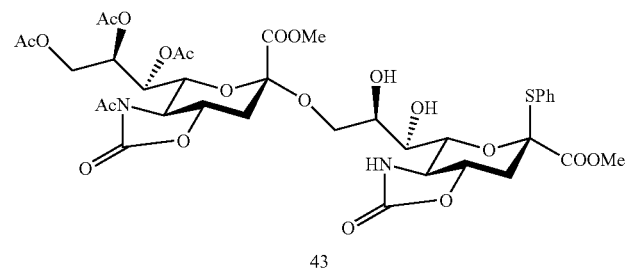
43
8
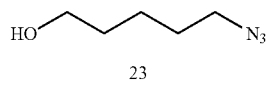
23
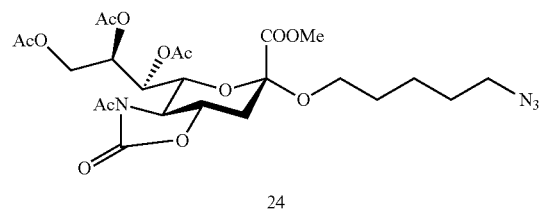
24
9
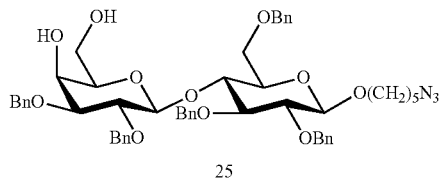
25
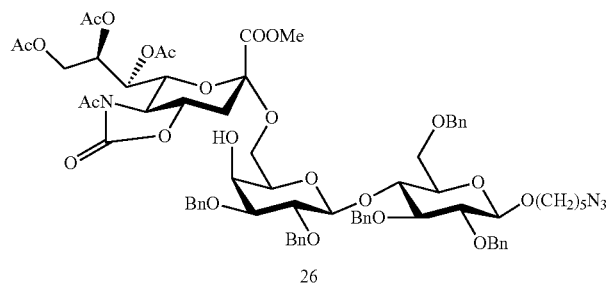
26
| Entry | Yield[a] | α:β ratio[b] | $\delta_{C1}$ (ppm) | $^3J_{C1\text{-}H3eq}$ (Hz) |
|---|---|---|---|---|
| 1 | 85 | α only | 168.4 | 5.7 |
| 2 | 41 | α only | 168.6 | 6.3 |
| 3 | 83 | α only | 168.9 | 5.5 |
| 4 | 71 | α only | 168.3 | 6.2 |
| 5 | 70 | α only | 168.3 | 6.0 |
| 6 | 67 | α only | 168.7 | 6.0 |
| 7 | 82 | α only | 168.5 | 6.0 |
| 8 | 91 | α only | 168.8 | 6.0 |
| 9 | 90 | α only | 168.3 | 6.4 |
[a]Isolated yield.
[b]Crude result.

The inventors also observed that the reactivity between 6a and 6b was not noticeable at −40° C. while the difference is notable at −78° C. To probe the differences of reactivity between α- and β-phosphates, the inventors then separated the mixture of 6a and 6b and coupled them with galactose acceptor 17, respectively (Table 5). In the presence of 1.0 equivalent of TMSOTf, β-phosphate 6b did not proceed to a complete activation until the temperature was increased to −50° C. (entry 2), whereas the α-phosphate donor was completely activated at −78° C. (entry 1). In both cases the yield of glycosylation product 18 is similar but the α-selectivity decreased in the case of β-phosphate 6b. The results showed that temperature is an important factor for controlling the α-selectivity of sialylation with sialyl phosphate donor 6. Moreover, the difference in reactivity between sialyl α-phosphate 6a and β-phosphate 6b is less than other glycosyl phosphates; for example, the galactosyl α-phosphate was only activated at temperature higher than −20° C., while galactosyl β-phosphate was easily activated at −78° C.[24f]

TABLE 5

Comparison of Reactivities between Sialyl
α-Phosphate 6a and Sialyl β-Phosphate 6b 6a or 6b + 17 →(TMSOTf, CH₂Cl₂, −78° C. or −50° C.)

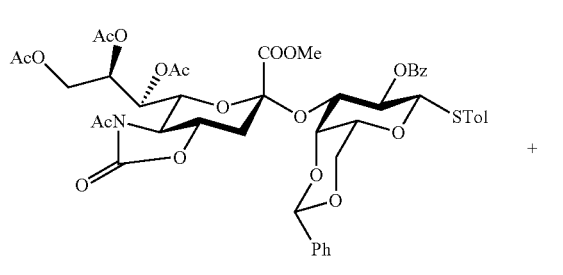

| Entry | Donor | Reaction time | T (° C.) | Yield[a] | 18:18b[b] |
|-------|-------|---------------|----------|----------|-----------|
| 1 | 6a | 5 min | −78° C. | 83% | 18 only |
| 2 | 6b | 5 min | −50° C. | 82% | 10:1 |

[a]Isolated yield.
[b]Determined by ¹H NMR analysis of the reaction mixture

α-Selective Synthesis of Neu5Acα(2→6)GalNAc Disaccharide Building Block.

Figure 1B:
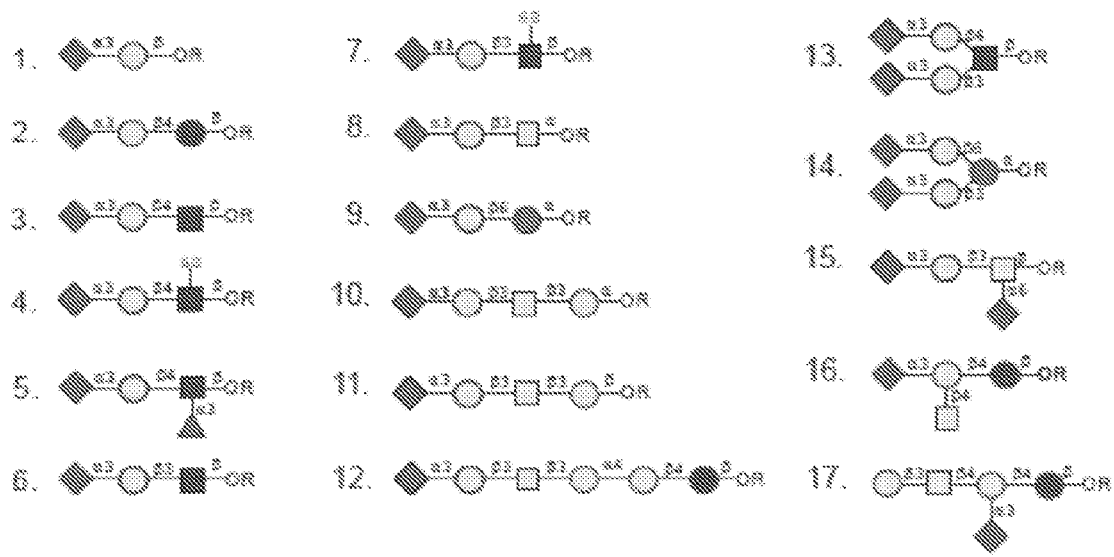
FIG. 1B shows sialosides structures that were spotted on glass slide to create a sialoside array for influenza HA binding studies.
Figure 1B:
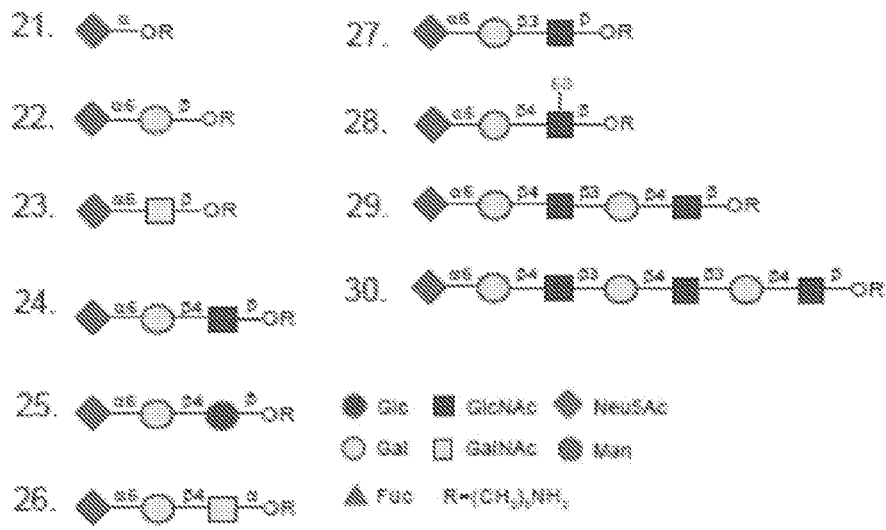

The sialylated versions of the O-glycan core structures Tn (GalNAcα(1→1)Ser/Thr) and TF (Galβ(1→3)GalNAcα(1→1)Ser/Thr) are highly expressed in many types of human tumors, including that of colon, breast, pancreas, ovary, and stomach.[33] Synthesis of O-linked sialylated antigens such as STn, 2,6-STF, 2,3-STF, and glycophorin (FIG. 1) is challenging because the sialylation reaction often gives α and β mixtures, and tedious separations are indispensable to get the desired α product.[34] After analysis of their structures, two building blocks L and M are essential (FIG. 1). Having accomplished the synthesis of NeuAcα(2→3)Gal building block M, the inventors are interested in the synthesis of NeuA5cα(2→6)GalNAc building block L. By using the concept of "cassette synthesis" as described previously,[34-35] the inventors synthesized the GalNAc acceptor 19 and 21 with C-3 and C-6 OH groups and attached spacer at the anomeric center via α and β linkages, respectively (Table 4, entry 4 and 5). Thus, after sialylation at 6-OH, the product would be directly elongated from the C-3 position without protecting group manipulation. Accordingly, sialylation of 19 (1.0 equiv) with sialyl α-phosphate donor 6a (1.0 equiv) at −78° C. afforded disaccharide 20 in 71% yield and only α-product was obtained, along with 13% of 3,6-disialylated trisaccharide and 9% of 2,3-elimination byproduct (Table 4, entry 4). Another sialylation using 21 as the acceptor, disaccharide 22 was achieved in 70% yield, along with 14% of 3,6-disialylated trisaccharide and 8% 2,3-elimination byproduct (Table 4, entry 5). This highly α-selective coupling reaction eliminated the time-consuming separation of stereoisomer. Most importantly, such disaccharide building blocks could be used as starting materials for the preparation of other O-linked sialylated antigens.

α-Stereoselective One-Pot Protocol.

Having successfully achieved the stereoselective synthesis of Neu5Acα(2→3)Gal, Neu5Acα(2→6)Gal and Neu5Acα(2→6)GalNAc disaccharides, the inventors directed our attention toward the development of a one-pot protocol for the convergent and α-selective synthesis of sialosides. Stepwise synthesis of Influenza virus binding trisaccharide 28 with the Neu5Acα(2→6)Gal linkage was investigated first (Scheme 1). After the synthesis of disaccharide 14 with 85% yield according to the aforementioned conditions, glycosylation of the C-4 OH of GlcNAc acceptor 27 was achieved in 77% yield under NIS/TMSOTf promotion, along with 16% of orthoester byproduct 35. The total yield of the two reactions is about 66%. At this stage, various promoters such as NIS/TfOH,[36] DMTST,[37] BSP/Tf₂O,[38] p-TolSCl[20c] were tested and NIS/TfOH gave the highest yield. As a result, the inventors selected NIS/TfOH as the promoter for the second glycosylation in the development of the one-pot protocol.

Next, a one-pot synthesis of trisaccharides 28 was examined (Scheme 2). Treatment of the first acceptor 13 (1.0 equiv) with sialyl α-phosphate donor 6a (1.5 equiv) under aforementioned conditions gave disaccharide 14. Next, adding second acceptor 27 without the need to add TfOH, the second coupling reaction proceeded within 30 min with the addition of only 1.2 equiv of NIS to provide trisaccharide 28 in excellent yield (80% based on second acceptor) and α-selectivity. A parallel study was done by the assembly of α(2→3)-linked trisaccharides 29. Also, an excellent yield and α-selectivity was obtained (79%). Notably, the overall reaction yield increased in these one-pot glycosylation reactions compared to the stepwise procedure, probably due to a lower amount of orthoester byproduct 35 found in these one-pot reactions, and moreover, isolation of intermediate disaccharides 14 and 18 was omitted. This is the first α-selective one-pot glycosylation of (2→6) and (2→3) sialylations. In addition, the renal cell carcinoma associated antigen DSGG[39] epitope tetrasaccharide 30 was also assembled by using the same one-pot protocol, in which Neu5Acα(2→6)GalNAc disaccharide 22 with C-3 hydroxyl was used as the second acceptor. Likewise, the reaction proceeded smoothly and afforded tetrasaccharide 30 in 57% yields with α-product. The decreased yield was due to the hydrolysis of glycosidic bond between GalNAc and the linker of disaccharide 22.

One-Pot Synthesis of Stage-Specific Embryonic Antigen-4 (SSEA-4, 31).

Monosialosyl globopentaosylceramide, SSEA-4, which functions as tumor-associated antigen[40] and bacterial or viral receptor[41] contains a Neu5Acα(2→3)Gal moiety at its non-reducing end. Although synthesis of SSEA-4 has been achieved by the group of Hasegawa[42] and Schmidt[43] via chemical method and the Huang[44] group via chemoenzymatic method, the protected hexasaccharide 32 can be more efficiently assembled here from sialyl phosphate 6a (1.5 eq), disaccharide 33 (1.0 eq.), and trisaccharide 34 (0.6 eq.) in a one-pot manner (scheme 3). This strategy used disaccharide 33 as the first acceptor in which the non-reducing galactoside possessed the same protecting groups as compound 17 in order to preserve the α-stereoselectivity upon sialylation. The trisaccharide 34 has been described by this group previously in which the difficult Galβ(1→4)Gal bond was installed in advance.[45]

Scheme 4 shows the procedure for the preparation of disaccharide 33. The 3-O-PMB-protected glycosyl donor 37 can be readily prepared from 35. Glycosylation of thioglycoside 38 by 37 produced the disaccharide 39 in 60% yield, and after removal of the p-methoxybenzyl group at C-3 by DDQ led to the disaccharide acceptor 33.

α-Selective Synthesis of Neu5Acα(2→8)Neu5Ac and Neu5Acα(2→9)Neu5Ac Disaccharide Building Blocks.

Neu5Acα(2→8)Neu5Ac and Neu5Acα(2→9)Neu5Ac dimers are units of linear polysialic acids which play important roles in biological functions on the cell surface[46]; Neu5Acα(2→8)Neu5Ac dimer is also an important constituent of gangliosides such as GD2, which is a well-known cancer antigen and has long been considered as an attractive target for vaccine design.[47] Development of an efficient procedure for the synthesis of the α(2→8) and α(2→9) disaccharide building blocks for the construction of more complex structures is valuable. Recently, Takahashi and co-workers reported that the coupling of an 5-N,4-O-carbonyl-protected sialic acid donor and an acceptor showed an excellent α-selectivity.[28a,28c] By using the related approach, stereochemically pure Neu5Acα(2→8)Neu5Ac was synthesized by coupling sialyl α-phosphate donor (1.0 equiv) 6a with 7,8-dihydroxy thiosialoside acceptor 40[28a] (1.0 equiv) under TMSOTf promotion at −78° C. (Table 4, entry 6)). It is noted that disaccharide 41 was decomposed easily when the reaction was quenched by addition of Et$_3$N (yield only 15%). On the other hand, using a mild base such as NaHCO$_3$ would not cause the problem and result in a better yield. Also, under the same condition, Neu5Acα(2→9)Neu5Ac 43 (Table 4, entry 7) was obtained in high yield by coupling 6a with 7,8,9-trihydroxy thiosialoside acceptor 42[27a]. For this reaction, the inventors only observed a single product on TLC plate when the reaction was finished. But after silica gel column chromatography, the yield was reduced due to the decomposition of some products into uncharacterized side products.

Synthesis of α(2→9) Tetrasialosides.

The inventors have previously reported an α-specific synthesis of α(2→9)-linked tri-sialic acid by using C5-azido sialyl phosphite as donor and C5-azido thiosialoside as acceptor to provide the α(2→9) disaccharide which was further sialylated by orthogonal glycosylation to give the trimer.[14a] However, the broad applicability of this method was limited due to the unstable properties of C5-azido sialyl phosphite compound. On the other hand, Lin and co-workers developed another synthetic strategy using C5-TFA sialyl phosphite donor and C5-TFA thiosialoside acceptor for the synthesis of α(2,9) oligosialic acid.[14b] After iterative sialylation, acetylation, thiocresol deprotection and phosphite formation, the pentasialoside was synthesized. However, the α-selectivity decreased when the sugar chain was elongated. Recently, Takahashi also reported an alternative method for α-specific synthesis of α(2→9) trisialoside[14e] or α(2→9) tetrasialoside[48] by using 5N,4O-carbonyl protected thiosialosides, The sequence of assembly was from the reducing end to the nonreducing end, and this strategy provided the opportunity to stereoselectively elongated the sugar chain one residue at a time with the product being directly used in the next glycosylation after selective deprotection of protecting group at C8 or C9 position.

Herein, the inventors developed an alternative strategy for the synthesis of α(2→9)-tetra- to sα(2→9)-octa-sialosides via 5N,4O-carbonyl protected sialyl phosphate donor. Owing to the reason mentioned above that the α(2→9)-disialoside 43 decomposed after silica gel chromatography, the inventors synthesized compound 45 from donor 44. The C7, C8, and C9 positions of 44 were protected by the chloroacetyl group which was previously shown to enhance the reactivity of sialic acid donor.[14e,48,49] The reaction went smoothly and produced disialoside product 47 as single α-isomer in 80% yield, and the problem of decomposition was not observed. The chloroacetyl groups of the α(2→9)-sialosides 47 at the C7, C8, and C9 were removed to afford 48 as the acceptor for the next glycosylation. In addition, the anomeric thiophenol of the acetylated disaccharide 49 was changed to dibutyl phosphate, to produce disaccharide 50 as the donor for the next glycosylation (Scheme 5). This conversion proceeded to completion in 3 days with 73% yield.

The disaccharides of 48 and 50 were coupled to form the α(2→9)-tetrasialoside derivative. Table 6 showed the results of glycosylation conducted in different reaction conditions. The highest yield was obtained when the CH$_2$Cl$_2$/CH$_3$CN co-solvent was used. Surprising, the inventors only detected the α-isomer in these reactions, and the major side product is the unconsumed acceptor which can be recovered for reuse. This is the first example that disialic acid donor produced α-only glycosylation product. The advantage of this method is that the product of α(2→9)-tetrasialoside derivative can be directly subject to similar derivations as above to synthesize α(2→9)-octasialoside.

TABLE 6
Synthesis of αa(2→9)-Tetrasialic Acid 51 at different conditions.
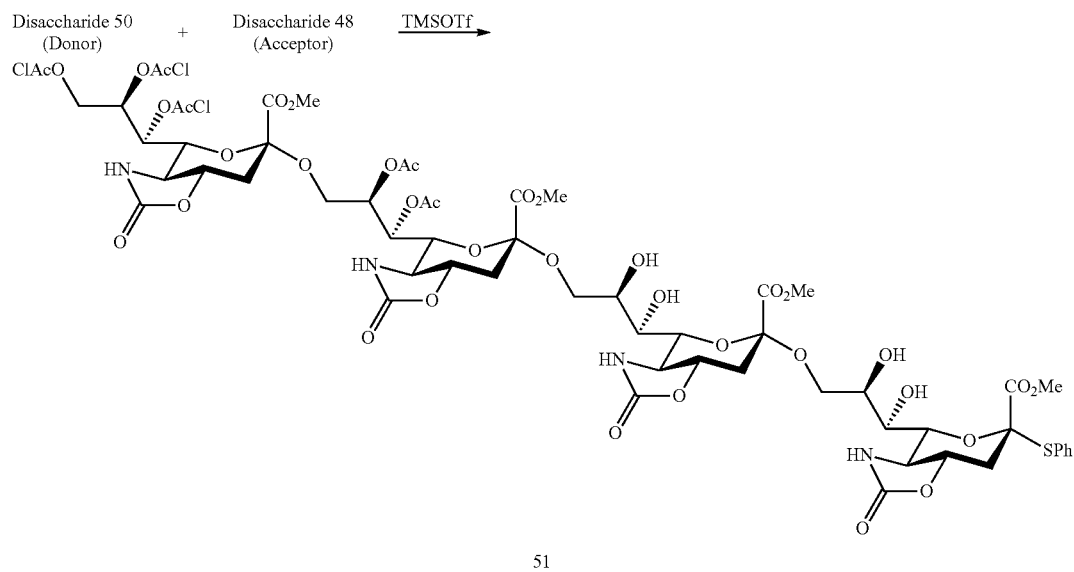

Disaccharide 50 (Donor) + Disaccharide 48 (Acceptor) TMSOTf

51

| Entry | Donor (equiv) | Acceptor (equiv) | Promoter (equiv) | Solvent | Temperature (° C.) | Time (hour) | Yield of 51 |
|---|---|---|---|---|---|---|---|
| 1 | 1.0 | 2.0 | 1.0 | $CH_2Cl_2/CH_3CN$ | −60 | 3 | 38 |
| 2 | 1.0 | 1.5 | 1.0 | $CH_3CN$ | −40 | 1 | n/d |
| 3 | 1.0 | 1.1 | 1.0 | $C_2H_5CN$ | −78 | 1 | — |
| 4 | 1.0 | 1.1 | 1.0 | $CH_2Cl_2/CH_3CN$ | −78 | 1.5 | 68 |
| 5 | 1.0 | 1.3 | 2.0 | $CH_2Cl_2/CH_3CN$ | −78 | 4 | 56 |
| 6 | 1.0 | 1.5 | 1.0 | $CH_2Cl_2$ | −78 | 2 | 38 |
Synthesis of α(2→9) Polysialic Acids as *Neisseria meningitidis* Vaccine Candidate.

Encouraged by the previous results, the inventors were interested in synthesis of longer polysialic acids as this type of glycans is an important vaccine target for *Neisseria meningitidis. Neisseria meningitidis* is a gram-negative *diplococcus* bacteria, which causes about 60% of the meningococcal diseases. Based on their surface antigens of capsular polysaccharide, *Neisseria meningitidis* can be classified into 13 serogroups. Among these 13 serogroups, A, B, C, Y, and W135 are the major pathogenic strains, while some recent reports indicated the rise of group X cases.[50] Group A is the main cause of epidemic diseases in the worldwide and often causes the large scale epidemics in developing countries of Asia and Africa by seasons.[51] Groups B and C frequently cause sporadic cases in industrial countries, such as United States of America and United Kingdom.[52] Moreover, the prevalence of group Y and W135 reveals the increasing tendency in North America and Saudi Arabia in the last few years.[50,53] The capsular polysaccharide plays an important role in the bacterial pathogenesis. The antiphagocytic properties help the bacteria to escape from the antibody and complement deposition.[54-56] However, because the capsular polysaccharide is the outermost shield of the bacteria, it has been considered to be the target antigen for vaccine design. The repeating unit structures of capsular polysaccharide of groups A, B, C, Y and W135 are shown in Table 7.

TABLE 7

Repeating unit structures of *N. meningitides* capsular polysaccharide of five major pathogenic strains.

| Serotypes of *Neisseria meningitidis* | Structures of capsular polysaccharide |
|---|---|
| Group A | →6)-α-D-ManpNAc(3/4OAc)-(1→OPO3→ |
| Group B | →8)-α-D-Neup5Ac-(2→ |
| Group C | →9)-α-D-Neup5Ac(7/8OAc)-(2→ |
| Group W135 | →6)-α-D-Galp-(1→4)-α-D-Neup5Ac(9OAc)-(2→ |
| Group Y | →6)-α-D-Glcp-(1→4)-α-D-Neup5Ac(9OAc)-(2→ |

To evaluate the functions of well-defined molecular vaccine against *N. meningitidis*. Synthesis of well-defined α(2→9) or α(2→8) polysialic acid based vaccines were a good model for vaccination study. The inventors used the convent [4+4] strategy to construct α(2→9) octasialic acid. The tetrasialic acid donor 52 and acceptor 53 can be synthesized in similar way that be used to construct disialic acid donor 50 and acceptor 48. The detailed procedures and yield are shown in Scheme 6.

For conjugation of polysailic acid to the carrier protein purpose, the inventors conjugated an azido alkyl pentyl group in the reducing end, and then elongate the length of sialic acid by using the previous mentioned methods. The inventors have synthesized di-, tri-, tetra-, hexa-, octa-sialic acid compounds with an azido alkyl pentyl group in the reducing end (Scheme 7).

Synthesis of α(2→8)/α(2→9) Alternative Polysialic Acids.

Compare to α(2→9) polysialic acids, chemical synthesis of α(2→8)/α(2→9) alternative polysialic acids was more challenging as it is very difficult to purify this type of glycans from nature. The inventors used chemical synthesis to tackle this problem. First, the inventors used the same sialyl phosphate donor 45 and acceptor 63 to synthesize α(2→8) disialic acid 64 in 83% with α/β=13:1. The α-product can be purified by silica gel chromatography. Similar to the previous mentioned methods. Compound 64 can be changed to phosphate donor 65 and disialic acid acceptor 66 in 78% and 84% yield, respectively. By using the similar glycosylation procedures, α(2→8)/α(2→9) alternative tetra-, hexa-, and octasialic acid can be obtained in a only products. Their detailed procedure, condition and yields are shown in Scheme 8.

Assignment of Anomeric Configuration.

The anomeric configuration of the resulting sialosides was determined by analysis of $^1$H NMR spectra based on the chemical shift of the H-3 eq group (α-glycosides are more downfield than β-glycosides), the H-4 signals (β-glycosides are more downfield than α-glycosides), the coupling constant $J_{7,8}$, (α-glycosides are larger than β-glycosides), the value of Δδ(H-9′–H-9) (α-glycosides: Δδ~0.2 ppm, β-glycosides: Δδ>0.3) (Table 8),[14a,35a,57] and $^3J_{C1\text{-}H3ax}$ coupling constants (α-glycosides>5 Hz, β-glycosides<1 Hz) (Table 4).[27a,58]

TABLE 8

Partial $^1$H NMR Analysis for Determination of Anomeric Configuration

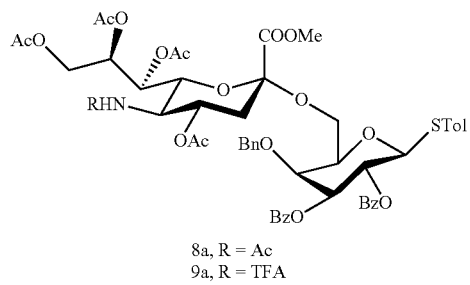

8a, R = Ac
9a, R = TFA

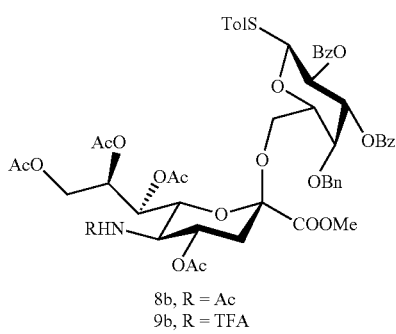

8b, R = Ac
9b, R = TFA

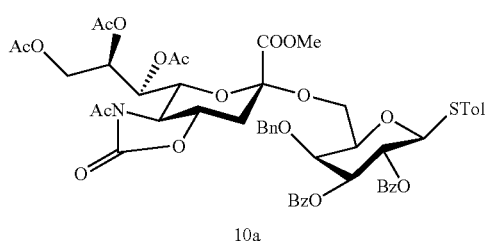

10a

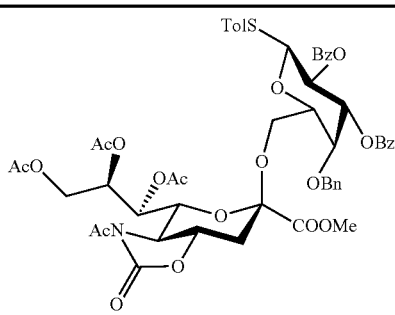

10b

| Compound | $δ_{H3eq}$ | $δ_{H4}$ | $J_{7,8}$ | Δδ|H9′-H9| |
|---|---|---|---|---|
| 2a | 2.68 | 4.97 | 7.8 | 0.24 |
| 2b | 2.60 | 5.26 | n | 0.34 |
| 4a | 2.73 | 5.13 | 8.0 | 0.18 |
| 4b | 2.61 | 5.51 | 2.5 | 0.31 |
| 6a | 2.98 | 4.15 | 7.5 | n |
| 6b | 2.86 | 4.54 | 4.3 | 0.39 |
| 8a | 2.58 | 4.86 | 8.5 | 0.26 |
| 8b | 2.28 | 4.76 | n | 0.61 |
| 9a | 2.62 | 5.00 | 8.0 | 0.20 |
| 9b | 2.36 | 4.85 | 5.6 | 0.58 |
| 10a | 2.85 | 3.99 | 7.6 | 0.33 |
| 10b | 2.69 | 4.20 | 3.2 | 0.61 |

Programmable One-Pot Synthesis Based on Relative Reactivity Values (RRVs).

The basic concept of programmable one-pot approach is that an oligosaccharide is assembled from the nonreducing end to the reducing end with the most reactive building block being added first.[8b,17] Thus, due to the fact that sialic acid is often found at the nonreducing end, synthesis of sialosides by this one-pot protocol requires the use of sialic acid building block as the first component. However, sialic acid thioglycosides are much less reactive and less influenced by the protecting groups than other thioglycosides. To solve this problem, the inventors use sialylated disaccharides as building blocks in our programmable one-pot synthesis as the reactivity of the sialylated disaccharides is determined by the second residue. The inventors first measured the RRVs of the synthesized sialylated disaccharides 10a, 14, and 18, using the HPLC method described previously (Table 8).[8b] Disaccharide 18 showed the highest reactivity among the three building blocks. Compound 10a with the extra C-4 O-benzylation is 1.7-fold more reactive than 14. In general, sialylation of a thioglycoside such as 17 has only slightly deactivated the anomeric reactivity of 17.

TABLE 9

Relative Reactivity Values of Sialylated Disaccharides

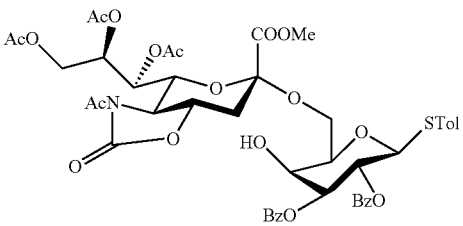

14 (127)

TABLE 9-continued

Relative Reactivity Values of Sialylated Disaccharides 10a (218)

18 (1462)

17 (1791)

To demonstrate the synthetic application of sialylated disaccharides as building blocks, the inventors conducted a representative reactivity-based one-pot synthesis of the sialylated pentasaccharide 75 using the three building blocks shown in Scheme 9. The overall yield of the one-pot synthesis was 48%, revealing that the sialylated disaccharides can be used as building blocks for the programmable one-pot synthesis of oligosaccharides with Neu5Ac as terminal residue.

Table 9 summarizes the results of glycosylation using various sialic acid donors with different leaving groups and C5-modifications. The inventors selected the acceptors that are frequently used for direct comparison. Two glycosylation results, one with primary and the other with secondary acceptors, were included for every sialyl donor. Generally, the yields of sialylation by using donors with different leaving groups (entry 1-10) did not exceed 70%, and a higher α-selectivity was obtained when a less hindered glycosyl acceptor was used (entry 2, 5, 6, and 8). Also, most of these reactions need to be conducted in acetonitrile. A second type of sialic acid donor is with C5-modification, which often greatly enhanced not only the α-selectivity but also the yield toward primary or secondary acceptors (entry 11-21). After comparing the glycosylation results of N-modified donors by coupling with primary acceptor II (entry 11-13 and 17-20), 5-N,4-O-oxazolidinone protected donors showed the best result (entry 17-20). On the other hand, for less hindered secondary acceptor XIV (entry 11, 12, and 17), the N,N-diacetyl sialyl donor gave the best outcome. In addition, for more hindered secondary acceptor XV (entry 13, 18, 19, and 20), N-TFA sialyl donor seems to be a good choice, and conversion of the leaving group to the admantanylthio group of N-acetyl-5-N,4-O-oxazolidinone protected donor showed further improvement (entry 20). Next, more improvement was achieved by using a combination of C-5 modification and efficient leaving group (entry 15 and 16). The products gave excellent α-selectivity and yield toward both primary and secondary alcohols. The N-acetyl-5-N,4-O-oxazolidinone protected donor indeed showed an excellent α-selectivity as well as high yield toward both primary and secondary acceptors, and the phosphate leaving group appears to be an excellent choice (entry 21).

TABLE 9

Review of Sialic Acid Donors with Different Leaving Groups and C-5 modifications

| Entry | Donor | Acceptor | Yield (%) α | Yield (%) β | Promoter | Solvent[a] | Ref |
|---|---|---|---|---|---|---|---|
| 1 | R = Cl | I (1°) | 67 | 0 | Ag$_2$CO$_3$ | e | 6c |
|   |        | X (2°) | 6 | 9 | Hg(CN)$_2$/HgBr$_2$ | f | 57c |
| 2 | R = OP(OBn)$_2$ | II (1°) | 67 | 13 | TMSOTf | a | 7a |
|   |        | XI (2°) | 67 | 11 | TMSOTf | a | 7a |
| 3 | R = OP(OEt)$_2$ | II (1°) | 56 | 14 | TMSOTf | a | 7c |
|   |        | XII (2°) | 55 |  | TMSOTf | a | 7c |
| 4 | R = (dithiocarbonate) | III (1°) | 48 | 16 | DMTST | a | 9a |
|   |        | XIII (2°) | 70 | 4 | PhSOTf | c | 9b |
| 5 | R = SMe | IV (1°) | 70 | 0 | DMTST | a | 59 |
|   |        | XIV (2°) | 52 | 0 | DMTST | a | 59 |
| 6 | R = SPh | II (1°) | 47 | 8 | NIS/TfOH | a | 35a |
|   |        | XIV (2°) | 70 | 0 | NIS/TfOH | a | 36 |

TABLE 9-continued

Review of Sialic Acid Donors with Different Leaving Groups and C-5 modifications

| Entry | Donor | Acceptor | Yield (%) α | Yield (%) β | Promoter | Solvent[a] | Ref |
|---|---|---|---|---|---|---|---|
| 7 | R = (N-Ph, O, CF3 imidate) | II (1°) | 69 | 10 | TMSOTf | c | 10a |
|   |   | XV (2°) | 61 | 20 | TMSOTf | c | 10a |
| 8 | R = SBox | I (1°) | 60 | 30 | MeOTf | a | 8d |
|   |   | XIV (2°) | 71 | 4 | MeOTf | a | 8d |
| 9 | R = OPO(OBn)$_2$ | II (1°) | 26 | 9 | TMSOTf | a | 7a |
| 10 | R = OPO(OEt)$_2$ | XII (2°) | 11 | 11 | TMSOTf | a | 7d |

[Structure: sialic acid donor with AcO, OAc, OAc, OAc, X, Y, COOMe]

| 11 | X = NAc$_2$, Y = SPh | II (1°) | 40 | 25 | NIS/TfOH | a | 35a |
|   | X = NAc$_2$, Y = SMe | XIV (2°) | 72 |  | NIS/TfOH | a | 60 |
| 12 | X = NHTroc, Y = SPh | II (1°) | 81 | 10 | NIS/TfOH | a | 35a |
|   |   | XIV (2°) | 35 | 8 | NIS/TfOH | a | 61 |
| 13 | X = NHTFA, Y = SPh | II (1°) | 85 | 7 | NIS/TfOH | a | 35a |
|   | X = NHTFA, Y = SMe | XVI (2°) | 84 | 0 | NIS/TfOH | a | 62 |
| 14 | X = N$_3$, Y = STol | V (1°) | 65 | 0 | NIS/TfOH | a | 14a |
| 15 | X = NPhth, Y = (N-Ph, O, CF3 imidate) | VII (1°) | 92 | 0 | TMSOTf | d | 14c |
|   |   | XVII (2°) | 74 | 2 | TMSOTf | d | 14c |
| 16 | X = TCA, Y = (N-Ph, O, CF3 imidate) | VIII (1°) | 77 | 0 | TMSOTf | c | 14d |
|   |   | XVIII (2°) | 68 | 0 | TMSOTf | c | 14d |

[Structure: sialic acid donor with oxazolidinone ring, AcO, OAc, OAc, X-N, Y, COOMe]

| 17 | X = H, Y = SPh | II (1°) | 100 | 0 | NIS/TfOH | b | 28a |
|   |   | XIV (2°) | 50 | 0 | NIS/TfOH | a | 28b |
| 18 | X = Ac, Y = SPh | II (1°) | 92 | 0 | NIS/TfOH | b | 27a |
|   |   | XVI (2°) | 10 | 75 | NIS/TfOH | b | 27a |
| 19 | X = Ac, Y = STol | II (1°) | 72 | 18 | NIS/TfOH | b | 27c |
|   |   | XVI (2°) | 44 | 37 | NIS/TfOH | c | 27c |
| 20 | X = Ac, Y = S-adamantyl | II (1°) | 91 | 0 | NIS/TfOH | b | 27b |
|   |   | XVI (2°) | 64 | 21 | NIS/TfOH | c | 27b |
| 21 | X = Ac, Y = OPO(OBu)$_2$ (present disclosure) | IX | 85 | 0 | TMSOTf | b |  |
|   |   | XIX | 83 | 0 | TMSOTf | b |  |

[a]Solvents: a = MeCN; b = CH$_2$Cl$_2$; c = MeCN + CH$_2$Cl$_2$; d = EtCN; e = CHCl$_3$; f = Cl(CH$_2$)$_2$Cl

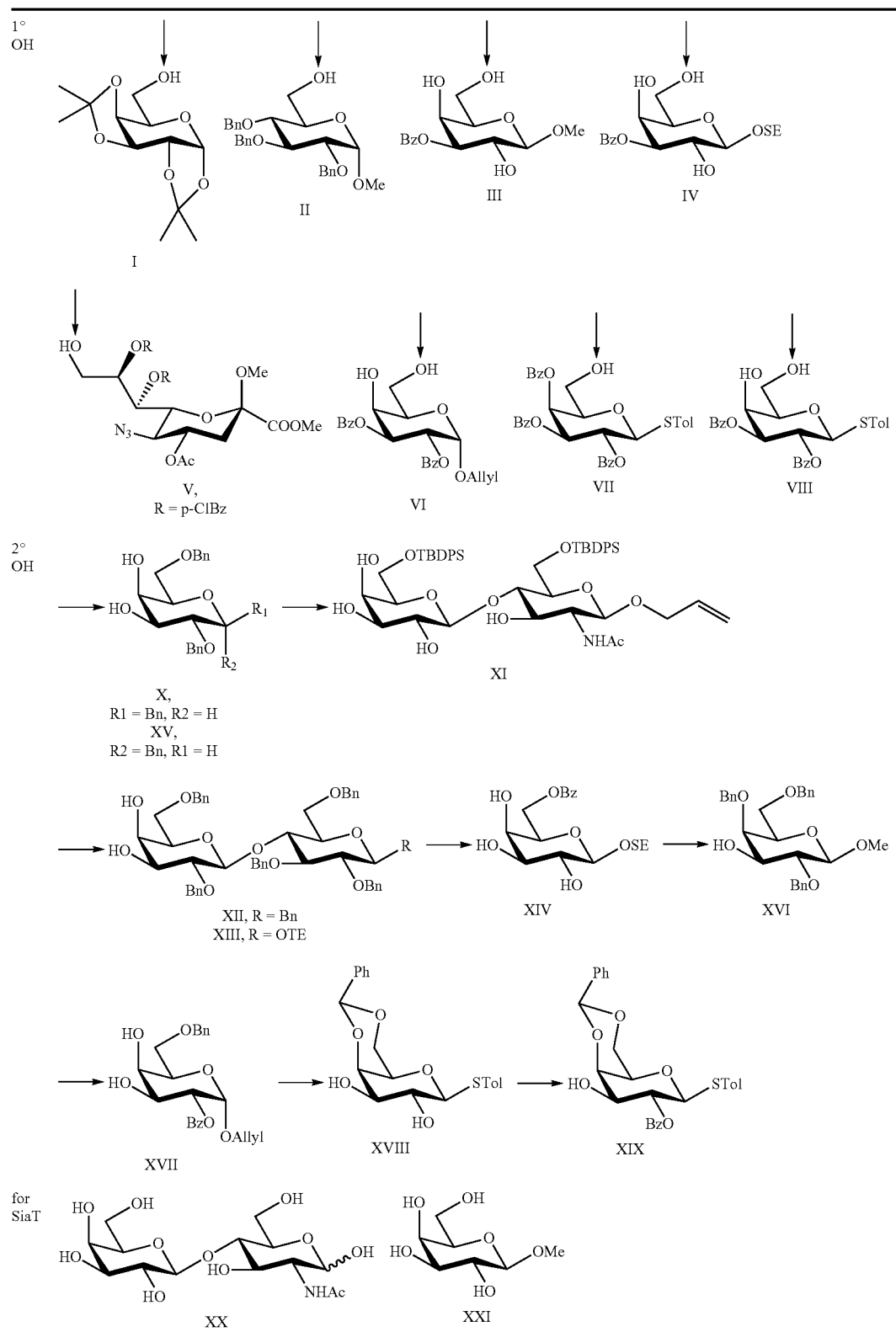

The concept of orthogonal glycosylation strategy involves condensing glycosyl donors with different types of leaving groups, so the resulting products can be directly used in the next glycosylation without anomeric leaving group adjustments. Most of orthogonal glycosylations employ thioglycosides as one of the reaction partners.[63] The orthogonal strategy is suitable for convergent synthesis of sialosides because it allows coupling of building blocks independent of their relative reactivity. As summarized in Table 9, different kinds of C-5 modifications all greatly enhanced sialic acid donor properties. For this reason, the development of C5-modified sialyl donors that can be used in orthogonal glycosylation would be beneficial. Since dibutyl sialyl phosphate is relatively easier to prepare and more stable than that of sialyl phosphite, it is a better choice for orthogonal synthesis.

Another advantage of the phosphate-based methodology includes the use of tolylthio glycosides as acceptors with defined relative relativity values (RRVs) for sialylation to give sialyl disaccharides as building blocks for the subsequent reactivity-based programmable one-pot synthesis. In this way, the limitation of relatively low reactivity of thiosialoside donor and the difficult control of stereoselectivity of sialylation could be resolved. Moreover, the RRVs of sialylated disaccharides can be programmed by manipulating the protecting groups of the second sugar residue at the reducing end.

Sialosides Array for Differential Sialyl Sugar Binding Activities of Influenza Hemagglutinins and Real Influenza Virus.

Pandemic influenza outbreaks pose a significant threat to public health as highlighted by the recent emergence of highly pathogenic avian influenza H5N1[64] and the latest outbreaks in 2009 of swine-oriented H1N1 viruses (2009 H1N1).[65,66] Influenza virus infection is initiated by virus attachment to cell receptors via influenza hemagglutinin (HA). The binding of HA is then followed by neuraminidase cleavage of the terminal sialic acid on receptors, and receptor-mediated endocytosis accompanied by pH-induced conformational changes of HA to lead to virus-cell membrane fusion, allowing the virus to enter the cells for virus replication.[67]

Influenza HA is a glycoprotein that forms trimers on the virus surface.[68] In contrast to protein-protein interactions, the binding of HA to cell receptors is dominated by protein-oligosaccharide interactions mediated by the N-acetyl neuraminic acid (Neu5Ac), the most abundant derivative of sialic acid found at the terminal end of glycoproteins or glycolipids on the cell surface.[69] Extensive studies of various influenza virus subtypes as well as recombinant HAs have established a correlation of sialoside binding preferences with species origins: α(2→6) linkage to galactose is preferred by HA from human isolates, α(2→3) linkage by HA from avian isolates, and both α(2→6) and α(2→3) linkage to galactose or glucose can be bound by HA from swine viruses.[70-74] It is generally believed that acquirement of α(2→6) sialosides recognition ability of an influenza virus is prerequisite to its transmissions among humans. Therefore, understanding the receptor binding specificity of influenza viruses may lead to the development of sensitive and fast diagnostic tools for use to detect and differentiate different subtypes of influenza viruses, and provide an alternative approach to the current methods based on RT-PCR (which is highly accurate but time consuming)[75] and ELISA based on antibody-nucleoprotein interaction (which is quick but less accurate).[76]

In contrast to the binding preferences of various HA subtypes, the effect of HA glycosylation on the sialoside binding activities of HA functions has yet been elucidated. The addition and processing of oligosaccharides to N-glycosylation sites has been implicated to play critical roles in proper folding and translocation of membrane and secretory proteins. N-glycosylation is also important in maintenance of protein conformation and stability and in modulation of biological activities.[77] In addition, glycans can protect proteins from clearance and proteolysis. For virus glycoproteins, they can act as a glycan shield to protect virus from immune attacks, yet it may negatively impact the survival of viruses by impeding recognition and interaction of virus surface proteins with cell receptors during infection. In the case of influenza viruses, numerous reports have demonstrated that loss of carbohydrates on HA can modulate its biological functions. For example, Deom et al.[78] reported that loss of a complex oligosaccharide from the tip of the HA would increase virus-cell interaction and make the mutant viruses easier to survive in the infected cells. The increased interaction of less-glycosylated HA to sialosides was also demonstrated by our recent studies where the inventors compared the sialoside binding affinities of soluble HA bearing various glycan lengths using sugar microarray.[79] The results showed that HA digested with endoglycosidase H to remove most of the glycans except the very first GlcNAc showed the highest binding affinities to sialosides.[16] In addition to global changes on the glycosylation patterns of HA as what the inventors did previously, the contribution of individual glycans of full-length HA on sialoside binding activities was investigated. To further dissect the oligosaccharide contribution in HA sialoside binding, this report focused on delineations of the contribution of single glycosylation sites of HA.

Preparation of Sialosides Array for HA Sugar Binding Evaluation.

The inventors have demonstrated a new sialyl phosphate donor to create some of natural occurring sialosides. In order to increase the synthetic efficiency for the creation of a sialoside array, our strategy was to use "sialylated disaccharide" as building blocks.[80] By using the disaccharide A[81-83] as a building block, seventeen α(2→3)-linked sialosides (1-17) of disaccharides to hexasaccharide were synthesized. Using the disaccharide B as a basic building block, the same strategy can be used to effectively build up ten α(2→6)-linked sialosides (21-30). To probe HA binding specificities and affinities, these sialosides with different sialic acid linkages and glycan lengths, and different sugar types and additional sulfation, but with the same amino group linker (FIG. 1; see Supporting information for the synthesis of the compounds). These glycans were spotted onto the NHS-activated glass slide via amide bond formation to create a sialosides array for HA binding evaluation.

Establishment of a Detection Platform for $K_D$ Determination of Sialosides Binding.

The HA binding activities were conventionally monitored using precomplexes of HA- or tag-specific antibodies and fluorophore-conjugated secondary antibodies.[84] The strategy would undoubtedly amplify the signals to facilitate the detection and the profiling, yet may impose complications for quantitative analysis.[85] The inventors therefore devised to incorporate a neutral streptavidine(SA)-tag onto the C-terminal of recombinant HA. For array detection, the inventors tested precomplexes strategy (to form HA-SA-Cy3 complexes first followed with sugar binding analysis) as well as sequential binding. The results (data not shown) revealed that incubation of recombinant HA with SA-Cy3 in 1:1 molar ratio prior to sugar binding for detection provided the most reproducible results. In addition, this strategy can provide clear and consistent binding for low concentration HA, which can be used for quantitative biochemical analysis.[85]

Differential Receptor Binding Preferences of HAs from Seasonal and Pandemic Flu.

Figure 2A:
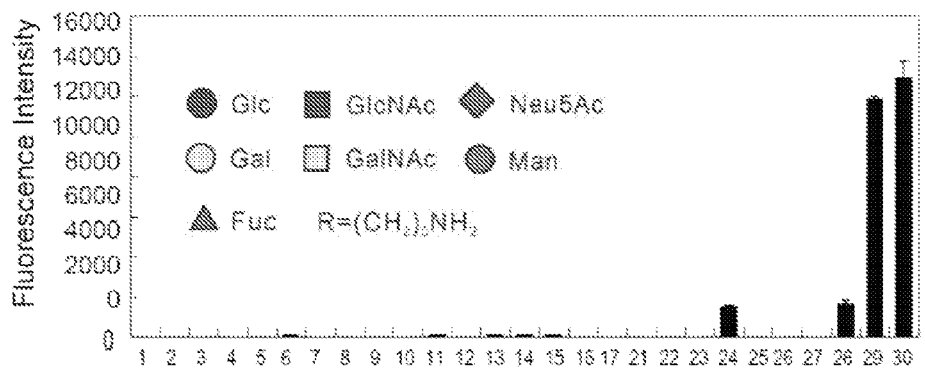
FIGS. 2A-2G show differential binding patterns of sialosides to HA from influenza viruses: (2A) H1N1/California/07/2009 (2009Pandemic), (2B) H1N1/Brisbane/59/2007 (2009 seasonal), (2C) H1N1/New Caledonia/1999(1999-2006 seasonal), (2D) H3N2/Brisbane/10/2007 (2009seasonal), (2E) H5N1/Vietnam/1194/2004 (Avian), (2F) H7N7/A/Netherlands/219/03 (Avian), and (2G) H9N2/A/Hong Kong/1073/99 (Human).
Figure 2B:
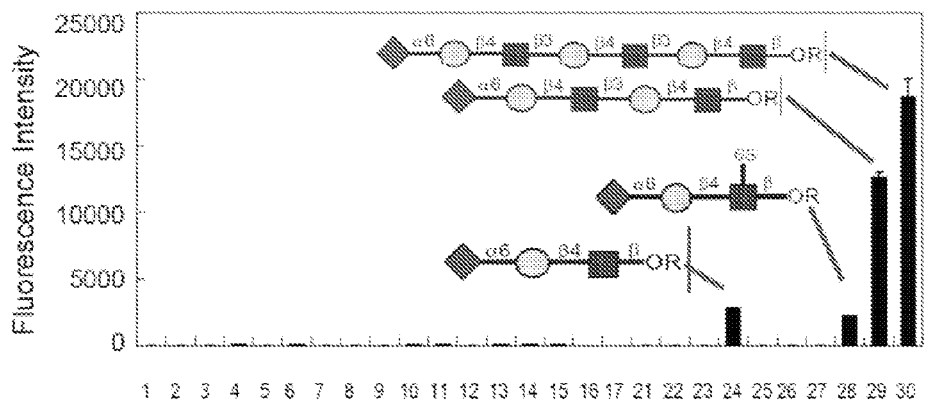
Figure 2C:
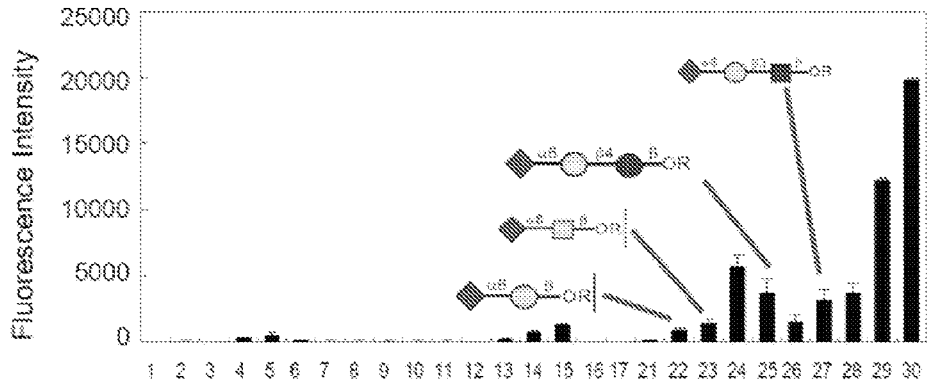
Figure 2D:
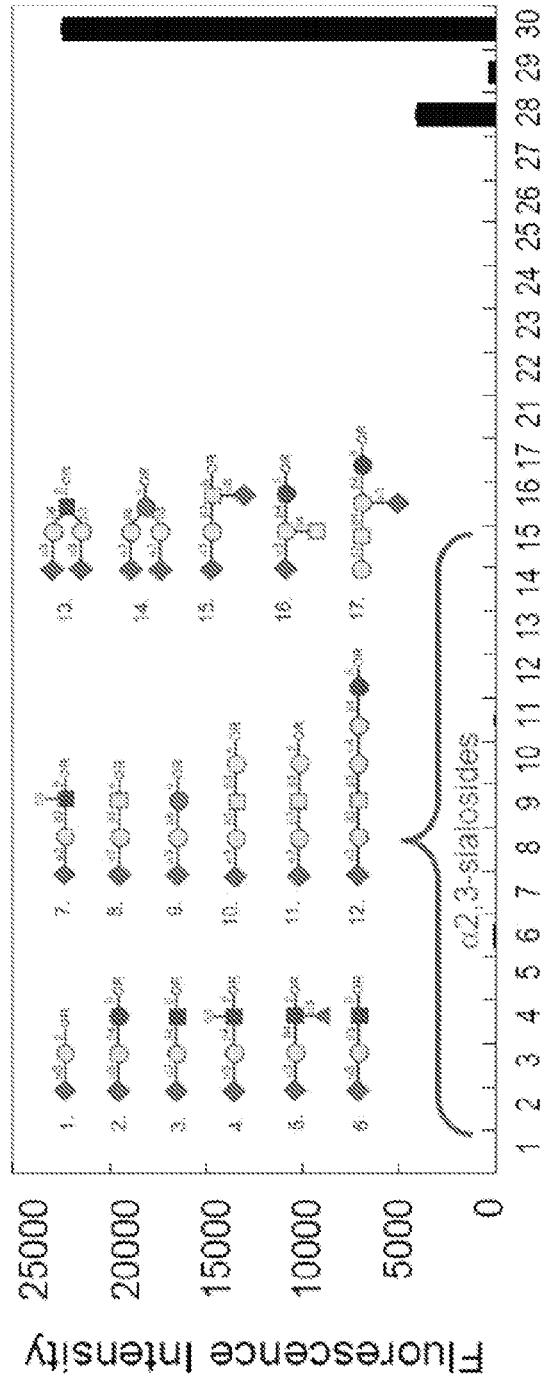

Our goal is to select minimum numbers of glycan to provide a convenient and efficient profiling system to differentiate influenza virus subtypes. The inventors compared the binding preferences of recombinant HA from the viruses that caused seasonal and pandemic flu. The results indicated that HA from both pandemic H1N1 (California/07/2009) (FIG. 2A) and seasonal H1N1 influenza virus Brisbane/59/2007 (Br/59/07) (FIG. 2B) showed similar binding profiles, with higher binding activities toward longer α(2→6) sialosides. However, it was noticed that 2009 pandemic H1 seemed to have reached the maximum binding activities towards α(2→6) sialoside containing 5 sugar units, yet H1 from Brisbane strains showed the highest binding activities towards α(2→6) sialoside containing 7 sugars. Further $K_D$ analysis (FIG. 6) revealed that H1 from Br/59/07 has higher affinities towards sugar 24 and 28 than H1 from 2009 pandemic strain did. For sugar 29 and 30, Br/59/07H1 showed high binding activities even when protein was used at low nM and therefore $K_D$ determination was not successful. Compared to earlier circulating strains H1N1/New Calcdonia/1999 (NC/99) (FIG. 2C), it was clear that recent H1N1 strains only showed binding capacities towards longer α2→6 sialosides, implying that recent strains has not gained strong binding toward human receptors therefore efficient transmissibilities among humans. On the other hand, H3 from Brisbane/10/2007 (Br/10/07) showed narrower binding profiles towards only two α2→6 sialosides, 28 and 30. It was surprised that binding can be only observed towards 30, the α2→6 sialoside containing three repeats of LacNAc, but not 29 with two LacNAc repeats (FIG. 2D).

Figure 2E:
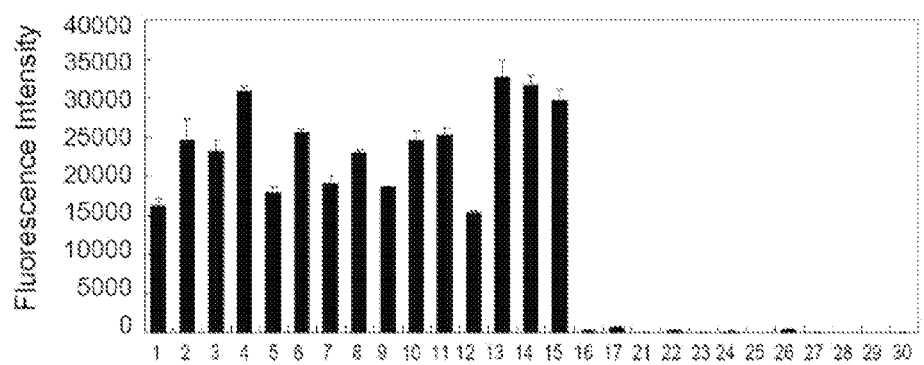
Figure 2F:
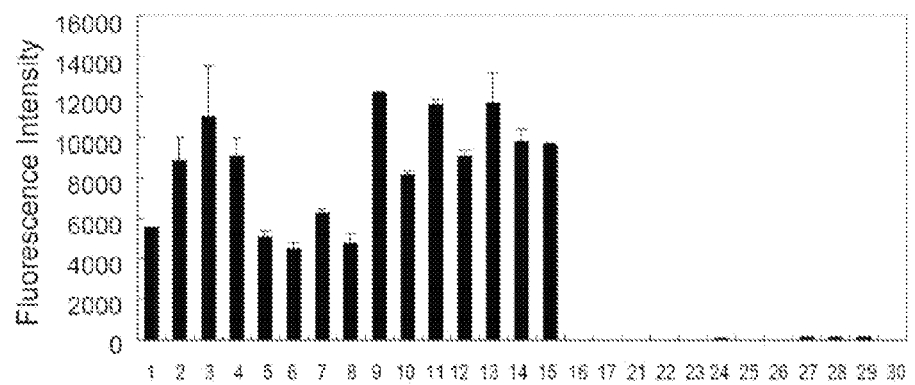
Figure 2G:
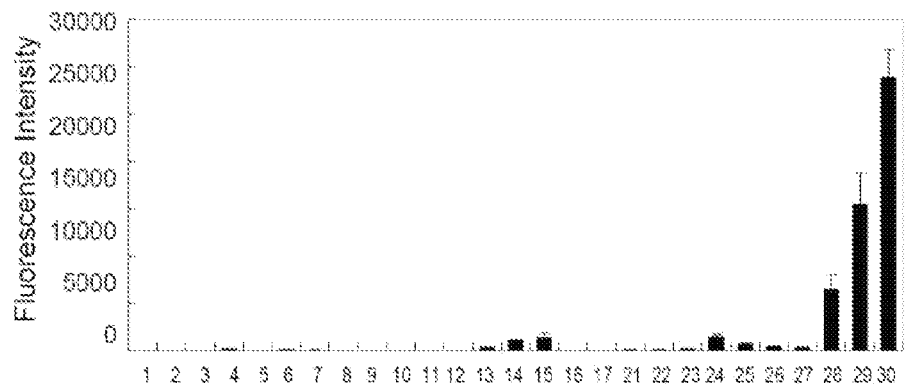

The same array was also used to profile the binding pattern of H5 (FIG. 2E), H7 (FIG. 2F), and H9 (FIG. 2G). As expected, HA from human and avian viruses showed respective binding profiles. The results also suggested that binding to 28 and 30 is unique to human viruses, but not avian viruses. Furthermore, the binding to 24 can be used to differentiate H1 which can bind to this specific sugar vs. H3 which cannot. In addition, binding to disaccharide (22 or 23) may imply strong foothold among human populations. These sugars, together with α2,3-trisaccharide, can be used to differentiate HA subtypes and may have potential to provide as a quick test upon emergence of an influenza outbreak.

Real Influenza Viruses Binding Profiling.

Figures 3A, 3B, 3C, 3D:
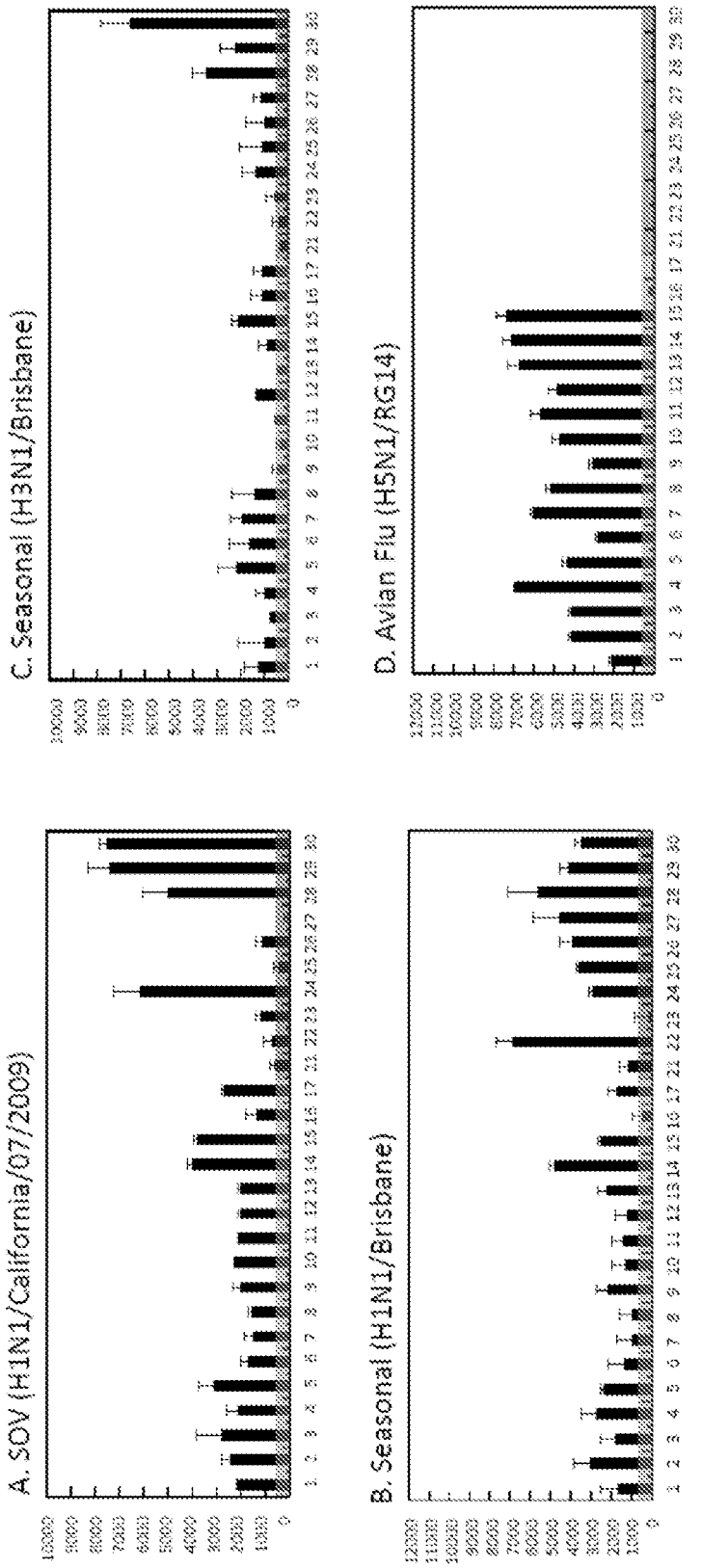
FIGS. 3A-3D shows glycan array analyses of the four viruses investigated—(3A) SOV (HiN1/Claifornia/07/2009), (3B) Seasonal (H1N1/Brisbane), (3C) Seasonal (H3N1/Brisbane), and (3D) Avian Flul (H5N1/RG14). The binding signals are shown as means of duplicate spots at 100μM per spot. Each experiment was repeated twice. Arrays consisted of twenty seven sialylated oligosaccharide probes, printed on NHS-coated glass slides (NHS: N-Hydroxy Succinimide). The various types of terminal sialic acid linkage are indicated by the colored panels as defined at the bottom of the figures.

The relationship of real viruses and HA proteins towards sialosides binding was investigated. The receptor-binding characteristics of four isolates of the influenza virus by glycan array analysis were compared directly by using the same sialosides array. A clear distinction among the receptor-binding repertoire of the Cal/09 H1N1, Brisbane H1N1, Brisbane H3N1, and RG14 H5N1 was observed (FIG. 3). The Cal/09 H1N1 (FIG. 3A) and Brisbane H1N1 viruses (FIG. 3B) bound not only to the majority of α(2→6) linked sialyl sequences, but also to a considerable range of α(2→3) linked sialyl sequences. In contrast, H5N1 (FIG. 3D) bound exclusively to α(2→3) linked sialyl sequences. And, the binding pattern of H3N1 showed preferential binding to α(2→6) linked and α(2→3) linked sialyl sequences (FIG. 3C). The broader specificity, namely, the ability to bind to α(2→3) in addition to α(2→6) linked receptors is also pertinent to the greater virulence of the pandemic virus, and its capacity to cause severe and fatal disease in humans. Binding to α(2→3) linked receptors is thought to be associated with the ability of influenza viruses to infect the lower respiratory tract where there is a greater proportion of α(2→3) relative to α(2→6) linked sialyl glycans. The differences in receptor binding among the viruses may therefore become a good candidate for classifying the serotype of influenza viruses.

The binding preference of RG14 is the same with the preferences of recombinant H5. In the case of H1N1 virus, the binding profiles using the whole virus is slightly different with the profile obtained with recombinant proteins. As recombinant HAs, the viruses showed the strongest binding toward long α(2→6) sialosides. However, the viruses also showed significant binding to α(2→3) sialosides, which the inventors don't usually see with recombinant HAs. The intrinsic binding affinity of sialosides for the hemagglutinin is dominated through polyvalent interactions at the cell surface. Therefore, protein features of presentation on cell surface can have a major impact in receptor recognition; these include the orientation and density of the HA. Furthermore, the tip of the globular region harbors the receptor-binding pocket, which is known to be of crucial importance for the process of virus binding to its receptor. The orientation, number, and structure of N-glycans neighboring the receptor-binding pocket appear to be potent regulators of receptor specificity, which may cause the difference of binding preferences between recombinant HA and whole virus as well.

Effects of Site-Specific Glycosylation on Sialoside Binding Activities of Influenza Hemagglutinin.

Figures 4A, 4B:
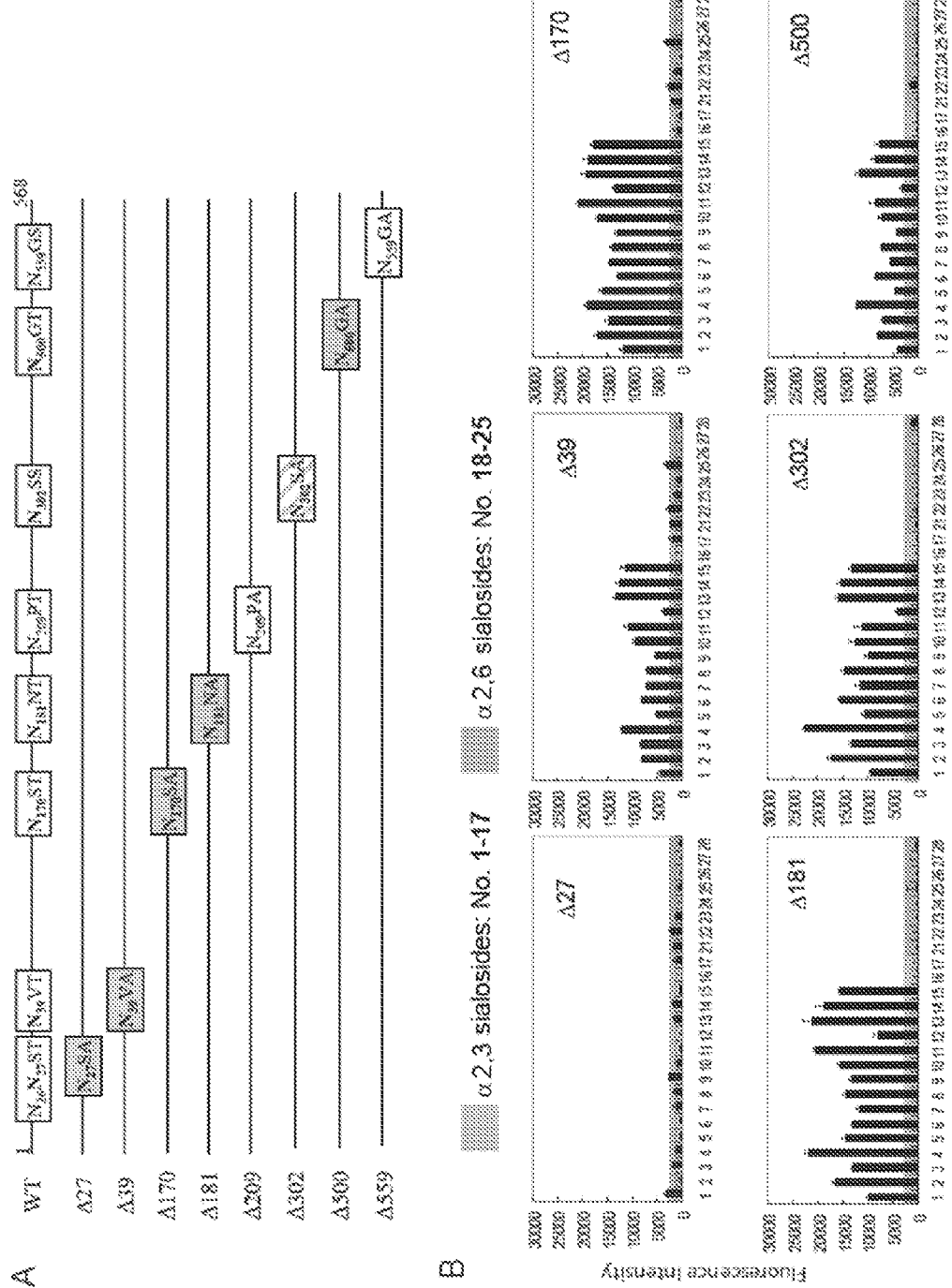
FIGS. 4A-4B show binding profiles of HA glycosylation mutant. (4A) Nine glycosylation sites were predicted using H5 as an example. The predicted glycosylation sites in grey boxes were confirmed to be glycosylated using LCMS. The sites in empty box were confirmed to be un-glycosylated and the one in hatched box may be partially glycosylated. The glycosylation mutant were created by changing Nx(T/S) to NxA. (4B) Sugar binding patterns of individual glycosylation mutants.

It is believed that influenza HA needs to be glycosylated to have proper function, i.e. to bind sialylated host receptors to mediate virus entry. Glycosylation sites on certain regions of HA are highly conserved.[86] It has also been reported that changes in glycosylation pattern of HA may be advantageous or detrimental to HA binding activities and eventually to the survival of the virus.[87] To elucidate the effects of site-specific glycosylation on the sialosides binding activities, the inventors produced HA mutants in which the individual predicted glycosylation sequon Nx(S/T) was changed to NxA to block N-glycosylation at the specific sites (FIG. 4A). Except for Δ26, Δ170, Δ209, and Δ559, the HA mutants showed an increased rate of mobility compared with WT, corresponding to the loss of one carbohydrate chain on the designated sites (data not shown). The result is consistent with the mass sequencing analysis, where carbohydrates were identified to attach to site N26/27, N39, N170, N181, N302, N500, and N559 (Data not shown). The subsequent sugar binding analysis suggested that that the mutations Δ39, Δ302, Δ500 as well as Δ209 did not significantly change sialoside binding profile of WT HA (FIG. 4B). In contrast, the mutation Δ27 to block the glycosylation on N27 appears to be detrimental for sugar binding activities.

Figure 5:
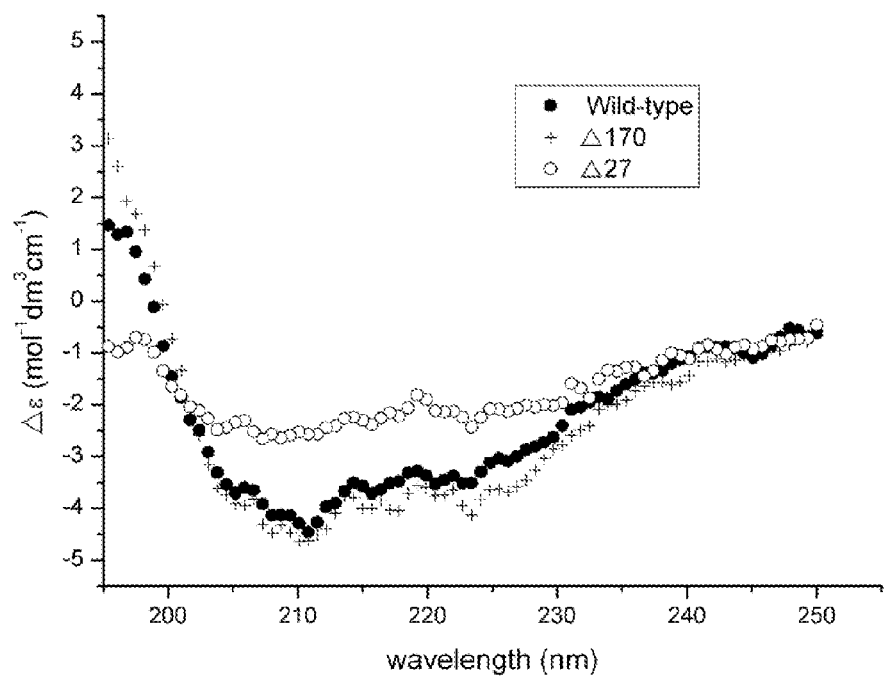
FIG. 5 shows CD spectra showed that Δ170 exhibits similar secondary structure with the wild-type HA while the secondary structure of Δ27 is changed.
Figure 8:
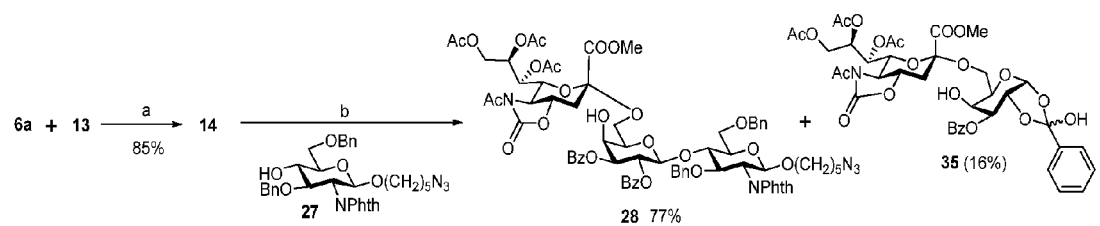
FIG. 8 shows Scheme 1 showing stepwise Synthesis of Influenza HA Receptor α(2→6)-Linked Trisaccharide 28. "Reagents and Conditions: (a) 6a (1.5 equiv), 13 (1.0 equiv), TMSOTf (1.5 equiv), 4Å MS, CH$_2$Cl$_2$,−78° C.; (b) 14 (1.2 equiv), NIS (2.0 equiv), TMSOTf (0.5 equiv), 4Å MS, CH$_2$Cl$_2$, −40° C.
Figure 10:
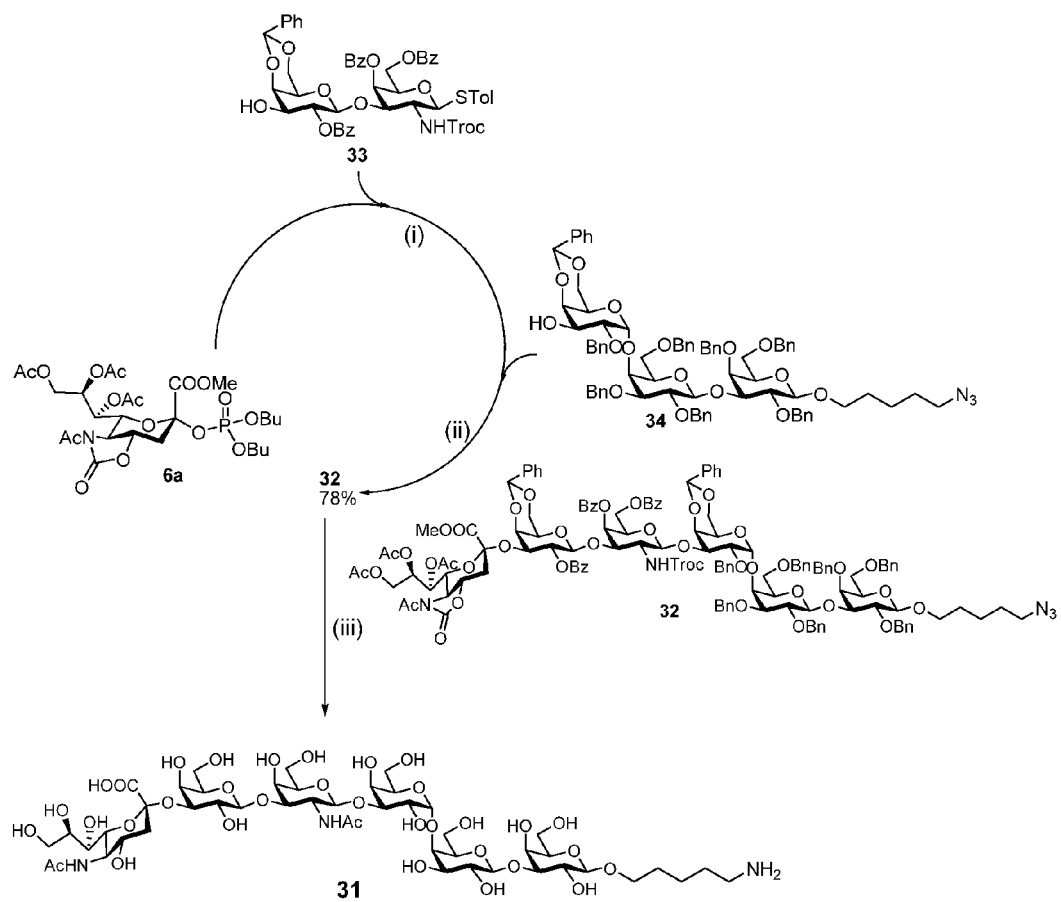
FIG. 10 shows Scheme 3 showing One-Pot Synthesis of SSEA-4 Hexasaccharide. Reagents and Conditions: TMSOTf, MS 4Å, CH$_2$Cl$_2$, −78° C. (ii) NIS, overall 78%; (iii) (a) NaOMe, MeOH (b) Zn, AcOH, THF; (c) Ac$_2$O, pyridine, DMAP (d) 0.1 N NaOH Pd(OH)$_2$, H$_2$, THF:MeOH: AcOH:H$_2$O = 10 : 8 : 1 : 0.7 (v/v).
Figure 11:
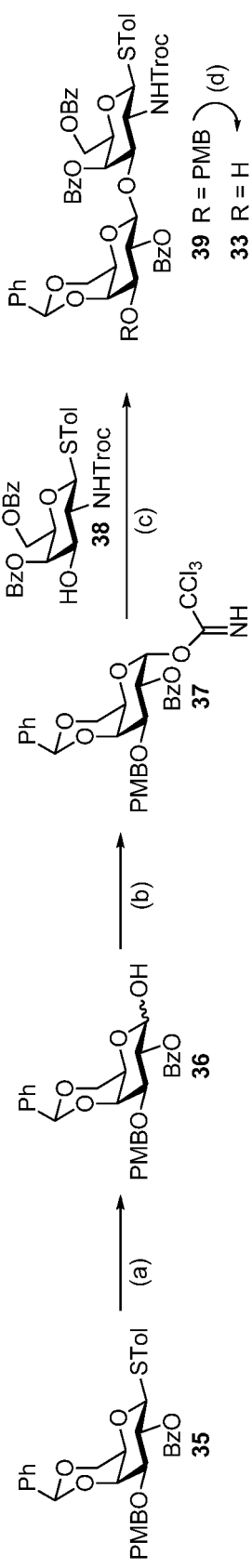
FIG. 11 shows Scheme 4 showing synthesis of Disaccharide 33. Reagents and Conditions: (a) TMSOTf, NIS, CH$_2$Cl$_2$/H$_2$O (9:1), 0° C., 75%; (b) K$_2$CO$_3$, CCl$_3$CN, 65%; (c) TMSOTf, MS 4Å, −40° C., 60%; (d) DDQ, CH$_2$Cl$_2$/H$_2$O (9:1), 96%.
Figure 12:
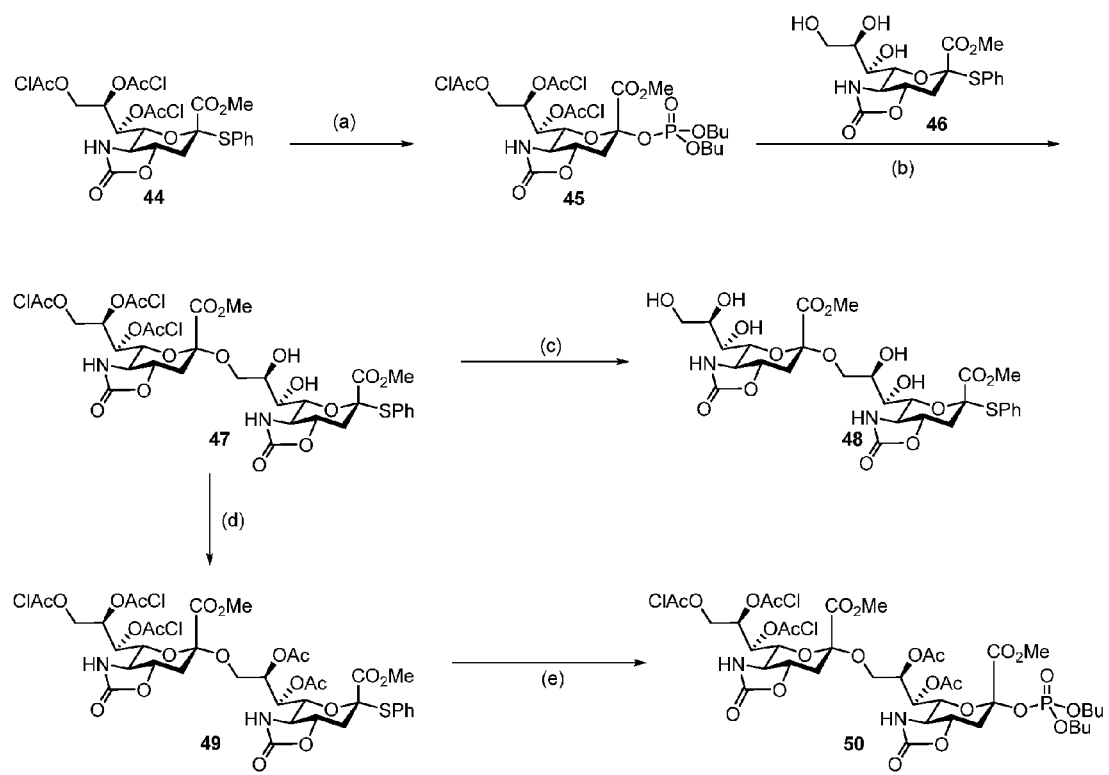
FIG. 12 shows Scheme 5 showing synthesis of α(2→9)-Linked Disaccharide Building Blocks. Reagents and Conditions: (a) dibutyl phosphate, NIS, TfOH, CH$_2$Cl$_2$, 0° C., 96%; (b) TMSOTf, CH$_2$Cl$_2$/MeCN, −78° C., 1 h, 80%; (c) thiourea, 2,6-lutidine, DMF, 60° C., 12 h, 82%; (d) Ac$_2$O, Pyridine, DMAP, CH$_2$Cl$_2$, −50° C., 5 h 80%; (e) dibutyl phosphate, NIS TfOH, CH$_2$Cl$_2$, 0° C., 3 d 73%.
Figure 13:
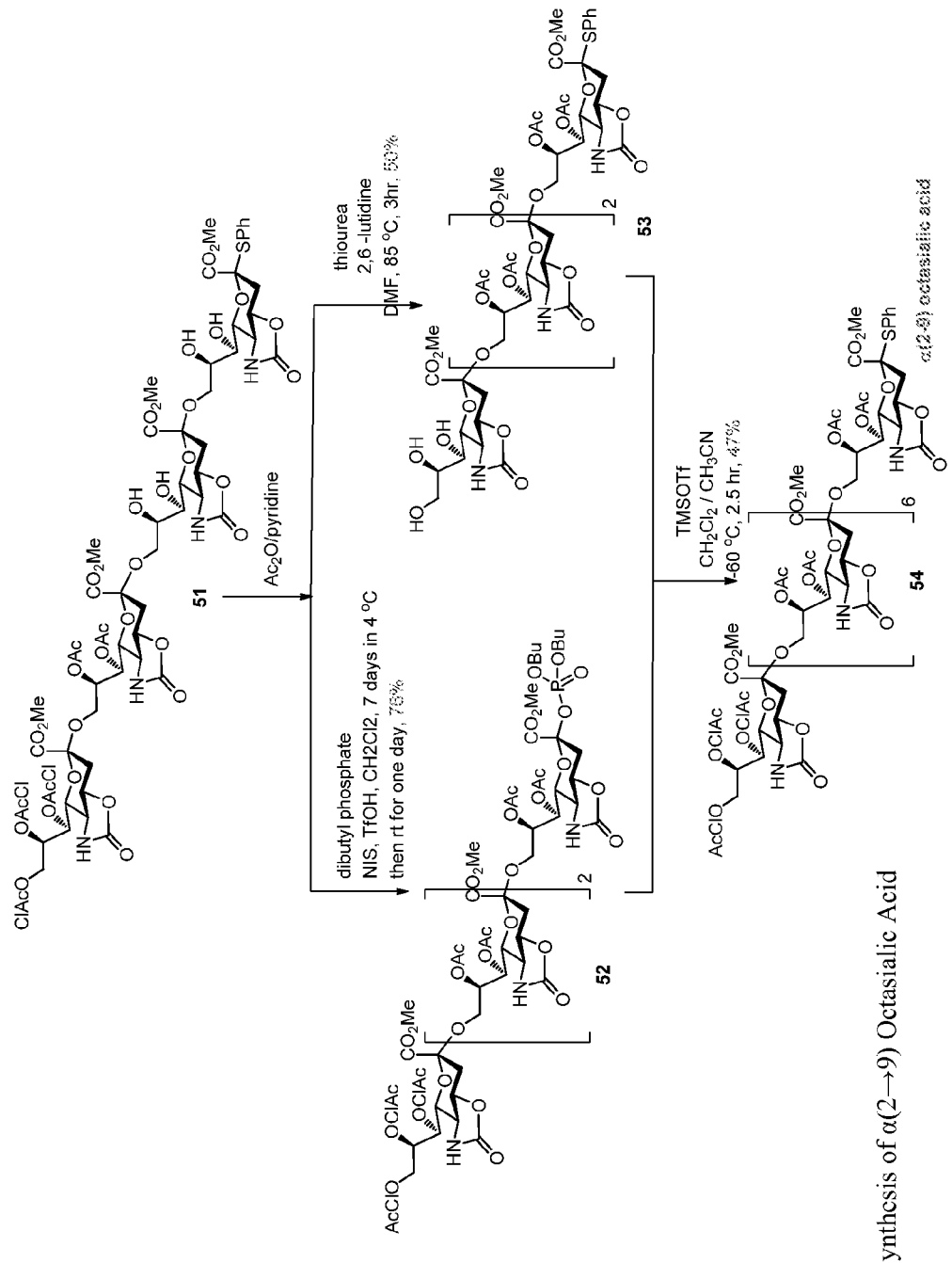
FIGS. 13 shows Scheme 6 showing synthesis of α(2→9) Octasialic Acid.
Figure 14:
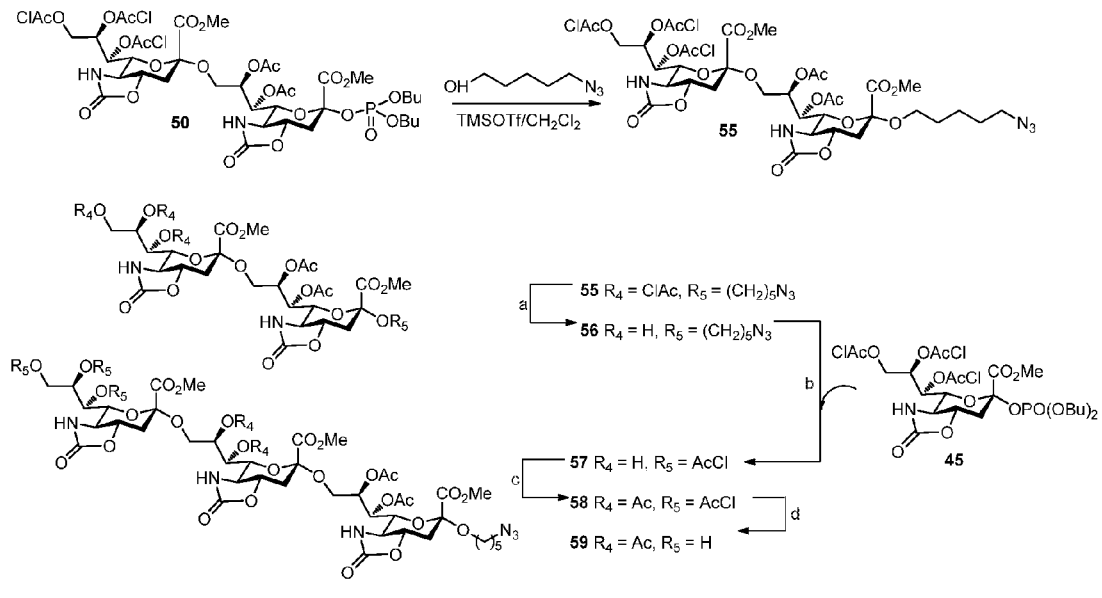
FIG. 14 shows Scheme 7 showing synthesis of di-, tri-, tetra-, hexa-, octa-sialic acid derivatives.
Figure 14:
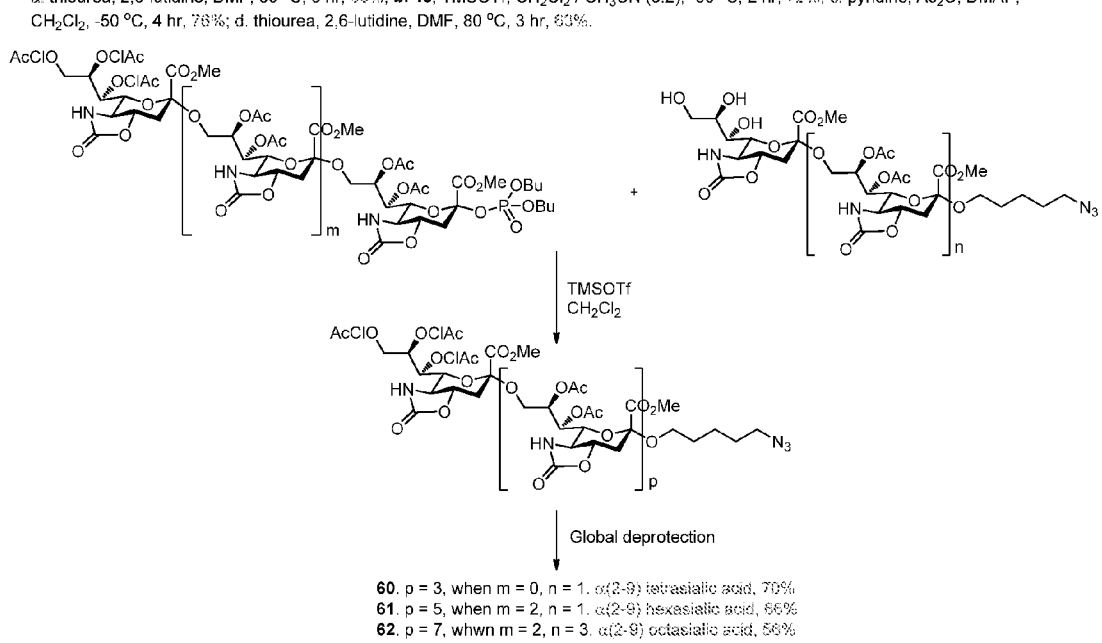
Figure 15:
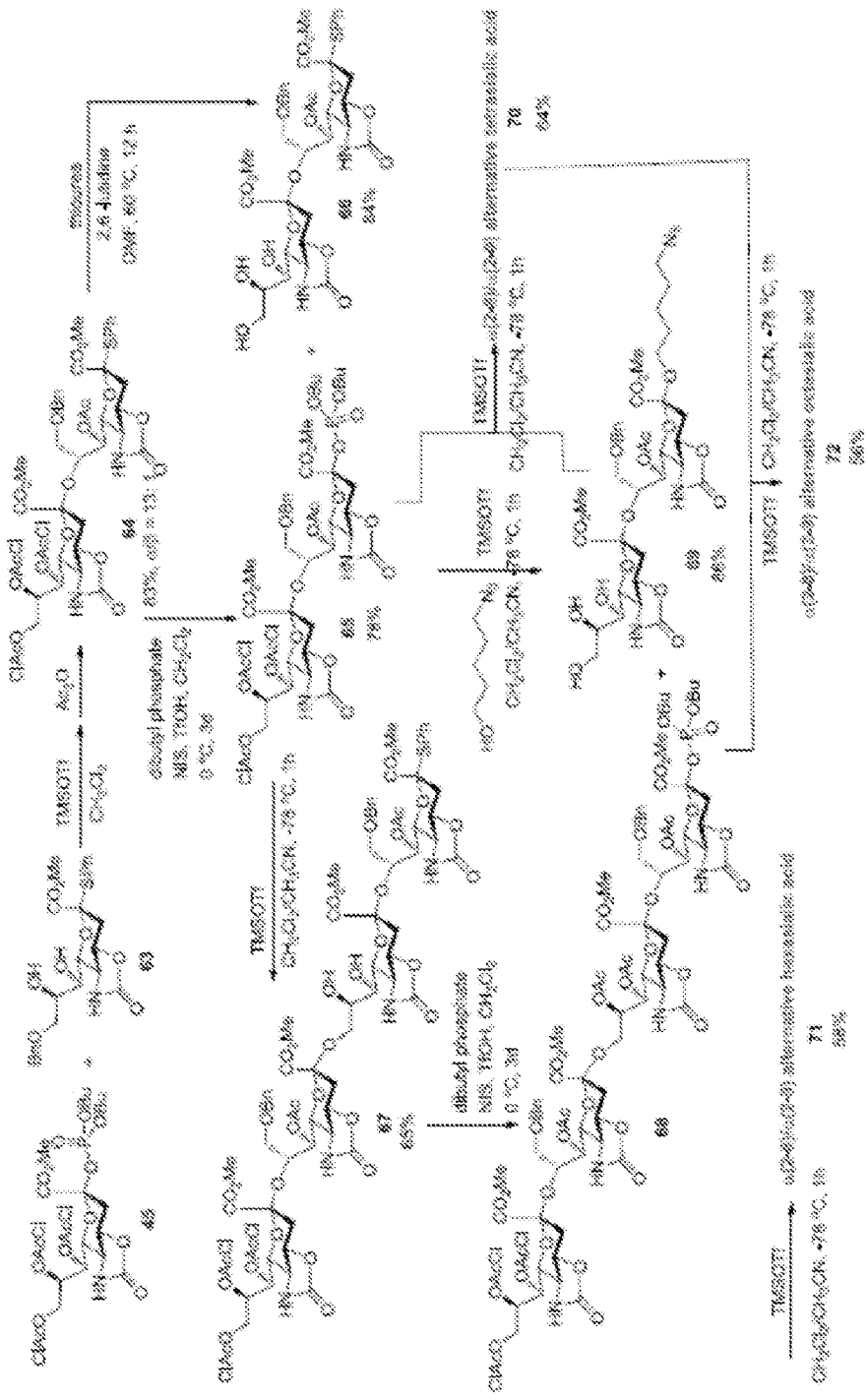
FIG. 15 shows Scheme 8 showing synthesis of α(2→8)/α(2→9) alternative polysialic acids.
Figure 16:
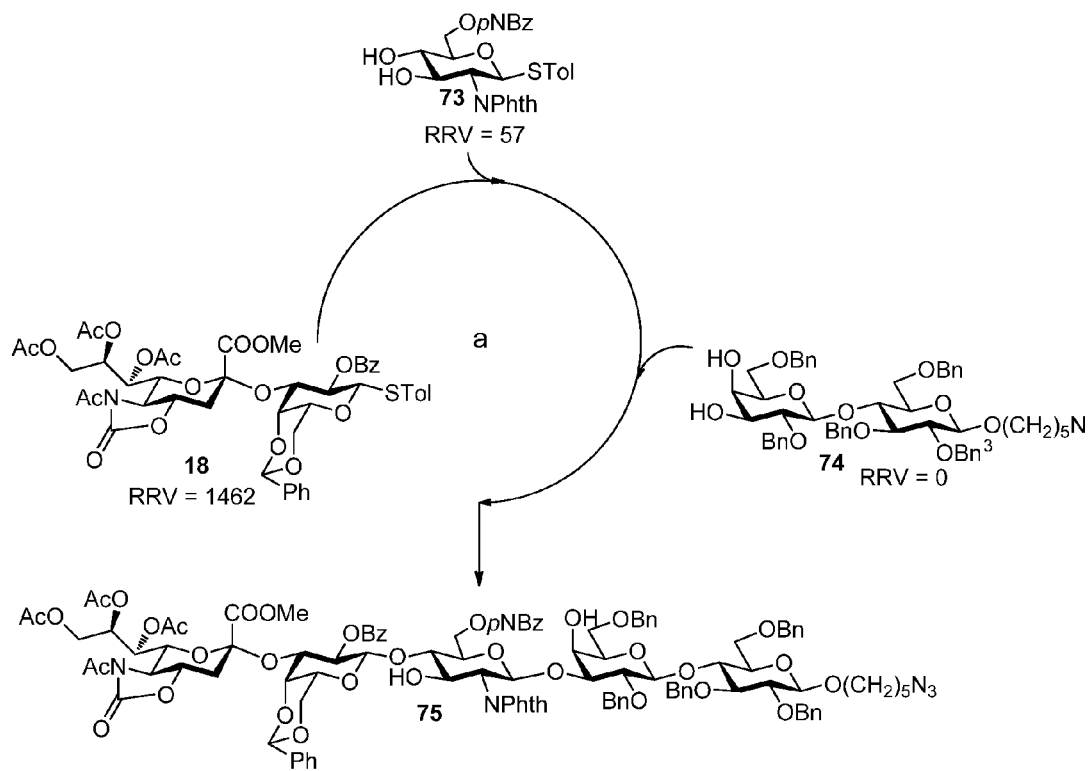
FIG. 16 shows Scheme 9 showing reactivity-based One-Pot Glycosylation of Pentasaccharide 75. Reagents and Conditions: (1). NIS, TfOH, 4A molecular sieves CH$_2$Cl$_2$, −78° C.; (2). NIS, TfOH, −20° C. to RT.

The glycosylation on amino-terminal N-glycosylation sites, i.e. N27, has been implicated in protein transport and folding steps. The loss of N20/21 of H2 was demonstrated to decrease hemadsorption and cell fusion activities.[88] It was also reported that HA without glycosylation on N-terminal would be trapped in endoplasmic reticulum and cannot be transported to cell membrane.[89] Our results showed that removal of N27 glycosylation sites almost demolished the sugar activities of WT HA. To further dissect if the loss of binding activities is due to improper folding as other reports suggested, circular dichroism (CD) spectroscopy analysis was conducted. The results showed that the secondary structure of Δ27 changed while another glycosylation mutant with similar binding (Δ170) showed the same spectrum as the wild-type HA does (FIG. 5). The results confirmed that Δ27 may not maintain proper structures, implying N-glycosylation on N27 occurs co-translationally and is important for proper folding. Glycosylation on N27 indeed is critical for HA structure and thus for sugar binding activities. On the other hand, although the carbohydrates found on the receptor binding domain were shown to modulate the antigenic properties, hemadsorption activities and cell fusion activities,[90] our array studies revealed that the binding patterns did not change much for glycosylation mutants yet the binding affinities of glycosylation mutant slightly decreased (FIG. 7).

The inventors have developed an efficient approach for the preparation of dibutyl sialyl phosphate donors with N-TFA and N-acetyl-5-N,4-O-carbonyl or 5-N,4-O-carbonyl protection. The glycosyl donor properties of N-acetyl-5-N,4-O-carbonyl protected sialyl phosphate have been used to prepare the essential α(2→6)-, α(2→3)-, α(2→8)- and α(2→9)-linked disaccharide building blocks, which can serve as the starting materials for the preparation of more complex sialosides. Also, the one-pot protocol described herein offers a versatile approach for the α-selective synthesis of α(2→6)- and α(2→3)-linked sialosides. Using these strategies, several biologically significant sialyl glycans have been synthesized.

Sialoside binding activities of recombinant HAs and real virus were screened with 27 sialosides. The binding preference is identical between H5N1 virus and recombinant H5. A slight difference in α(2→3) sialosides binding activities was observed in between Cal/09 H1N1 virus and Cal/09 recombinant HA. The difference of binding preferences between recombinant HA and real virus may result from the various orientation and density of HA presenting on virus cell surface.

In study of the role of N-glycosylation sites for sugar binding, N27 glycosylation site was mutated. Circular dichroism (CD) spectroscopy analysis confirmed that N-glycosylation on N27 occurs co-translationally with protein folding and cannot maintain the structure of proteins. Mutations of certain N-glycosylation sequons on HA suggested that certain glycosylation sequons such as $N_{27}ST$ have determined effect on HA function. The studies that use site-specific glycosylation mutants to elucidate the relationship between HA glycosylation and its sugar binding activities also shed light on the importance of HA glycosylation. Furthermore, number 24, 28, and 30 glycan, together with α2,3-trisaccharide, can be used to differentiate HA subtypes and have great potential to provide as a quick test upon emergence of an influenza outbreak.

Using the sialylated disaccharide strategy, 27 sialosides have been synthesized to prepare a sialosides microarray on glass slides which can be used to profile not only the receptor binding specificity of various HA subtypes but also HAs with different glycosylation patterns and real influenza viruses.

It has been known that the oligosaccharides of the Influenza hemagglutinin have some important biological functions.[91] For example, the oligosaccharides in the head region of hemagglutinin block the antigenic site. Also, HA receptor binding specificity was affected by the absence of a complex glycan chain near the receptor binding site.[87] In order to address how glycosylation affects the specificity of HA, the inventors adopted the powerful glycan microarray technology in combination with HAs produced from different expression systems which generate different N-glycosylation patterns on the protein surface. In our results, HAs with complex-type or high-mannose type glycosylation showed subtle differences in specificity (profiling results).

The sialosides of the invention comprise those found on the surface of various viral, bacterial, fungal or other pathogens. The sialosides according to the invention also comprise those found on cell surface receptors that bind the pathogens. Sialosides that participate in such interactions are found on surface glycoproteins from influenza virus neuraminidase, influenza virus hemagglutinin, influenza virus M2 protein, human respiratory syncytial virus (RSV)-viral proteins, RSV F glycoprotein, RSV G glycoprotein, herpes simplex virus (HSV) viral proteins, herpes simplex virus glycoproteins gB, gC, gD, and gE, *Chlamydia* MOMP and PorB antigens, core protein, matrix protein or other protein of Dengue virus, measles virus hemagglutinin, herpes simplex virus type 2 glycoprotein gB, poliovirus I VP1, envelope glycoproteins of HIV 1, hepatitis B surface antigen, diptheria toxin, *Streptococcus* 24M epitope, Gonococcal pilin, pseudorabies virus g50 (gpD), pseudorabies virus II (gpB), pseudorabies virus III (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, Serpulinahydodysenteriae protective antigen, bovine viral diarrhea glycoprotein 55, Newcastle disease virus hemagglutinin-neuraminidase, swine flu hemagglutinin, swine flu neuraminidase, foot and mouth disease virus, hog cholera virus, swine influenza virus, African swine fever virus, *Mycoplasma* liyopneutiioniae, infectious bovine rhinotracheitis virus, infectious bovine rhinotracheitis virus glycoprotein E, glycoprotein G, infectious laryngotracheitis virus, infectious laryngotracheitis virus glycoprotein G or glycoprotein I, a glycoprotein of La Crosse virus, neonatal calf diarrhea virus, Venezuelan equine encephalomyelitis virus, punta toro virus, murine leukemia virus, mouse mammary tumor virus, hepatitis B virus core protein and hepatitis B virus surface antigen or a fragment or derivative thereof, antigen of equine influenza virus or equine herpes virus, including equine influenza virus type A/Alaska 91 neuraminidase, equine influenza virus typeA/Miami 63 neuraminidase, equine influenza virus type A/Kentucky 81 neuraminidase equine herpes virus type 1 glycoprotein B, and equine herpes virus type 1 glycoprotein D, antigen of bovine respiratory syncytial virus or bovine parainfluenza virus, bovine respiratory syncytial virus attachment protein (BRSV G), bovine respiratory syncytial virus fusion protein (BRSV F), bovine respiratory syncytial virus nucleocapsid protein (BRSVN), bovine parainfluenza virus type 3 fusion protein, bovine parainfluenza virus type 3 hemagglutinin neuraminidase, bovine viral diarrhea virus glycoprotein 48 and glycoprotein 53, glycoprotein E of Dengue virus and glycoprotein E1 or E2 of human hepatitis C virus.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials. NHS-coated glass slides were obtained from SCHOTT (Nexterion H), Monoclonal antibodies to influenza hemagglutinin were kindly provided by the NIH Biodefense and Emerging Infections Research Resources Repository, NIAID, NIH, and the Cy3-labeled anti-mouse secondary antibodies as well as Cy3-labeled streptavidin were purchased from Jackson ImmunoResearch. Standard chemicals and reagents were purchased from commercial suppliers and used as received.

Construction of Hemagglutinin Expression Plasmids. The full-length genes encoding HA from H1N1 Influenza A Virus including SOV California/07/2009, Brisbane/59/2007, New Calcdonia/20/1999 (ABF21272.1), H3N2 Brisbane/10/2007 (ABW23422.1), H5N1 Vietnam/1194/2004 (ABP51976.1), H7N7 Netherlands/219/03 (AAR02640.1), or H9N2 HongKong/1073/99 (CAB95856.1) fused with a C-terminal Strep (Trp-Ser-His-Pro-Gln-Phe-Glu-Lys) and $(His)_6$ tag were cloned into pcDNA (Invitrogen) for expression in human 293T cells. The sequences were confirmed by DNA sequencing and prepared in high quality for expression. The genes were cloned into pcDNA for expression in human 293T cells.

Construction of Hemagglutinin Glycosylation Mutants. The nucleotide sequence of consensus hemagglutinin H5 ($CHA5^{92}$) was cloned into pcDNA with a C-terminal Strep-Tag and the resulting plasmid was used as the templates for site-directed mutagenesis. The N-glycosylation sites of CHA5 were predicted with The NetNGly server provided by Expasy (www.expasy.org). The putative N-X-S/T sequons were then mutated to N-X-A using site-directed mutagenesis with QuikChange® II Site-Directed Mutagenesis Kit (Stratagene, La Jolla, Calif., USA). The mutagenesis was confirmed by DNA sequencing and the glycosylation knockouts were confirmed by SDS-PAGE analysis.

Expression of Recombinant Full-Length Hemagglutinin from Expressed Cells. For expression in human 293T cells, pcDNA carrying the gene of interest were prepared in high quality and transfected with cation lipids DOTAP/DOPE (1:1) (Avanti Lipids) for transient expression. The expression of hemagglutinin was confirmed with immunoblots using anti-$(his)_6$ antibodies (Qiagen) or specific anti-hemagglutinin antibodies, and the horseradish peroxidase-conjugated secondary antibodies (PerkinElmer).

Purification of Recombinant Hemagglutinins. The cells containing recombinant full-length HA were lysed in 20 mM Hepes buffer (pH 7.4) using a microfluidizer. The lysates were centrifuged at 12,000 rpm for 10 minutes and the supernatant were collected for a second centrifugation at 40,000 rpm for 1 hour. Next, the pellets were extracted with 20 mM Hepes buffer containing 1% dodecyl maltoside for 2 hours followed with a brief centrifugation at 12,000 rpm. The supernatant were then passed through an affinity column packed with Nickel Sepharose Hi Performance (GE Healthcare). After washes with 20 mM Hepes buffer containing 0.5% dodecyl maltoside, the recombinant HA was eluted with 500 mM imidazole in 20 mM Hepes buffer. For the purification of HA ectodomain, the cell medium were collected and passed through a $Ni^{2+}$-affinity column as described. The recombinant HA ectodomain were eluted with 500 mM imidazole in 20 mM Hepes buffer. The purified proteins were concentrated using Amicon (Millipore) and stored at 4° C. The concentrations were determined using immunoblots with anti-hemagglutinin and horseradish peroxidase (HRP)-conjugated secondary antibodies.

Microarray Analysis of Sugar Binding Activities of Hemagglutinin. Microarray were printed (AD3200, BioDot) by robotic pin (SMP2B, TeleChem International Inc.). Nexterion H slides were spotted with solutions of sugar 1-17 and 21-30 at 100 μM from bottom to top with 12 replicates horizontally in each grid and dried under vacuum. The spotted slides were blocked with ethanolamine in sodium borate for 1 hour just before use followed with three washes of 0.05% Tween 20 in PBS buffer (pH 7.4) (PBST). A solution of hemagglutinin at 50 μg/ml in PBST were pre-mixed with Cy3-labeled streptavidin in 1:1 molar ratio for 1 hour prior to incubation of the preformed complexes with the slides for another hours. After six washes with PBST, one wash with PBS, and three washes with distilled water, the slides were air-dried and scanned with a 532 laser using a microarray fluorescence scanner (GenePix 4000B, Molecular Devices). The PMT gain was set to 600. The resulting images were analyzed with GenePix Pro 6.0 (Molecular Devices) to locate and to quantify the fluorescence intensity of all of the spots within the grid. The median of fluorescence intensity of each spot were taken to calculate the median value of binding activities towards each sugar (12 replicates for each sugar). The medians from at least three independent experiments were averaged for the figures. For $K_D$ determination, the preformed complexes were serially diluted for binding reaction[85] and the binding intensities were quantified as described above. The binding intensities at various concentrations of complexes were then fitted to the Langumir isotherms using the Prism (GraphPad, San Diego, Calif.).[93]

Determination of Glycosylation Sites and Deglycosylation of Glycosylation Mutants. Purified HA proteins dissolved in trifluoroethanol/100 mM ammonia bicarbonate (pH 8.5) (1:1 (v:v)) were reduced with 10 mM dithiothreitol for 1 h at 37° C., alkylated with 20 mM iodoacetamide for another 1 h in the dark at 37° C., and subsequently digested with modified trypsin (sequencing grade, Promega) for overnight at 37° C. All of the reagents were prepared in 50 mM ammonium bicarbonate buffer, pH 8.5. After stopping the trypsin digestion by heating at 95° C. for 10 min, the glycans were removed by incubating with 500U PNGase F (glycerol free, New England Biolabs) overnight at 37° C. All samples were dried in vacuo, redissolved in 0.1% formic acid and injected into nano-LC/ESI LTQ FT linear ion trap mass spectrometer (Bruker Daltonics). MS/MS spectra were acquired in a data-dependent acquisition mode that automatically selects and fragments the five most intense peaks from each MS spectrum generated. The MS and MS/MS raw data were processed by Raw2 msm software and searched against an in-house generated NCBI database comprising WT HA and various glycosylation mutants, using Mascot Daemon searching engine. Search criteria were trypsin digestion and variable modifications such as carbamidomethyl (C), oxidation (M), deamidation (D) and N-glycosylation (Gly-Asn). Up to 1 missed cleavage, mass accuracy of 3 ppm on the parent ion and 0.60 Da on the fragment ions were allowed to be included for data analysis. All significant protein hits from Mascot (p<0.05) thus obtained contained no false positive hits from the reverse database.

Virus preparation. Samples of various viruses are collected from the Center for Disease Control and Prevention in TAIWAN. Virus were inactivated by treatment with β-propiolactone (BPL; 0.05% v/v) for 60 minutes at 33° C., and resuspended in 0.01 M phosphate buffered saline pH 7.4 (PBS) and stored at −80° C. Comparison of samples of live and inactivated virus showed that BPL inactivation did not alter receptor binding specificity.[94]

Virus Binding Assay Procedure. Printed slides were analyzed without any further modification. Inactivated whole virus was applied at a concentration around 50 μg/ml viruses (weight of inactivated virus) in PBS buffer containing the neuraminidase inhibitor 10 μM oseltamivir carboxylate. Suspensions of the inactivated viruses with oseltamivir carboxylate were overlaid onto the arrays and incubated at room temperature for 1 h. Slides were subsequently washed by successive rinses in PBS-0.05% Tween, PBS, and deionized water three times. Bound viruses were detected using the following antibodies: homemade rabbit anti-H1 antibody both for SOV California/07/2009 and H1N1 Brisbane; homemade anti-H3 (TC16) antibody for H3N1 Brisbane; and homemade Anti-H5 avian influenza antibody (α-293s) antibody for H5N1 (RG14). The slides were gently rocked at room temperature for 60 min After repeating washing step, binding was detected by overlay with labeled secondary antibodies.

TABLE 10

| References |
|---|
| 1. (a) Schauer, R., Ed. *Sialic Acids: Chemistry, Metabolism and Function*; Springer-Verlag: New York, 1982; Vol. 10. (b) Rosenberg, A., Ed. *Biology of the Sialic Acids*; Plenum: New York, London, 1995. (c) Simanek, E. E.; McGarvey, G. J.; Jablonowski, J. A.; Wong, C.-H. *Chem. Rev.* 1998, 98, 833-862. (d) Varki, A. *Nature* 2007, 446, 1023-1029. |
| 2. Subbarao, K.; Katz, *J. Cell. Mol. Life Sci.* 2000, 57, 1770-1784. |
| 3. (a) Reglero, A.; Rodriguez-Aparicio, L. B.; Luengo, J. M. *Int. J. Biochem.* 1993, 25, 1517-1527. (b) Varki, A. *Glycobiology* 1993, 3, 97-130. (c) Inoue, Y.; Inoue, S. *Pure Appl. Chem.* 1999, 71, 789-800. |
| 4. (a) Muthana, S.; Yu, H.; Cao, H.-Z.; Cheng, J.-S.; Chen, X. *J. Org. Chem.* 2009, 74, 2928-2936 and citations there in. (b) Koeller, K. M.; Wong, C.-H. *Nature* 2001, 409, 232-240 and citations therein. |
| 5. For reviews on chemical sialylations, see: (a) Boons, G. J.; Demchenko, K. V. *Chem. Rev.* 2000, 100, 4539-4565. (b) Ando, H.; Imanura, A. *Trends Glycosci. Glycotechnol.* 2004, 16, 293-303. (c) Boons, G. J.; Demchenko, A. V. In *Carbohydrate-based Drug Discovery*; Wong, C.-H., Ed.; Wiley-VCH: Weinheim, Germany, 2003; Vol. 1, pp 55-102. |
| 6. (a) Okamoto, K.; Goto, T. *Tetrahedron* 1990, 46, 5835-5857. (b) DeNinno, M. P. *Synthesis* 1991, 583-593. (c) Ogawa, T.; Sugimoto, M. *Carbohydr. Res.* 1985, 135, C5-C9. |
| 7. (a) Kondo, H.; Ichikawa, Y.; Wong, C.-H. *J. Am. Chem. Soc.* 1992, 114, 8748-8750; (b) Sim, M. M.; Kondo, H.; Wong, C.-H. *J. Am. Chem. Soc.* 1993, 115, 2260-2267. (c) Martin, T. J.; Schmidt, R. R. *Tetrahedron Lett.* 1992, 33, 6123-6126. (d) Martin, T. J.; Brescello, R.; Toepfer, A.; Schmidt, R. R.; *Glycoconjugate J.* 1993, 10, 16-25. |
| 8. (a) Hasegawa, A. In *Modern Methods in Carbohydrate Synthesis*; Khan, S. H.; O'NeIL, R. A., Eds.; Harwood Academic Publishers: New York, 1996; pp. 277-300. (b) Zhang, Z.; Ollmann, I. R.; Ye, X.-S.; Wischant, R.; Baasov, T.; Wong, C.-H. *J. Am. Chem. Soc.* 1999, 121, 734-753. (c) Nicolaou, K. C.; Ueno, H. In *Preparative Carbohydrate Chemistry*, Hanessian, S. Ed.; Marcel Dekker Inc: New York, 1997; pp. 313-338. (d) De Meo, C.; Parker, O. *Tetrahedron Asymmetry.* 2005, 16, 303-307. |
| 9. (a) Marra, A.; Sinay, P. *Carbohydr. Res.* 1990, 195, 303-308. (b) Martichonok, V.; Whitesides, G. M. *J. Org. Chem.* 1996, 61, 1702-1706. (c) Dziadek, S.; Brocke, C.; Kunz, H. *Chem. Eur. J.* 2004, 10, 4150-4162. |
| 10. (a) Cai, S.; Yu, B. *Org. Lett.* 2003, 5, 3827-3830. (b) Tanaka, S.-I.; Goi, T.; Tanaka, K.; Fukase, K. J. *Carbohydr. Chem.* 2007, 26, 369-394. (c) Liu, Y.; Ruan, X.; Li, X.; Li, Y. *J. Org. Chem.* 2008, 73, 4287-4290. |
| 11. (a) Danishefsky, S. J.; DeNinno, M. P.; Chen, S. *J. Am. Chem. Soc.* 1988, 110, 3929-3940. (b) Takahashi, T.; Tsukamoto, H.; Yamada, H. *Tetrahedron Lett.* 1997, 38, 8223-8226. (c) Haberman, J. M.; Gin, D. Y. *Org. Lett.* 2001, 3, 1665-1668. (d) Haberman, J. M.; Gin, D. Y. *Org. Lett.* 2003, 5, 2539-2541. (e) Hanashima, S.; Akai, S.; Sato, K. *Tetrahedron Lett.* 2008, 49, 5111-5114. |
| 12. (a) Okamoto, K.; Kondo, T.; Goto, T. *Tetrahedron* 1987, 43, 5909-5918. (b) Ito, Y.; Ogawa, T. *Tetrahedron Lett.* 1988, 29, 3987-3990. (c) Okamoto, K.; Goto, T. *Tetrahedron* 1990, 46, 5835-5857. (d) Ito, Y.; Ogawa, T. *Tetrahedron* 1990, 46, 89-102. (e) Erce'govec, T.; Magnusson, G. *J. Org. Chem.* 1995, 60, 3378-3384. (f) Martichonok, V.; Whitesides, G. M. *J. Am. Chem.* Soc. 1996, 118, 8187-8191. (g) Erce'govec, T.; Magnusson, G. *J. Org. Chem.* 1996, 61, 179-184. (h) Castro-Palomino, J. C.; Tsvetkov, Y. E.; Schmidt, R. R. *J. Am. Chem. Soc.* 1998, 120, 5434-5440; (i) Hossain, N.; Magnusson, G. *Tetrahedron Lett.* 1999, 40, 2217-2220. |
| 13. For reviews on C-5 modifications, see: (a) De Meo, C. *In Frontiers in Modern Carbohydrate Chemistry*, Demchenko, A. V. Ed.; American Chemical Society: Washington, DC, 2007; pp.118-131. (b) De Meo, C. *Carbohydr. Res.* 2008, 343, 1540-1552. |
| 14. (a) Yu, C.-S.; Niikura, K.; Lin, C.-C.; Wong, C.-H. *Angew. Chem. Int. Ed.* 2001, 40, 2900-2903. (b) Lin, C.-C.; Huang, K.-T.; Lin, C.-C. *Org. Lett.* 2005, 7, 4169-4172. (c) Tanaka, K.; Takashi, G.; Fukase, K. *Synlett.* 2005, 2958-2962. (d) Sun, B.; Srinivasan, B.; Huang, X.-F. *Chem. Eur. J.* 2008, 14, 7072-7081. (e) Tanaka, H.; Tateno, Y.; Nishiura, Y.; Takahashi, T. *Org. Lett.* 2008, 10, 5597-5600. (f) Crich, D.; Wu, B. *Org. Lett.* 2008, 10, 4033-4035. |
| 15. (a) Mootoo, D. R.; Konradsson, P.; Udodong, U.; Fraser-Reid, B. *J. Am. Chem. Soc.* 1988, 110, 5583-5584. (b) Fraser-Reid, B.; Wu, Z.; Udodong, U. E.; Ottoson, H. *J. Org. Chem.* 1990, 55, 6068-6070. |
| 16. (a) Raghavan, S.; Kahne, D. A. *J. Am. Chem. Soc.* 1993, 115, 1580-1581. |
| 17. (a) Koeller, K. M.; Wong, C.-H. *Chem. Rev.* 2000, 100, 4465-4493. (b) Lee, J.-C.; Greenberg, W. A.; Wong, C.-H. *Nat. Protoc.* 2006, 1, 3143-3152. |
| 18. (a) Seeberger, P. H.; Haase, W. C. *Chem. Rev.* 2000, 100, 4349-4393. (b) Plante, O. J.; Palmacci, E. R.; Seeberger, P. H. *Science* 2001, 291, 1523-1527. |
| 19. (a) Kanie, O.; Ito, Y.; Ogawa, T. *J. Am. Chem. Soc.* 1994, 116, 12073-12074. (b) Yamada, H.; Harada, T.; Miyazaki, H. Takahashi, T. *Tetrahedron Lett.* 1994, 35, 3979-3982. (c) Demchenko, A. V.; De Meo, C. *Tetrahedron Lett.* 2002, 43, 8819. (d) Kaeothip, S.; Pornsuriyasak, P.; Rath, N. P.; Demchenko, A. V. *Org. Lett.* 2009, 11, 799-802. |
| 20. (a) Nguyen, H. M.; Poole, J. L.; Gin, D. Y. *Angew. Chem. Int. Ed.* 2001, 40, 414-417. (b) Yamago, S.; Yamada, T; Maruyama, T.; Yoshida, J. I. *Angew. Chem. Int. Ed.* 2004, 43, 2145-2148. (c) Huang, X.; Huang, L.; Wang, H.; Ye, X.-S. *Angew. Chem. Int. Ed.* 2004, 43, 5221-5224. |
| 21. Ye, X.-S.; Huang, X.; Wong, C.-H. *Chem. Commun.* 2001, 974-975. |
| 22. Zhang, Z.; Niikura, K.; Huang, X.-F.; Wong, C.-H. *Can. J. Chem.* 2002, 80, 1051-1054. |
| 23. Wang, C.-C.; Lee, J.-C.; Luo, S.-Y.; Kulkarni, S. S.; Huang, Y.-W.; Lee, C.-C.; Chang, K.-L.; Hung, S.-C. *Nature* 2007, 446, 896-899. |
| 24. (a) Hashimoto, S.; Honda, T.; Ikegami, S. J. *Chem. Soc., Chem. Commun.* 1989, 685-687. (b) Boger, D. L.; Honda, T. *J. Am. Chem. Soc.* 1994, 116, 5647-5656. (c) Duynstee, H. I.; Wijsman, E. R.; van der Marel, G. A.; van Boom, J. H. *Synlett.* 1996, 313-314. (d) Vankayalapati, H.; Singh, G.; Tranoy, I. *Chem. Commun.* 1998, 2129-2130. (e) Vankayalapati, H.; Singh, G. *Tetrahedron Lett.* 1999, 40, 3925-3928. (f) Plante, O. J.; Andrade, R. B.; Seeberger, P. H. *Org. Lett.* 1999, 1, 211-214. (g) Singh, G.; Vankayalapati, H. *Tetrahedron: Asymmetry* 2000, 11, 125-138. (h) Plante, O. J.; Buchwald, S. L.; Seeberger, P. H. *J. Am. Chem. Soc.* 2000, 122, 7148-7149. (i) Plante, O. J.; Palmacci, E. R.; Seeberger, P. H. *Org. Lett.* 2000, 2, 3841-3843. (j) Plante, O. J.; Palmacci, E. R.; Andrade, R. B.; Seeberger, P. H. *J. Am. Chem. Soc.* 2001, 123, 9545-9554. (k) Tsuda, T.; Nakamura, S.; Hashimoto, S. *Tetrahedron* 2004, 60, 10711-10737. |
| 25. (a) Hung, S.-C.; Wong, C.-H. *Angew. Chem. Int. Ed. Engl.* 1996, 35, 2671-2674. (b) Palmacci, E. R.; Seeberger, P. H. *Org. Lett.* 2001, 3, 1547-1550. |
| 26. (a) Seeberger, P. H. *Chem. Commun.* 2003, 1115-1121. (b) Love, K. R.; Seeberger, P. H. *Angew. Chem. Int. Ed. Engl.* 2004, 43, 602-605. (c) Werz, D. B.; Seeberger, P. H. *Nat. Rev. Drug Discovery* 2005, 4, 751-763. |
| 27. (a) Crich, D.; Li, W. J. *J. Org. Chem.* 2007, 72, 2387-2391. (b) Crich, D.; Li, W. J. *J. Org. Chem.* 2007, 72, 7794-7797. (c) Liang, F.-F.; Chen, L.; Xing, G.-W. *Synlett.* 2009, 3, 425-428 |
| 28. (a) Tanaka, H.; Nishiura, Y.; Takahashi, T. *J. Am. Chem. Soc.* 2006, 128, 7124-7125. (b) Farris, M. D.; De Meo, C. *Tetrahedron Lett.* 2007, 48, 1225-1227. (c) Tanaka, H.; Nishiura, Y.; Takahashi, T. *J. Am. Chem. Soc.* 2008, 130, 17244-17245. |
| 29. Fridman, M.; Belakhov, V.; Yaron, S.; Bassov, T. *Org. Lett.* 2003, 5, 3575 |
| 30. Donohoe, T. J.; Logan, J. G.; Laffan, D. D. P. *Org. Lett.* 2003, 5, 4995-4998. |
| 31. (a) Komba, S.; Galustian, C.; Ishida, H.; Feizi, T.; Kannagi, R.; Kiso, M. *Angew. Chem. Int. Ed.* 1999, 38, 1131-1133. (b) Komba, S.; Yamaguchi, M.; Ishida, H.; Kiso, M. *Biol. Chem.* 2001, 382, 233-240. |
| 32. (a) Li, Z.; Gildersleeve, J. C. *J. Am. Chem. Soc.* 2006, 128, 11612-11619. (b) Li, Z.; Gildersleeve, J. C. *Tetrahedron Lett.* 2007, 48, 559-562. |
| 33. (a)Itzkowitz, S. H.; Yuan, M.; Montgomery, C. K.; Kjeldsen, T.; Takahashi, H. K.; Bigbee, W. L.; Kim, Y. S. *Cancer Res.* 1989, 49, 197- |

TABLE 10-continued

References 204. (b) Dabelsteen, E. *J. Pathol.* 1996, 179, 358-369.
34. Schwarz, J. B.; Kuduk, S. D.; Chen, X. T.; Sames, D.; Glunz, P. W.; Danishefsky, S. J. *J. Am. Chem. Soc.* 1999, 121, 2662-2673.
35. (a) Tanaka, H.; Adachi, M.; Takahashi, T. *Chem. Eur. J.* 2005, 11, 849-862. (b) Mathieux, N.; Paulsen, H.; Meldal, M.; Bock, K. *J. Chem. Soc., Perkin Trans. 1* 1997, 2359-2368.
36. Hasegawa, A.; Nagahama, T.; Ohki, H.; Hotta, K.; Ishida, H.; Kiso, M. *J. Carbohydr. Chem.* 1991, 10, 493-498
37. Nagao, Y.; Nekado, T.; Ikeda, K.; Achiwa, K. *Chem. Pharm. Bull.*1995, 43, 1536-1542.
38. Crich, D.; Smith, M. *J. Am. Chem. Soc.* 2001, 123, 9015-9020.
39. (a) Satoh, M.; Handa, K.; Saito, S.; Tokuyama, S.; Ito, A.; Miyao, N.; Orikasa, S.; Hakomori, S. *Cancer Res.* 1996, 56, 1932-1938. (b) Satoh, M.; Nejad, F. M.; Ohtani, H.; Ito, A.; Ohyama, C.; Saito, S.; Orikasa, S.; Hakomori, S. I. *Int. J. Oncol.* 2000, 16, 529-536.
40. (a) Katagiri, Y. U.; Ohmi, K.; Katagiri, C.; Sekino, T.; Nakajima, h.; Ebata, T.; Kiyokawa, N.; Fujimoto, J. *Glycoconjugate J.* 2001, 18, 347-353. (b) Wenk, J.; Andrews, P. W.; Casper, J.; Hata, J.; Pera, M. F.; von Keitz, A.; Damjanov, I.; Fenderson, B. A. *Int. J. Cancer* 1994, 58, 108-115. (c) Krupnick, J. G.; Damjanov, I.; Damjanov, A.; Zhu, Z. M.; Fenderson, B. A. *Int. J. Cancer* 1994, 59, 692-698. (d) Kannagi, R.; Levery, S. B.; Ishigami, F.; Hakomori, S.; Shevinsky, L. H.; Knowles, B. B.; Solter, D. *J. Biol. Chem.* 1983, 258, 8934-8942.
41. (a) Stapleton, A. E.; Stroud, M. R.; Hakomori, S.; Stamm, W. E. *Infect. Immun.* 1998, 66, 3856-3861. (b) Stroud, M. R.; Stapleton, A. E.; Levery, S. B. *Biochemistry* 1998, 37, 17420-17428. (c) Stapleton, A. E.; Nudelman, E.; Clausen, H.; Hakomori, S.; Stamm, W. E. *J. Clin. Invest.* 1992, 90, 965-972. (d) Cooling, L. L. W.; Koerner, T. A. W.; Naides, S. J. *J. Infect. Dis.* 1995, 172, 1198-1205.
42. Ishida, H.; Miyawaki, R.; Kiso, M.; Hasegawa, A. *J. Carbohydr. Chem.* 1996, 15, 163-182.
43. Lassaletta, J. M.; Carlsson, K.; Garegg, P. J.; Schmidt, R. R. *J. Org. Chem.* 1996, 61, 6873-6880.
44. Wang, Z.; Gilbert, M.; Eguchi, H.; Yu, H.; Cheng, J.; Muthana, S.; Zhou, L.; Wang, P. G.; Chen, X.; Huang, X. *Adv. Syn. Cat.* 2008, 350, 1717-1728.
45. Huang, C.-Y.; Thayer, D. A.; Chang, A. Y.; Best, M. D.; Hoffmann, J.; Head, S.; Wong, C.-H. *Proc. Nat. Acad. Sci. U.S.A.* 2006, 103, 15-20.
46. Angat, T.; Varki, A. *Chem. Rev.* 2002, 102, 439-470.
47. Dube, D. H.; Bertozzi, C. R. *Nat. Rev. Drug Discovery* 2005, 4, 477-488.
48. Tanaka, H.; Nishiura, Y.; Takahashi, T. *J. Org. Chem.* 2009, 74, 4383-4386.
49. Bouhroum, S.; Vottero, P. J. A. *Tetrahedron. Lett.* 1990, 31, 7441-7444.
50. Stephens, D. S. *FEMS Microbiol. Rev.* 2007, 31, 3-14.
51. Achtman, M. *Trends Microbiol* 1995, 3, 186-192.
52. Stephens, D. S.; Greenwood, B.; Brandtzaeg, P., *Lancet* 2007, 369, 2196-2210.
53. Taha, M. K.; Achtman, M.; Alonso, J. M.; Greenwood, B.; Ramsay, M.; Fox, A.; Gray, S.; Kaczmarski, E. *Lancet* 2000, 356, 2159.
54. Spinosa, M. R.; Progida, C.; Tala, A.; Cogli, L.; Alifano, P.; Bucci, C. *Infect. Immun.* 2007, 75, 3594-3603.
55. Schneider, M. C.; Exley, R. M.; Ram, S.; Sim, R. B.; Tang, C. M. *Trends Microbiol.* 2007, 15, 233-240.
56. Kugelberg, E.; Gollan, B.; Tang, C. M. *Vaccine* 2008, 26, I34-I39.
57. (a) Dabrowski, U.; Friebolin, H.; Brossmer, R.; Supp, M. *Tetrahedron Lett.* 1979, 4637-4640. (b) Vandervleugel, D. J. M.; Vanheeswijk, W. A. R.; Vliegenthart, J. F. G. *Carbohydr. Res.* 1982, 102, 121-130. (c) Paulsen, H.; Tietz, H. *Carbohydr. Res.* 1984, 125, 47-64. (d) Okamoto, K.; Kondo, T.; Goto, T. *Bull. Chem. Soc. Jpn.* 1987, 60, 637-643. (e) Kanie, O.; Kiso, M.; Hasegawa, A. *J. Carbohydr. Chem.* 1988, 7, 501-506.
58. Prytulla, S.; Lauterwein, J.; Klessinger, M.; Thiem, J. *Carbohydr. Res.* 1991, 215, 345-349.
59. Hasegawa, A.; Ohki, H.; Nagahama, T.; Ishida, H.; Kiso, M. *Carbohydr. Res.* 1991, 212, 277-281.
60. Demchenko, A. V.; Boons, G. J. *Tetrahedron Lett.* 1998, 39, 3065-3068.
61. Ando, H.; Koike, Y.; Ishida, H.; Kiso, M. *Tetrahedron Lett.* 2003, 44, 6883-6886.
62. De Meo, C.; Demchenko, A. V.; Boons, G. J. *Aust. J. Chem.* 2002, 55, 131-134.
63. Codee, J. D. C.; Litjens, R. E. J. N.; van den Bos, L. J.; Overkleeft, H. S.; van der Marel, G. *A. Chem. Soc. Rev.* 2005, 34, 769-782.
64. Ferguson, N. M.; Fraser, C.; Donnelly, C. A.; Ghani, A. C.; Anderson, R. M. *Science* 2004, 304, 968-9.
65. Garten, R. J.; Davis, C. T.; Russell, C. A.; Shu, B.; Lindstrom, S.; Balish, A.; Sessions, W. M.; Xu, X.; Skepner, E.; Deyde, V.; Okomo-Adhiambo, M.; Gubareva, L.; Barnes, J.; Smith, C. B.; Emery, S. L.; Hillman, M. J.; Rivailler, P.; Smagala, J.; de Graaf, M.; Burke, D. F.; Fouchier, R. A.; Pappas, C.; Alpuche-Aranda, C. M.; Lopez-Gatell, H.; Olivera, H.; Lopez, I.; Myers, C. A.; Faix, D.; Blair, P. J.; Yu, C.; Keene, K. M.; Dotson, P. D., Jr.; Boxrud, D.; Sambol, A. R.; Abid, S. H.; St George, K.; Bannerman, T.; Moore, A. L.; Stringer, D. J.; Blevins, P.; Demmler-Harrison, G. J.; Ginsberg, M.; Kriner, P.; Waterman, S.; Smole, S.; Guevara, H. F.; Belongia, E. A.; Clark, P. A.; Beatrice, S. T.; Donis,. R.; Katz, J.; Finelli, L.; Bridges, C. B.; Shaw, M.; Jernigan, D. B.; Uyeki, T. M.; Smith, D. J.; Klimov, A. I.; Cox, N. J. *Science* 2009, 325, 197-201
66. Smith, G. J.; Vijaykrishna, D.; Bahl, J.; Lycett, S. J.; Worobey, M.; Pybus, O. G.; Ma, S. K.; Cheung, C. L.; Raghwani, J.; Bhatt, S.; Peiris, J. S.; Guan, Y.; Rambaut, A. *Nature* 2009, 459, 1122-5.
67. Skehel, J. J.; Wiley, D. C. *Annu Rev Biochem* 2000, 69, 531-69.
68. Wilson, I. A.; Skehel, J. J.; Wiley, D. C. *Nature* 1981, 289, 366-73.
69. Varki, A. *Nature* 2007, 446, 1023-9.
70. Rogers, G. N.; Pritchett, T. J.; Lane, J. L.; Paulson, J. C. *Virology* 1983, 131, 394-408.
71. Gambaryan, A. S.; Karasin, A. I.; Tuzikov, A. B.; Chinarev, A. A.; Pazynina, G. V.; Bovin, N. V.; Matrosovich, M. N.; Olsen, C. W.; Klimov, A. I. *Virus Res* 2005, 114, 15-22.
72. Rogers, G. N.; Paulson, J. C. *Virology* 1983, 127, 361-73.
73. Kumari, K.; Gulati, S.; Smith, D. F.; Gulati, U.; Cummings, R. D.; Air, G. M. *Virol J* 2007, 4, 42.
74. Yen, H. L.; Aldridge, J. R.; Boon, A. C.; Ilyushina, N. A.; Salomon, R.; Hulse-Post, D. J.; Marjuki, H.; Franks, J.; Boltz, D. A.; Bush, D.; Lipatov, A. S.; Webby, R. J.; Rehg, J. E.; Webster, R. G. *Proc Natl Acad Sci USA* 2009, 106, 286-91.
75. Vinikoor, M.; Stevens, J.; Nawrocki, J.; Singh, K. *J Clin Microbiol* 2009, 47, 3055-6.
76. de Boer, G. F.; Back, W.; Osterhaus, A. D. *Arch Virol* 1990, 115, 47-61.
77. Skropeta, D. *Bioorg Med Chem* 2009, 17, 2645-53.
78. Deom, C. M.; Caton, A. J.; Schulze, I. T. *Proc Natl Acad Sci USA* 1986, 83, 3771-5.
79. Wang, C. C.; Chen, J. R.; Tseng, Y. C.; Hsu, C. H.; Hung, Y. F.; Chen, S. W.; Chen, C. M.; Khoo, K. H.; Cheng, T. J.; Cheng, Y. S.; Jan, J. T.; Wu, C. Y.; Ma, C.; Wong, C. H. *Proc Natl Acad Sci USA* 2009, 106, 18137-42.
80. Hsu, C. H.; Chu, K. C.; Lin, Y. S.; Han, J. L.; Peng, Y. S.; Ren, C. T.; Wu, C. Y.; Wong, C. H. *Chem. Eur. J.* 2010, 16, 1754-60.
81. Komba, S.; Galustian, C.; Ishida, H.; Feizi, T.; Kannagi, R.; Kiso, M. *Angew. Chem. Int. Ed.* 1999, 38, 1131-1133.
82. Komba, S.; Yamaguchi, M.; Ishida, H.; Kiso, *M. Biol Chem* 2001, 382, 233-40.
83. Yamaguchi, M.; Ishida, H.; Kanamori, A.; Kannagi, R.; Kiso, M. *J. Carbohydrat. Chem.* 2004, 23, 201-215.
84. Stevens, J.; Corper, A. L.; Basler, C. F.; Taubenberger, J. K.; Palese, P.; Wilson, I. A. *Science* 2004, 303, 1866-70.
85. Srinivasan, A.; Viswanathan, K.; Raman, R.; Chandrasekaran, A.; Raguram, S.; Tumpey, T. M.; Sasisekharan, V.; Sasisekharan, R. *Proc Natl Acad Sci USA* 2008, 105, 2800-5.
86. Inkster, M. D.; Hinshaw, V. S.; Schulze, I. T. *J Virol* 1993, 67, 7436-43.
87. Gunther, I.; Glatthaar, B.; Doller, G.; Garten, W. *Virus Res* 1993, 27, 147-60.
88. Tsuchiya, E.; Sugawara, K.; Hongo, S.; Matsuzaki, Y.; Muraki, Y.; Nakamura, K. *J Gen Virol* 2002, 83, 3067-74.
89. Roberts, P. C.; Garten, W.; Klenk, H. D. *J Virol* 1993, 67, 3048-60.
90. Tsuchiya, E.; Sugawara, K.; Hongo, S.; Matsuzaki, Y.; Muraki, Y.; Li, Z. N.; Nakamura, K. *J Gen Virol* 2002, 83, 1137-46.
91. Vigerust, D. J.; Shepherd, V. L. *Trends Microbiol* 2007, 15, 211-8.
92. Chen, M. W.; Cheng, T. J.; Huang, Y.; Jan, J. T.; Ma, S. H.; Yu, A. L.; Wong, C. H.; Ho, D. D. *Proc Natl Acad Sci USA* 2008, 105, 13538-43.
93. Liang, P. H.; Imamura, M.; Li, X.; Wu, D.; Fujio, M.; Guy, R. T.; Wu, B. C.; Tsuji, M.; Wong, C. H. *J Am Chem Soc* 2008, 130, 12348-54.
94. Matrosovich M, et al. *J. Virol.* 1999, 73, 1146-1155.

Although specific embodiments of the invention have been described herein for purposes of illustration, various modifications may be made without deviating from the spirit and scope of the invention. Accordingly, the invention is not limited except as by the appended claims.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A sialyl phosphate donor compound for synthesis of sialosides comprising:
    an N-acetyl-5-N,4-O-carbonyl, a 5-N,4-O-carbonyl, a 5-N-Trifluoroacetyl, a or 5-azido; and
    an alkyl, aryl or mixed alkyl aryl phosphate leaving group.

2. The compound of claim 1, having the structure:

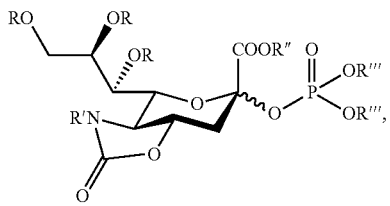

wherein R is independently H or a group selected from: acetyl, chloroacetyl, benzyl, thiobenzyl, benzylidine, and phenacyl, R' is independently H or an N-protective group, or an acetyl, or a formyl;

R" is independently H or selected from the group consisting of: $C_1$-$C_{20}$ alkyl, $C_6$-$C_{20}$ aryl, $C_2$-$C_{20}$ alkenyl, $C_2$-$C_{20}$ alkynyl, $C_3$-$C_{20}$ cycloalkyl, $C_3$-$C_{20}$ cycloaryl, $C_3$-$C_{20}$ cycloalkenyl, heteroaryl, aralkyl and heteroaralkyl, each R'" is independently selected from the group consisting of: $C_1$-$C_{20}$ alkyl, $C_6$-$C_{20}$ aryl, $C_2$-$C_{20}$ alkenyl, $C_2$-$C_{20}$ alkynyl, $C_3$-$C_{20}$ cycloalkyl, $C_3$-$C_{20}$ cycloaryl, $C_3$-$C_{20}$ cycloalkenyl, heteroaryl, aralkyl and heteroaralkyl, and any salt or stereoisomer thereof.

3. The compound according to claim 1, having the structure:

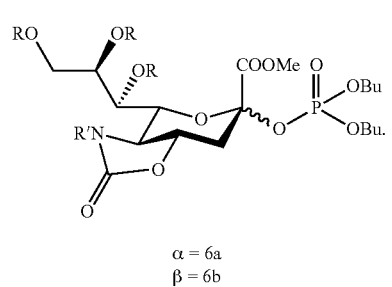

α = 6a
β = 6b

R = Ac or ClAc
R' = H or Ac

4. A method for synthesizing a sialoside, the method comprising:
    coupling a thiosialoside with a dibutyl phosphate in the presence of N-iodosuccinimide and catalytic trifluoromethanesulfonic (triflic) acid under suitable conditions; and
    isolating an N-acetyl-5-N,4-O-carbonyl-protected dibutyl sialyl phosphate donor.

5. The method of claim 4, wherein the sialoside comprises an α-glycosidic linkage.

6. The method of claim 4, wherein the thiosialoside is selected from the group consisting of:

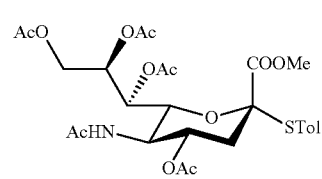

1a

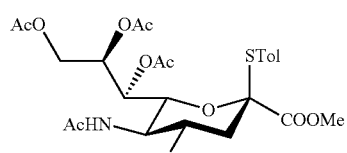

1b

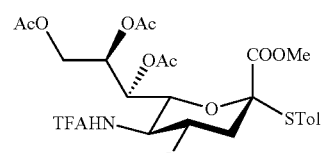

3a

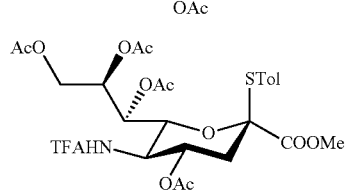

3b

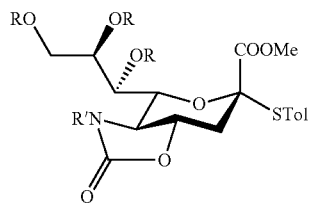

5a

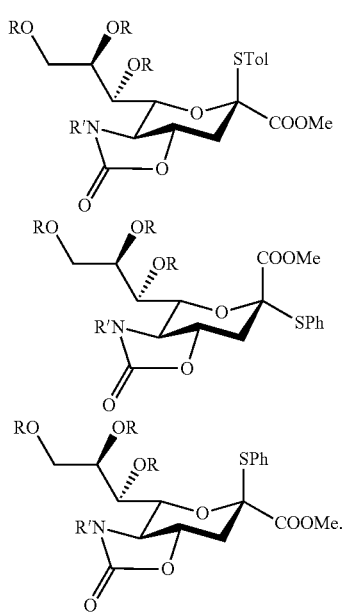

R = Ac or ClAc
R' = H or Ac

7. The method of claim 4, further comprising: separating sialyl α-phosphate from sialyl-β phosphate by a process comprising chromatography.

8. The method of claim 4, wherein the N-acetyl-5-N,4-O-carbonyl- or protected dibutyl sialyl phosphate donor comprises sialyl α-phosphate 6a or sialyl-β phosphate 6b having the formula:

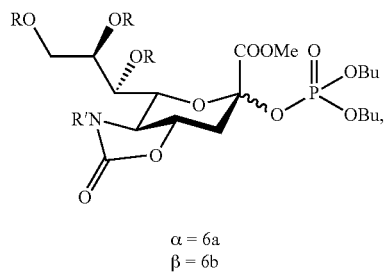

α = 6a
β = 6b

R = Ac or ClAc
R' = H or Ac and wherein the N-acetyl-5-N,4-O-carbonyl- or 5-N,4,-O-carbonyl-protected thiosialoside is:

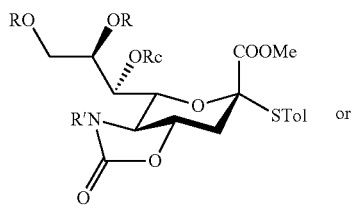

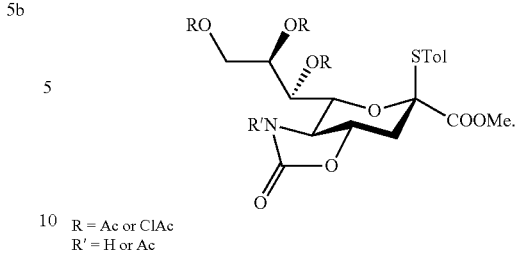

R = Ac or ClAc
R' = H or Ac

9. The method of claim 4, further comprising the steps of α-selective synthesis of a sialyl disaccharide building block comprising N-acetyl neuraminic acid (Neu5Ac) by:

coupling the N-acetyl-5-N,4-O-carbonyl or 5-N,4,-O-carbonyl-protected dibutyl sialyl phosphate donor with a suitable thiogalactoside acceptor.

10. The method of claim 9, wherein the disaccharide building block comprising N-acetyl neuraminic acid (Neu5Ac) is primarily α-anomeric.

11. The method of claim 9, wherein the coupling is promoted by the reagent trimethylsilyl trifluoromethanesulfonate (TMSOTf).

12. The method of claim 9, wherein the sialyl disaccharide building block is Neu5Acα(2→6)Gal, and a 4,6-dihydroxy thiogalactoside acceptor of the formula:

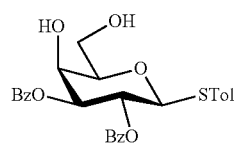

is coupled with the N-acetyl-5-N,4-O-carbonyl-protected dibutyl sialyl phosphate donor 6a to produce a Neu5Acα (2→6)Gal of the formula:

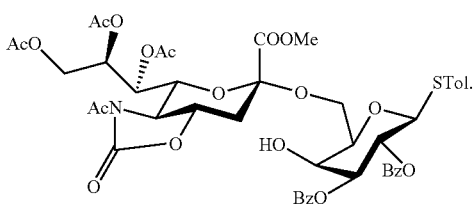

13. The method of claim 9, wherein the sialyl disaccharide building block is Neu5Acα(2→3)Gal, and a tolyl-2-O-benzoyl-4,6-benzylidine-1-thio-β-D-galactopyranoside acceptor 17 of the formula:

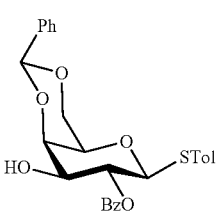

is coupled with the N-acetyl-5-N,4-O-carbonyl-protected dibutyl sialyl phosphate donor 6a to produce a Neu5Acα (2→3)Gal of the formula:

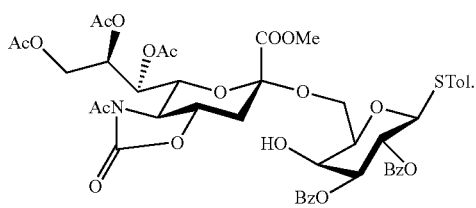

14

14. The method of claim 9, wherein the sialyl disaccharide building block is Neu5Acα(2→6)GalNAc, and a tolyl-2-O-benzoyl-4,6-benzylidine-1-thio-β-D-galactopyranoside acceptor 19 or 21 of the formula:

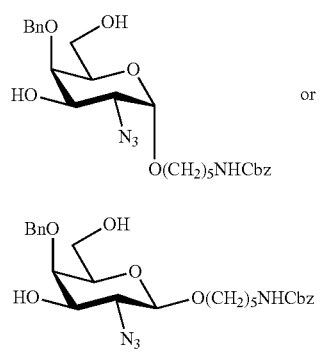

19 or

21 is coupled with the N-acetyl-5-N,4-O-carbonyl-protected dibutyl sialyl phosphate donor 6a to produce a Neu5Acα (2→6)GalNAc of the formula:

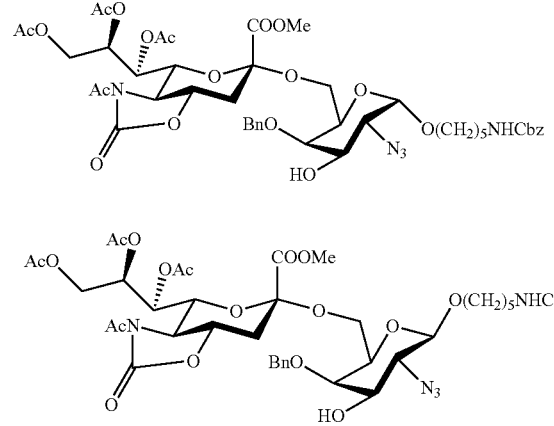

20 or

22 respectively.

15. The method of claim 14, wherein the Neu5Acα(2→6) GalNAc disaccharide building block is used for the synthesis of an O-sialylated antigen STn, 2,6-STF, 2,3-STF, or glycophorin.

16. The method of claim 4, further comprising the steps of a one pot α-selective synthesis of a sialyl trisaccharide building block comprising N-acetyl neuraminic acid (Neu5Ac) by:

first contacting the N-acetyl-5-N,4-O-carbonyl-protected dibutyl sialyl phosphate donor with a first thiogalactoside acceptor in a reaction for a time suitable to produce a disaccharide; and then adding a second acceptor to the reaction mix and allowing a second coupling reaction to produce a trisaccharide.

17. The method of claim 16, wherein the trisaccharide comprises an influenza hemagglutinin (HA) receptor α(2→3) linked or α(2→6) linked trisaccharide.

18. The method of claim 16, wherein the second acceptor is a trisaccharide.

19. The method of claim 18 wherein the one pot reaction produces a monosialosyl globopentaosylceramide, stage specific embryonic antigen-4 (SSEA-4).

20. The method of claim 9, wherein the sialyl disaccharide building block is Neu5Acα(2→8)Neu5Ac, and a 7,8-dihydroxy thiosialoside acceptor of the formula 40:

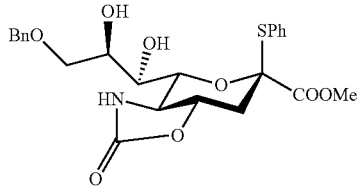

40 is coupled with the N-acetyl-5-N,4-O-carbonyl-protected dibutyl sialyl phosphate donor 6a to produce a Neu5Acα (2→8)Neu5Ac of the formula 41:

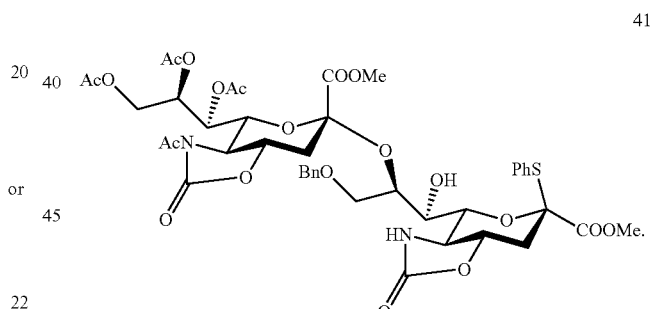

41

21. The method of claim 9, wherein the sialyl disaccharide building block is Neu5Acα(2→9)Neu5Ac, and a 7,8,9-trihydroxy thiosialoside acceptor of the formula 42:

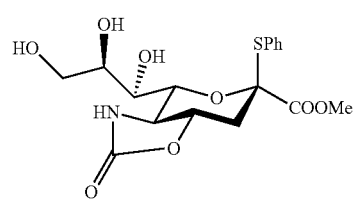

42 is coupled with the N-acetyl-5-N,4-O-carbonyl-protected dibutyl sialyl phosphate donor 6a to produce a Neu5Acα(2→9)Neu5Ac of the formula 43:

43

[Chemical structure]

22. The method of claim 21, further comprising α-selective synthesis of a sialyl α(2→9) tetrasaccharide comprising N-acetyl neuraminic acid (Neu5Ac) by:
   first contacting the N-acetyl-5-N,4-O-carbonyl-protected dibutyl sialyl phosphate donor with a suitable thiosialoside acceptor in a reaction for a time suitable to produce a first thiophenyl disialic acid comprising Neu5Acα(2→9)Neu5Ac disaccharide with an SPh leaving group in the reducing end;
   then transferring the thiophenyl disialic acid to the dibutyl sialyl phosphate donor; and then adding a second Neu5Acα(2→9)Neu5Ac disaccharide to the reaction mix and allowing a second coupling reaction to produce a (Neu5Acα(2→9)Neu5Ac)$_2$ tetrasialoside.

23. The method of claim 22, wherein the tetrasialoside is a component of capsular polysaccharide of *Neisserian meningitidis* type C.

24. The method of claim 22, further comprising preparation of a (Neu5Acα(2→9)Neu5Ac)$_4$ octosialoside.

25. The method of claim 23, wherein the octosialoside comprises a synthetic antigen for *Neisserian meningitidis*.

26. The method of claim 23, wherein the octosialoside further comprises an azido alkyl pentyl group in the reducing end suitable for conjugating the octosialoside to a protein or peptide.

27. The method of claim 20, further comprising α-selective synthesis of α(2→8)/α(2→9) alternative polysialic acids by:
   first contacting the N-acetyl-5-N,4-O-carbonyl-protected dibutyl sialyl phosphate donor with a suitable thiosialoside acceptor in a reaction for a time suitable to produce a first thiophenyl disialic acid comprising α(2→8) disialic acid with an SPh leaving group in the reducing end;
   then transferring the thiophenyl disialic acid to the dibutyl sialyl phosphate donor; and then
   adding a one or more disaccharides comprising α(2→8) disialic acid with 7,8,9trihydroxy groups and optionally, a second α(2→8) disialic acid to the reaction mix and allowing a series of additional coupling reactions to produce one or more of α(2→8)/α(2→9) alternative tetra-, hexa-, octa-, or other polysialic acids.

28. The method of claim 9, further comprising a programmable one-pot synthesis of oligosaccharides by:
   determining a relative reactive value (RRV) of a synthetic sialylated disaccharide; and
   programming a sequence for synthesis of a sialylated polysaccharide wherein the reactivity of a sialylated disaccharide is determined by the second reside of the disaccharide.

29. The method of claim 9, wherein the sialyl disaccharide building blocks comprise one or more of the group consisting of Neu5Acα(2→3)Gal, Neu5Acα(2→6)Gal, Neu5Acα(2→6)GalNAc, Neu5Acα(2→9)Neu5Ac, and Neu5Acα(2→8)Neu5Ac.

30. The method of claim 9, further comprising: assembling a library of sialosides using sialyl disaccharide building blocks comprising N-acetyl neuraminic acid (Neu5Ac).

31. The method of claim 30, wherein the library of sialosides comprise receptors of influenza virus hemagglutinin (HA) proteins.

32. The method of claim 30, further comprising: immobilizing a plurality of members of the library of sialosides on an array.

33. A method for detecting binding to a sialoside, the method comprising:
   synthesizing a plurality of sialyl polysaccharides, comprising the step of coupling a N-acetyl-5-N,4-O-carbonyl- or 5-N,4-O-carbonyl-protected dibutyl sialyl phosphate donor with a suitable acceptor, to form sialyl disaccharide building blocks;
   immobilizing said polysaccharides at discrete sites on an array;
   contacting the array with a sample suspected of containing an agent that binds to a sialoside on the array;
   detecting a binding reaction of the array; and
   determining the presence or absence of the agent from detecting the binding reaction on the array.

34. The method of claim 33, wherein the sialoside on the array comprises a glycan found on a cell surface receptor.

35. The method of claim 33, wherein the agent comprises a surface glycoprotein of a pathogen or active fragment thereof.

36. The method of claim 33, wherein the agent comprises an influenza hemagglutinin protein or active fragment thereof.

37. The method of claim 36, wherein the influenza hemagglutinin protein or active fragment thereof comprises a natural virus.

38. The method of claim 36, wherein the influenza hemagglutinin protein or active fragment thereof comprises a recombinant HA protein, polypeptide or active variant thereof.

39. The method of claim 33, wherein the array comprises α(2→3), α(2→6), α(2→8) and α(2→9) sialosides of varying lengths.

40. The method of claim 39, wherein a binding pattern on the array is distinctive of a strain of influenza virus.

41. The method of claim 40, wherein the strain of influenza virus is selected from the group consisting of H1N1, H3N1, H3N2, H5N1, H5N2, H7N7, and H9N2.

42. The method of claim 40, wherein a binding profile the HA protein or fragment from a strain of influenza virus is dependent on the sequence or length of α(2→3), α(2→6), α(2→8) and α(2→9) silosides.

43. The method of claim 40, wherein the strain of influenza virus is selected from the group consisting of pandemic Cal/09 H1N1, seasonal Brisbane/59/2007 (Br/59/07), H1N1/New Calcdonia/1999 (NC/99), Brisbane H3N1, and NIBRG-14 (H5N1), Br10 (H3N2), Cal07(H1N1) H5 (Vietnam 1194/2004 and CHAS), WSN(H1N1) 1933, and A/Puerto Rico/8/34 (H1N1): PR8 strain influenza virus.

* * * * *